US008124738B2

(12) United States Patent
Terret et al.

(10) Patent No.: US 8,124,738 B2
(45) Date of Patent: Feb. 28, 2012

(54) HUMAN MONOCLONAL ANTIBODIES TO CD70

(75) Inventors: Jonathan Alexander Terret, Los Altos, CA (US); Li-sheng Lu, Mountain View, CA (US); David John King, Belmont, CA (US); Josephine M. Cardarelli, San Carlos, CA (US); Chin Pan, Los Altos, CA (US); Haichun Huang, Fremont, CA (US); Marco A. Coccia, Scotts Valley, CA (US)

(73) Assignee: Medarex, Inc., Princeton, NJ (US)

( * ) Notice: Subject to any disclaimer, the term of this patent is extended or adjusted under 35 U.S.C. 154(b) by 708 days.

(21) Appl. No.: 12/065,436

(22) PCT Filed: Sep. 26, 2006

(86) PCT No.: PCT/US2006/037753
§ 371 (c)(1),
(2), (4) Date: Sep. 9, 2008

(87) PCT Pub. No.: WO2007/038637
PCT Pub. Date: Apr. 5, 2007

(65) Prior Publication Data
US 2009/0028872 A1    Jan. 29, 2009

Related U.S. Application Data

(60) Provisional application No. 60/720,600, filed on Sep. 26, 2005, provisional application No. 60/726,695, filed on Oct. 13, 2005, provisional application No. 60/748,827, filed on Dec. 8, 2005.

(51) Int. Cl.
C07K 16/00    (2006.01)
A61K 39/395   (2006.01)
A61K 39/00    (2006.01)

(52) U.S. Cl. ............... 530/387.1; 530/387.7; 530/388.1; 530/388.15; 530/388.73; 530/388.75; 530/388.8; 530/388.85; 530/391.1; 424/141.1; 424/142.1; 424/152.1; 424/154.1; 424/155.1; 424/156.1

(58) Field of Classification Search .................. 424/130, 424/133, 134, 156.1; 435/7.23, 375
See application file for complete search history.

(56) References Cited

U.S. PATENT DOCUMENTS

| 5,162,504 | A | 11/1992 | Horoszewicz |
| 5,332,837 | A | 7/1994 | Kelly et al. |
| 5,475,092 | A | 12/1995 | Chari et al. |
| 5,538,866 | A | 7/1996 | Israeli et al. |
| 5,573,924 | A | 11/1996 | Beckmann et al. |
| 5,621,002 | A | 4/1997 | Bosslet et al. |
| 5,739,350 | A | 4/1998 | Kelly et al. |
| 5,843,937 | A | 12/1998 | Wang et al. |
| 6,107,090 | A | 8/2000 | Bander |
| 6,124,345 | A | 9/2000 | Wetterich et al. |
| 6,130,237 | A | 10/2000 | Denny et al. |
| 6,136,311 | A | 10/2000 | Bander |
| 6,214,345 | B1 | 4/2001 | Firestone et al. |
| 6,342,219 | B1 | 1/2002 | Thorpe et al. |
| 6,534,660 | B1 | 3/2003 | Yongxin et al. |
| 6,586,618 | B1 | 7/2003 | Zhao et al. |
| 6,756,397 | B2 | 6/2004 | Zhao et al. |
| 7,049,316 | B2 | 5/2006 | Zhao et al. |
| 7,091,186 | B2 | 8/2006 | Senter et al. |
| 7,105,159 | B1 | 9/2006 | Israeli et al. |
| 7,109,304 | B2 | 9/2006 | Hansen et al. |
| 7,223,837 | B2 | 5/2007 | De Groot et al. |
| 7,235,578 | B2 | 6/2007 | Denny et al. |
| 7,261,892 | B2 | 8/2007 | Terrett |
| 7,329,706 | B2 | 2/2008 | Fukui et al. |
| 2002/0004587 | A1 | 1/2002 | Miller et al. |
| 2003/0003101 | A1 | 1/2003 | Bander |
| 2003/0096743 | A1 | 5/2003 | Senter et al. |
| 2003/0130189 | A1 | 7/2003 | Senter et al. |
| 2003/0195365 | A1 | 10/2003 | Zhao et al. |
| 2003/0199519 | A1 | 10/2003 | Zhao et al. |
| 2004/0109867 | A1 | 6/2004 | Yongxin et al. |
| 2004/0141981 | A1 | 7/2004 | Sontheimer et al. |
| 2004/0192597 | A1 | 9/2004 | Raitano et al. |
| 2004/0202665 | A1 | 10/2004 | Lazarovits et al. |
| 2005/0014700 | A1 | 1/2005 | Boger |
| 2005/0070693 | A1 | 3/2005 | Hansen et al. |
| 2005/0096261 | A1 | 5/2005 | Szekely et al. |
| 2005/0142062 | A1 | 6/2005 | Sontheimer et al. |
| 2005/0191299 | A1 | 9/2005 | Swamy et al. |
| 2005/0214310 | A1 | 9/2005 | Toki et al. |
| 2005/0238649 | A1 | 10/2005 | Doronina et al. |
| 2005/0282168 | A1 | 12/2005 | Liu et al. |
| 2006/0003960 | A1 | 1/2006 | Polakis |
| 2006/0009462 | A1 | 1/2006 | Yongxin et al. |
| 2006/0013860 | A1 | 1/2006 | Ng et al. |
| 2006/0024317 | A1 | 2/2006 | Boyd et al. |
| 2006/0074008 | A1 | 4/2006 | Senter et al. |
| 2006/0083736 | A1 | 4/2006 | Law et al. |

(Continued)

FOREIGN PATENT DOCUMENTS

WO      WO 94/05691        3/1994

(Continued)

OTHER PUBLICATIONS

Janeway et al. (Immunobiology 5, 2001, p. 100-101).*

(Continued)

Primary Examiner — Peter J Reddig
Assistant Examiner — Yan Xiao
(74) Attorney, Agent, or Firm — Baker Botts L.L.P.

(57) ABSTRACT

The present disclosure provides isolated monoclonal antibodies, particularly human monoclonal antibodies, that specifically bind to CD70 with high affinity. Nucleic acid molecules encoding the antibodies of the disclosure, expression vectors, host cells and methods for expressing the antibodies of the disclosure are also provided. Immunoconjugates, bispecific molecules and pharmaceutical compositions comprising the antibodies of the disclosure are also provided. The disclosure also provides methods for treating cancer, autoimmune disease, inflammation and viral infections.

22 Claims, 53 Drawing Sheets

U.S. PATENT DOCUMENTS

| | | | |
|---|---|---|---|
| 2006/0233791 | A1 | 10/2006 | Tedder et al. |
| 2006/0233794 | A1 | 10/2006 | Law et al. |
| 2006/0233814 | A1 | 10/2006 | Goldmakher et al. |
| 2006/0257317 | A1 | 11/2006 | Bigner et al. |
| 2006/0275212 | A1 | 12/2006 | Bander |
| 2007/0036797 | A1 | 2/2007 | Kim et al. |
| 2007/0128593 | A1 | 6/2007 | Petroziello et al. |
| 2007/0135346 | A1 | 6/2007 | Zhao et al. |
| 2007/0160573 | A1 | 7/2007 | Gengrinovitch |
| 2007/0269369 | A1 | 11/2007 | Gegg et al. |
| 2007/0292422 | A1 | 12/2007 | Law et al. |
| 2008/0025989 | A1 | 1/2008 | Law et al. |
| 2010/0150950 | A1* | 6/2010 | Coccia et al. ............ 424/178.1 |

FOREIGN PATENT DOCUMENTS

| | | |
|---|---|---|
| WO | WO 96/34096 | 10/1996 |
| WO | WO 97/35616 | 10/1997 |
| WO | WO 02/43478 | 6/2002 |
| WO | WO 02/100336 | 12/2002 |
| WO | WO 03/046581 | 6/2003 |
| WO | WO 03/087055 | 10/2003 |
| WO | WO 2004/002528 | 1/2004 |
| WO | WO 2004/010957 | 2/2004 |
| WO | WO 2004/073656 | 9/2004 |
| WO | WO 2004/104045 | 12/2004 |
| WO | WO 2005/023993 | 3/2005 |
| WO | WO 2005/036176 | 4/2005 |
| WO | WO 2005/058815 | 6/2005 |
| WO | WO 2006/002895 | 1/2006 |
| WO | WO 2006/009805 | 1/2006 |
| WO | WO 2006/044643 | 4/2006 |
| WO | WO 2006/065533 | 6/2006 |
| WO | WO 2006/113909 | 10/2006 |
| WO | WO 2006/119285 | 11/2006 |
| WO | WO 2006/130773 | 12/2006 |
| WO | WO 2007/038637 | 4/2007 |
| WO | WO 2007/038658 | 4/2007 |
| WO | WO 2007/051081 | 5/2007 |
| WO | WO 2007/089149 | 8/2007 |
| WO | WO 2007/144882 | 12/2007 |

OTHER PUBLICATIONS

Rudikoff et al (Proc Natl Acad Sci USA 1982 vol. 79 p. 1979).*
Bowie et al, Science, 247:1306-1310, 1990, p. 1306.*
Gussow et al. (1991, Methods in Enzymology 203:99-121).*
Straub P et al, 1993, J Biol Chem 268(29): 21,997-22,003.*
Kouklis PD et al, 1993, J Cell Science, 106: 919-928.*
Schreier et al. (Nucl Acids Res. 1986, 14:2381-2389).*
Balint R F et al.; Antibody Engineering by Parsimonious Mutagenesis; Gene; Elsevier, Amsterdam, NL; 1993; vol. 137; No. 1; pp. 109-118.
Hintzen R Q et al.; Characterization of the Human CD27 Ligand, A Novel Member of the TNF Gene Family; Journal of Immunology, The Williams and Wilkins Co. Baltimore; vol. 152, No. 4; 1994; pp. 1762-1773.
Yang F C et al; CD27/CD70 Interaction Directly Induces Natural Killer Cell Killing Activity; Immunology; Blackwell Publishing, Oxfor, GB; vol. 88; No. 2; 1996; pp. 289-293.
Shields R L et al.; Lack of Fucose on Human IgG1 N-Linked Oligosaccharide Improves Binding to Human FcgammRIII and Antibody-dependent Cellular Toxicity; Journal of Biological Chemistry; American Society of Biochemical Biologists; Birmingham, US; 2002; vol. 277, No. 30; pp. 26733-26740.
BD Biosciences Product Catalog Pharmingen; 2003; BD Biosciences; XP002440779; p. 138.
Garcia Pilar et al.; Signalling via CD70, a member of the TNF family, regulates T cell functions; Journal of Leukocyte Biology; 2004; pp. 263-270.
Adam P J et al.; CD70 (TNFSF7) is Expressed at High Prevalence in Renal Cell Carcinomas and is Rapidly Internalised on Antibody Binding; British Journal of Cancer; 2006; vol. 95; No. 3; pp. 298-306.
Law, Che-Leung, et al., "Anti-CD70 antibody drug conjugates mediated renal carcinoma cell killing through cytotoxic drug delivery and antibody-dependent cellular cytotoxicity", *Proc. Amer Assoc Cancer Res.*, vol. 46, Abstract #6143, 2005.
Boder et al., "Directed evolution of antibody fragments with monovalent femtomolar antigen-binding affinity," Proc Natl Acad Sci U S A. Sep. 26, 2000;97(20):10701-5.
Hamann, "Monoclonal antibody-drug conjugates," Expert Opinion on Therapeutic Patents, Informa Healthcare, GB, vol. 15, No. 9, Jan. 1, 2005, pp. 1087-1103.
Jeffrey et al., "Development and properties of beta-glucuronide linkers for monoclonal antibody-drug conjugates," Bioconjug Chem. May-Jun. 2006;17(3):831-40.
Law et al., "Lymphocyte activation antigen CD70 expressed by renal cell carcinoma is a potential therapeutic target for anti-CD70 antibody-drug conjugates," Cancer Res. Feb. 15, 2006;66(4):2328-37.
Terrett et al., "CD70 antibody based drugs: two different mechanisms of action for the treatment of multiple cancer types," Proceedings of the American Association for Cancer Research Annual Meeting, vol. 47, Apr. 2006, p. 470, Abstract 1995.
Wark & Hudson, "Latest technologies for the enhancement of antibody affinity," Adv Drug Deliv Rev. Aug. 7, 2006;58(5-6):657-70. Epub May 22, 2006.
Wu & Senter, "Arming antibodies: prospects and challenges for immunoconjugates," Nat Biotechnol. Sep. 2005;23(9):1137-46.
Dubowchik, et al., 2002, "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," *Bioconjugate Chem*, vol. 13: p. 855-869.
Ancell Corporation, "Monoclonal anti-human CD70/Biotin", catalog No. 222-30, http://www.ancell.com/repository/1/441/p222_030.pdf, downloaded Jun. 29, 2011.

* cited by examiner

Anti-CD70 2H5 VK Regions

V segment: L6
J segment: JK4

```
      E   I   V   L   T   Q   S   P   A   T   L   S   L   S   P   G   E   R
  1  GAA ATT GTG TTG ACA CAG TCT CCA GCC ACC CTG TCT TTG TCT CCA GGG GAA AGA
                                            CDR1
                            ------------------------------------------------
      A   T   L   S   C   R   A   S   Q   S   V   S   S   Y   L   A   W   Y
 55  GCC ACC CTC TCC TGC AGG GCC AGT CAG AGT GTT AGC AGC TAC TTA GCC TGG TAC
                                                                    CDR2
                                                                ------------
      Q   Q   K   P   G   Q   A   P   R   L   L   I   Y   D   A   S   N   R
109  CAA CAG AAA CCT GGC CAG GCT CCC AGG CTC CTC ATC TAT GAT GCA TCC AAC AGG

CDR2
     --------
      A   T   G   I   P   A   R   F   S   G   S   G   S   G   T   D   F   T
163  GCC ACT GGC ATC CCA GCC AGG TTC AGT GGC AGT GGG TCT GGG ACA GAC TTC ACT
                                                                    CDR3
                                                                 -------
      L   T   I   S   S   L   E   P   E   D   F   A   V   Y   Y   C   Q   Q
217  CTC ACC ATC AGC AGC CTA GAG CCT GAA GAT TTT GCA GTT TAT TAC TGT CAG CAG

CDR3
     ----------------------------
      R   T   N   W   P   L   T   F   G   G   G   T   K   V   E   I   K
271  CGT ACC AAC TGG CCG CTC ACT TTC GGC GGA GGG ACC AAG GTG GAG ATC AAA
```

Figure 1B

Anti-CD70 10B4 VH Regions

V segment:     3-30.3
D segment:         4-11
J segment:     JH4b

```
      Q   I   Q   L   V   E   S   G   G   G   V   V   Q   P   G   R   S   L
  1   CAA ATA CAA CTG GTG GAG TCT GGG GGA GGC GTG GTC CAG CCT GGG AGG TCC CTG

CDR1
                                                     ------------------------
      R   L   S   C   A   A   S   G   F   T   F   G   Y   Y   A   M   H   W
 55   AGA CTC TCC TGT GCA GCC TCT GGA TTC ACC TTC GGT TAC TAT GCT ATG CAC TGG

CDR2
                                                     ------------------------
      V   R   Q   A   P   G   K   G   L   E   W   V   A   V   I   S   Y   D
109   GTC CGC CAG GCT CCA GGC AAG GGG CTG GAG TGG GTG GCA GTT ATA TCA TAT GAT

CDR2
      ----------------------------------------------------
      G   S   I   K   Y   Y   A   D   S   V   K   G   R   F   T   I   S   R
163   GGA AGC ATT AAA TAC TAC GCA GAC TCC GTG AAG GGC CGA TTC ACC ATC TCC AGA

D   N   S   K   N   T   L   Y   L   Q   M   N   S   L   R   A   E   D
217   GAC AAT TCC AAG AAC ACG CTG TAT CTG CAA ATG AAC AGC CTG AGA GCT GAG GAC

CDR3
                              ------------------------------------------------
      T   A   V   Y   Y   C   A   R   E   G   P   Y   S   N   Y   L   D   Y
271   ACG GCT GTG TAT TAC TGT GCG AGA GAG GGC CCT TAC AGT AAC TAC CTT GAC TAC
                                                         |
                                                         └──► JH4b

W   G   Q   G   T   L   V   T   V   S   S
325   TGG GGC CAG GGA ACC CTG GTC ACC GTC TCC TCA
```

Figure 2A

Anti-CD70 10B4 VK Regions

V segment:    L18
J segment:    JK3

```
      A   I   Q   L   T   Q   S   P   S   S   L   S   A   S   V   G   D   R
  1   GCC ATC CAG TTG ACC CAG TCT CCA TCC TCC CTG TCT GCA TCT GTA GGA GAC AGA
                                            CDR1
                                  ---------------------------------------------
      V   T   I   T   C   R   A   S   Q   G   I   S   S   A   L   A   W   Y
 55   GTC ACC ATC ACT TGC CGG GCA AGT CAG GGC ATT AGC AGT GCT TTA GCC TGG TAT
                                                                CDR2
                                                           --------------------
      Q   Q   K   P   G   K   A   P   K   F   L   I   Y   D   A   S   S   L
109   CAG CAG AAA CCA GGG AAA GCT CCT AAG TTC TTG ATC TAT GAT GCC TCC AGT TTG

CDR2
      --------
      E   S   G   V   P   S   R   F   S   G   S   G   S   G   T   D   F   T
163   GAA AGT GGG GTC CCA TCA AGG TTC AGC GGC AGT GGA TCT GGG ACA GAT TTC ACT
                                                                        CDR3
                                                                   --------
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGT CAA CAG

CDR3
      ------------------------------------
      F   N   S   Y   P   F   T   F   G   P   G   T   K   V   D   I   K
271   TTT AAT AGT TAC CCA TTC ACT TTC GGC CCT GGG ACC AAA GTG GAT ATC AAA
```

Figure 2B

Anti-CD70 8B5 VH Regions

V segment:     3-33
D segment:           3-10
J segment:     JH4b

```
      Q   V   Q   L   V   E   S   G   G   G   V   V   Q   P   G   R   S   L
  1   CAG GTG CAG CTG GTG GAG TCT GGG GGA GGC GTG GTC CAG CCT GGG AGG TCC CTG

CDR1
                                                      -----------------------
      R   L   S   C   A   T   S   G   F   T   F   S   D   Y   G   M   H   W
 55   AGA CTC TCC TGT GCG ACG TCT GGA TTC ACC TTC AGT GAC TAT GGC ATG CAC TGG

CDR2
                                                              -----------------
      V   R   Q   A   P   G   K   G   L   E   W   V   A   V   I   W   Y   D
109   GTC CGC CAG GCT CCA GGC AAG GGG CTG GAG TGG GTG GCA GTT ATA TGG TAT GAT

CDR2
  --------------------------------------------------
      G   S   N   K   Y   Y   A   D   S   V   K   G   R   F   T   I   S   R
163   GGA AGT AAT AAA TAC TAT GCA GAC TCC GTG AAG GGC CGA TTC ACC ATC TCC AGA

D   N   S   K   K   T   L   S   L   Q   M   N   S   L   R   A   E   D
217   GAC AAT TCC AAG AAA ACG CTG TCT CTG CAA ATG AAC AGC CTG AGA GCC GAG GAC

CDR3
                              ----------------------------------------------
      T   A   V   Y   Y   C   A   R   D   S   I   M   V   R   G   D   Y   W
271   ACG GCT GTG TAT TAC TGT GCG AGA GAT TCT ATT ATG GTT CGG GGG GAC TAC TGG
                                                              └──→ JH4b

G   Q   G   T   L   V   T   V   S   S
325   GGC CAG GGA ACC CTG GTC ACC GTC TCC TCA
```

Figure 3A

Anti-CD70 8B5 VK Regions

V segment:    L15
J segment:    JK4

```
      D   I   Q   M   T   Q   S   P   S   S   L   S   A   S   V   G   D   R
  1   GAC ATC CAG ATG ACC CAG TCT CCA TCC TCA CTG TCT GCA TCT GTA GGA GAC AGA
                                          CDR1
                                  ------------------------------------------
      V   T   I   T   C   R   A   S   Q   G   I   S   S   W   L   A   W   Y
 55   GTC ACC ATC ACT TGT CGG GCG AGT CAG GGT ATT AGC AGC TGG TTA GCC TGG TAT
                                                                  CDR2
                                                          --------------------
      Q   Q   K   P   E   K   A   P   K   S   L   I   Y   A   A   S   S   L
109   CAG CAG AAA CCA GAG AAA GCC CCT AAG TCC CTG ATC TAT GCT GCA TCC AGT TTG

CDR2
      -------
      Q   S   G   V   P   S   R   F   S   G   S   G   S   G   T   D   F   T
163   CAA AGT GGG GTC CCA TCA AGG TTC AGC GGC AGT GGA TCT GGG ACA GAT TTC ACT
                                                                      CDR3
                                                                      -------
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGC CAA CAG

CDR3
      ---------------------------------
      Y   N   S   Y   P   L   T   F   G   G   G   T   K   V   E   I   K
271   TAT AAT AGT TAC CCG CTC ACT TTC GGC GGA GGG ACC AAG GTG GAG ATC AAA
```

Figure 3B

Anti-CD70 18E7 VH Regions

```
V segment:      3-33
D segment:          3-10
J segment:      JH4b
```

```
      Q   V   Q   L   V   E   S   G   G   V   V   Q   P   G   R   S   L
   1  CAG GTG CAG CTG GTG GAG TCT GGG GGA GGC GTG GTC CAG CCT GGG AGG TCC CTG

CDR1
                                                ----------------------
      R   L   S   C   A   A   S   G   F   T   F   S   D   H   G   M   H   W
  55  AGA CTC TCC TGT GCA GCG TCT GGA TTC ACC TTC AGC GAC CAT GGC ATG CAC TGG

CDR2
                                                          ----------------------
      V   R   Q   A   P   G   K   G   L   E   W   V   A   V   I   W   Y   D
 109  GTC CGC CAG GCT CCA GGC AAG GGG CTG GAG TGG GTG GCA GTT ATA TGG TAT GAT

CDR2
      ----------------------------------------------------
      G   S   N   K   Y   Y   A   D   S   V   K   G   R   F   T   I   S   R
 163  GGA AGT AAT AAA TAC TAT GCA GAC TCC GTG AAG GGC CGA TTC ACC ATC TCC AGA

D   N   S   K   N   T   L   Y   L   Q   M   N   S   L   R   A   E   D
 217  GAC AAT TCC AAG AAC ACG CTG TAT CTG CAA ATG AAC AGC CTG AGA GCC GAG GAC

CDR3
                                ----------------------------------------
      T   A   V   Y   Y   C   A   R   D   S   I   M   V   R   G   D   Y   W
 271  ACG GCT GTG TAT TAC TGT GCG AGA GAT TCT ATT ATG GTT CGG GGG GAC TAC TGG
                                                              └→
                                                               JH4b

G   Q   G   T   L   V   T   V   S   S
 325  GGC CAG GGA ACC CTG GTC ACC GTC TCC TCA
```

Figure 4A

Anti-CD70 18E7 VK Regions

V segment:   L15
J segment:   JK4

```
        D   I   Q   M   T   Q   S   P   S   S   L   S   A   S   V   G   D   R
  1    GAC ATC CAG ATG ACC CAG TCT CCA TCC TCA CTG TCT GCA TCT GTA GGA GAC AGA
                                              CDR1
                              ------------------------------------------------
        V   T   I   T   C   R   A   S   Q   G   I   S   S   W   L   A   W   Y
 55    GTC ACC ATC ACT TGT CGG GCG AGT CAG GGT ATT AGC AGC TGG TTA GCC TGG TAT
                                                                      CDR2
                                                              ------------------
        Q   Q   K   P   E   K   A   P   K   S   L   I   Y   A   A   S   S   L
109    CAG CAG AAA CCA GAG AAA GCC CCT AAG TCC CTG ATC TAT GCT GCA TCC AGT TTG
       CDR2
       --------
        Q   S   G   V   P   S   R   F   S   G   S   G   S   G   T   D   F   T
163    CAA AGT GGG GTC CCA TCA AGG TTC AGC GGC AGT GGA TCT GGG ACA GAT TTC ACT
                                                                              CDR3
                                                                              --------
        L   T   I   S   S   L   Q   P   E   D   F   A   T   Y   Y   C   Q   Q
217    CTC ACC ATC AGC AGC CTG CAG CCT GAA GAT TTT GCA ACT TAT TAC TGC CAA CAG

CDR3
       ------------------------------
        Y   N   S   Y   P   L   T   F   G   G   G   T   K   V   E   I   K
271    TAT AAT AGT TAC CCG CTC ACT TTC GGC GGA GGG ACC AAG GTG GAG ATC AAA
```

Figure 4B

Anti-CD70 69A7 VH

V segment:    4-61
    D segment:    4-23
    J segment:    JH4b

```
        Q   V   Q   L   Q   E   S   G   P   G   L   V   K   P   S   E   T   L
1       CAG GTG CAG CTG CAG GAG TCG GGC CCA GGA CTG GTG AAG CCT TCG GAG ACC CTG

CDR1
                                                                    ~~~~~~~~~~~~~~~~~~~~~~
        S   L   T   C   T   V   S   G   G   S   V   S   S   D   Y   Y   Y   W
55      TCC CTC ACC TGC ACT GTC TCT GGT GGC TCC GTC AGC AGT GAT TAT TAC TAC TGG

CDR1                                                        CDR2
        ~~~                                                         ~~~~~~~~~~~~
        S   W   I   R   Q   P   P   G   K   G   L   E   W   L   G   Y   I   Y
109     AGC TGG ATC CGG CAG CCC CCA GGG AAG GGA CTG GAG TGG CTT GGG TAT ATC TAT

CDR2
        ~~~~~~~~~~~~~~~~~~~~~~~~~~~~~~~~~~~~~~~~~~~~~~~~~~~~~~~~~~~~
        Y   S   G   S   T   N   Y   N   P   S   L   K   S   R   V   T   I   S
163     TAC AGT GGG AGC ACC AAC TAC AAC CCC TCC CTC AAG AGT CGA GTC ACC ATA TCA

V   D   T   S   K   N   Q   F   S   L   K   L   R   S   V   T   T   A
217     GTA GAC ACG TCC AAG AAC CAG TTC TCC CTG AAG CTG AGG TCT GTG ACC ACT GCG

CDR3
                                                                    ~~~~~~~~~~~~~~~~~~~~~~~~~~~~
        D   T   A   V   Y   Y   C   A   R   G   D   G   D   Y   G   G   N   C
271     GAC ACG GCC GTG TAT TAC TGT GCG AGA GGG GAT GGG GAC TAC GGT GGT AAC TGT

CDR3
        ~~~~~~~~~~~
        F   D   Y   W   G   Q   G   T   L   V   T   V   S   S
325     TTT GAC TAC TGG GGC CAG GGA ACC CTG GTC ACC GTC TCC TCA
```

Figure 5A

Anti-CD70 69A7 VK

V segment:     L6
    J segment:     JK4

```
          E   I   V   L   T   Q   S   P   A   T   L   S   L   S   P   G   E   R
1         GAA ATT GTG TTG ACA CAG TCT CCA GCC ACC CTG TCT TTG TCT CCA GGG AAA AGA
                                                  CDR1
                                      ~~~~~~~~~~~~~~~~~~~~~~~~~~~~~~~~~~~~~~~~~~
          A   T   L   S   C   R   A   S   Q   S   V   S   S   Y   L   A   W   Y
55        GCC ACC CTC TCC TGC AGG GCC AGT CAG AGT GTT AGC AGC TAC TTA GCC TGG TAC
                                                                      CDR2
                                                              ~~~~~~~~~~~~~~~~~~
          Q   Q   K   P   G   Q   A   P   R   L   L   I   F   D   A   S   N   R
109       CAA CAG AAA CCT GGC CAG GCT CCC AGG CTC CTC ATC TTT GAT GCA TCC AAC AGG

CDR2
          ~~~~~~~~
          A   T   G   I   P   A   R   F   S   G   S   G   S   G   T   D   F   T
163       GCC ACT GGC ATC CCA GCC AGG TTC AGT GGC AGT GGG TCT GGG ACA GAC TTC ACT
                                                                              CDR3
                                                                          ~~~~~~~~
          L   T   I   S   S   L   E   P   E   D   F   A   V   Y   Y   C   Q   Q
217       CTC ACC ATC AGC AGC CTA GAG CCT GAA GAT TTT GCA GTT TAT TAC TGT CAG CAA
              CDR3
          ~~~~~~~~~~~~~~~~~~~~~~~~~~~~~~~~
          R   S   N   W   P   L   T   F   G   G   G   T   K   V   E   I   K
271       CGT AGC AAC TGG CCG CTC ACT TTC GGC GGA GGG ACC AAG GTG GAG ATC AAA
```

Figure 5B

Anti-CD70 2H5 and 10B4 V_H Regions

```
                                                             CDR1
3-30.3 Germline:  Q V Q L V E S G G G V V Q P G R S L R L S C A A S G F T F S S Y A M H W V R Q
2H5 VH:           - - - - - - - - - - - - - - - - - - - - - - - - - - - - - I - - - - - - - -
10B4 VH:          - - I - - - - - - - - - - - - - - - - - - - - - - - - - - G Y - - - - - - - -

CDR2
3-30.3 Germline:  A P G K G L E W V A V I S Y D G S N K Y Y A D S V K G R F T I S R D N S K N T
2H5 VH:           - - - - - - - - - - - - - - - - - R - - - - - - - - - - - - - - - - - - - -
10B4 VH:          - - - - - - - - - - - - - - - - - - I - - - - - - - - - - - - - - - - - - -

CDR3
3-30.3 Germline:  L Y L Q M N S L R A E D T A V Y Y C A R
JH4b Germline:                                                            Y F D Y W G Q G T L
2H5 VH:           - - - - - - - - - - - - - - - - - - -   - - D T D G Y D - - - - - - - - - -
10B4 VH:          - - - - - - - - - - - - - - - - - - -   - - E G P Y S N - L - - - - - - - -

JH4b Germline:    V T V S S
2H5 VH:           - - - - -   (JH4b)
10B4 VH:          - - - - -   (JH4b)
```

Figure 6

Anti-CD70 8B5 and 18E7 V_H regions

```
                                                         CDR1
3-33 Germline: Q V Q L V E S G G G V V Q P G R S L R L S C A A S G F T F S S Y G M H W V R Q
8B5 VH:        - - - - - - - - - - - - - - - - - - - - - - - - T - - - - D - - - - - - - -
18E7 VH:       - - - - - - - - - - - - - - - - - - - - - - - - - - - - - D - - - - - - D H CDR2
3-33 Germline: A P G K G L E W V A V I W Y D G S N K Y Y A D S V K G R F T I S R D N S K N T
8B5 VH:        - - - - - - - - - - - - - - - - - - - - - - - - - - - - - - - - - - - - - -
18E7 VH:       - - - - - - - - - - - - - - - - - - - - - - - - - - - - - - - - - - - - - K CDR3
3-33 Germline: L Y L Q M N S L R A E D T A V Y Y C A R
JH4b Germline:                                                          D Y W G Q G T L V T V S S
D 3-10 Germline:                                        M V R G
8B5 VH:        - - - - - - - - - - - - - - - - - - -                    D Y W G Q G T L V T V S S
18E7 VH:       - S - - - - - - - - - - - - - - - - -    - - - D S I     D Y W G Q G T L V T V S S
                                                                        (JH4b)
```

Figure 7

Anti-CD70 69A7 VH region

```
                                                      CDR1
4-61 germline  Q V Q L Q E S G P G L V K P S E T L S L T C T V S G G S V S S G S Y Y W
69A7 VH        - - - - - - - - - - - - - - - - - - - - - - - - - - - - - - - D Y - -

CDR2
4-61 germline  S W I R Q P P G K G L E W I G Y I Y Y S G S T N Y N P S L K S R V T I S
69A7 VH        - S - - - - - - - - - - - L - - - - - - - - - - - - - - - - - - - - -

CDR3
4-61 germline  V D T S K N Q F S L K L S S V T A A D T A V Y Y C A R
JH4b germline                                                                         Y
69A7 VH        - - - - - - - - - - - - - - - - - - - - - - - - - -   - G D G D Y G G N C JH4b germline  F D Y W G Q G T L V T V S S   (JH4b)
69A7 VH        - - - - - - - - - - - - - -
```

Figure 8

Anti-CD70 mAb1 2H5 VK Region

```
                      CDR1
L6 Germline:   E I V L T Q S P A T L S L S P G E R A T L S C R A S Q S V S S Y L A
2H5 VK #1:     - - - - - - - - - - - - - - - - - - - - - - - - - - - - - - - - -

CDR2
L6 Germline:   W Y Q Q K P G Q A P R L L I Y D A S N R A T G I P A R F S G S G S G
2H5 VK #1:     - - - - - - - - - - - - - - - - - - - - - - - - - - - - - - - - -

CDR3
L6 Germline:   T D F T L T I S S L E P E D F A V Y Y C Q Q R S N W
JK4 Germline:                                                       L T F G G G T
2H5 VK #1:     - - - - - - - - - - - - - - - - - - - - - T - - P - - - - - - - -

JK4 Germline:  K V E I K
2H5 VK #1:     - - - - -   (JK4)
```

Figure 9

*Anti-CD70 mAb3 10B4 VK Regions*

```
                                                                                 CDR1
L18 Germline:  A I Q L T Q S P S S L S A S V G D R V T I T C R A S Q G I S S A L A
10B4 VK:       - - - - - - - - - - - - - - - - - - - - - - - - - - - - - - - - -

CDR2
L18 Germline:  W Y Q Q K P G K A P K L L I Y D A S S L E S G V P S R F S G S G S G
10B4 VK:       - - - - - - - - - - - - F - - - - - - - - - - - - - - - - - - - -

CDR3
L18 Germline:  T D F T L T I S S L Q P E D F A T Y Y C Q Q F N S Y P
JK3 Germline:                                                       F T F G P G T
10B4 VK:       - - - - - - - - - - . - - - - - - - - - - - - - - -  - - - - - - -

JK3 Germline:  K V D I K   (JK3)
10B4 VK:       - - - - -
```

Figure 10

Anti-CD70 8B5 and 18E7 VK Regions

```
                    CDR1
L15 Germline:  D I Q M T Q S P S S L S A S V G D R V T I T C R A S Q G I S S W L A
8B5   VK:      - - - - - - - - - - - - - - - - - - - - - - - - - - - - - - - - -
18E7  VK #1:   - - - - - - - - - - - - - - - - - - - - - - - - - - - - - - - - -

CDR2
L15 Germline:  W Y Q Q K P E K A P K S L I Y A A S S L Q S G V P S R F S G S G S G
8B5   VK:      - - - - - - - - - - - - - - - - - - - - - - - - - - - - - - - - -
18E7  VK #1:   - - - - - - - - - - - - - - - - - - - - - - - - - - - - - - - - -

CDR3
L15 Germline:  T D F T L T I S S L Q P E D F A T Y Y C Q Q Y N S Y P
JK4 Germline:                                                       L T F G G G
8B5   VK:      - - - - - - - - - - - - - - - - - - - - - - - - - -  - - - - - -
18E7  VK #1:   - - - - - - - - - - - - - - - - - - - - - - - - - -  - - - - - -

JK4 Germline:  T K V E I K
8B5   VK:      - - - - - -   (JK4)
18E7  VK #1:   - - - - - -   (JK4)
```

Figure 11

Anti-CD70 69A7 VK region

```
                                                        CDR1
L6 germline    E I V L T Q S P A T L S L S P G E R A T L S C R A S Q S V S S -
69A7 VK        - - - - - - - - - - - - - - - - - - - - - - - - - - - - - - - -

CDR2
L6 germline    Y L A W Y Q Q K P G Q A P R L L I Y D A S N R A T G I P A R F -
69A7 VK        - - - - - - - - - - - - - - - - - - F - - - - - - - - - - - - -

CDR3
L6 germline    S G S G S G T D F T L T I S S L E P E D F A V Y Y C Q Q R S N -
69A7 VK        - - - - - - - - - - - - - - - - - - - - - - - - - - - - - - - -

L6 germline    W P
JK4 germline       L T F G G G T K V E I K     (JK4)
69A7 VK        - - - - - - - - - - - - - - -
```

Figure 12

HUMAN MONOCLONAL ANTIBODIES TO CD70

CROSS-REFERENCE TO RELATED APPLICATIONS

This application is a national phase of International Application No. PCT/US2006/037753), filed Sep. 26, 2006 which claims the benefit of U.S. Provisional Patent Application No. 60/720,600, filed Sep. 26, 2005; U.S. Provisional Patent Application No. 60/726,695, filed Oct. 13, 2005; and U.S. Provisional Patent Application No. 60/748,827, filed Dec. 8, 2005, the benefit of the earlier filing date of which is hereby claimed under 35 U.S.C. §119(e) and the entire contents of all are incorporated herein by reference.

SEQUENCE LISTING

The specification further incorporates by reference the Sequence Listing submitted herewith via EFS on Feb. 29, 2008. Pursuant to 37 C.F.R. §1.52(e)(5), the Sequence Listing text file, identified as 77375628.txt, is 38 KB and was created on Feb. 28, 2008. The Sequence Listing, electronically filed herewith, does not extend beyond the scope of the specification and thus does not contain new matter.

BACKGROUND

The cytokine receptor CD27 is a member of the tumor necrosis factor receptor (TFNR) superfamily, which play a role in cell growth and differentiation, as well as apoptosis or programmed cell death. The ligand for CD27 is CD70, which belongs to the tumor necrosis factor family of ligands. CD70 is a 193 amino acid polypeptide having a 20 amino acid hydrophilic N-terminal domain and a C-terminal domain containing 2 potential N-linked glycosylation sites (Goodwin, R. G. et al. (1993) *Cell* 73:447-56; Bowman et al. (1994) *Immunol* 152:1756-61). Based on these features, CD70 was determined to be a type II transmembrane protein having an extracellular C-terminal portion.

CD70 is transiently found on activated, but not resting T and B lymphocytes and dendritic cells (Hintzen et al. (1994) *J. Immunol.* 152:1762-1773; Oshima et al. (1998) *Int. Immunol.* 10:517-26; Tesselaar et al. (2003) *J. Immunol.* 170:33-40). In addition to expression on normal cells, CD70 expression has been reported in different types of cancers including renal cell carcinomas, metastatic breast cancers, brain tumors, leukemias, lymphomas and nasopharangeal carcinomas (Junker et al. (2005) *J Urol.* 173:2150-3; Sloan et al. (2004) *Am J Pathol.* 164:315-23; Held-Feindt and Mentlein (2002) *Int J Cancer* 98:352-6; Hishima et al. (2000) *Am J Surg Pathol.* 24:742-6; Lens et al. (1999) *Br J Haematol.* 106:491-503). Additionally, CD70 has been found to be over-expressed on T cells treated with DNA methyltransferase inhibitors or ERK pathway inhibitors, possibly leading to drug-induced and idiopathic lupus (Oelke et al. (2004) *Arthritis Rheum.* 50:1850-60). The interaction of CD70 with CD27 has also been proposed to play a role in cell-mediated autoimmune disease and the inhibition of TNF-alpha production (Nakajima et al. (2000) *J. Neuroimmunol.* 109:188-96).

Accordingly, CD70 represents a valuable target for the treatment of cancer, autoimmune disorders and a variety of other diseases characterized by CD70 expression.

SUMMARY

The present disclosure provides isolated monoclonal antibodies, in particular human monoclonal antibodies, that bind to CD70 and that exhibit numerous desirable properties. These properties include high affinity binding to human CD70. Also provided are methods for treating a variety CD70 mediated diseases using the antibodies and compositions of the instant disclosure.

In one aspect, this disclosure pertains to an isolated monoclonal antibody or an antigen-binding portion thereof, wherein the antibody (a) binds to human CD70 with a $K_D$ of $1 \times 10^{-7}$ M or less; and (b) binds to a renal cell carcinoma tumor cell line.

Preferably, the antibody binds to a renal cell carcinoma tumor cell line selected from the group consisting of 786-O (ATCC Accession No. CRL-1932), A-498 (ATCC Accession No. HTB-44), ACHN (ATCC Accession No. CRL-1611), Caki-1 (ATCC Accession No. HTB-46) and Caki-2 (ATCC Accession No. HTB-47).

Preferably the antibody is a human antibody, although in alternative embodiments the antibody can be a murine antibody, a chimeric antibody or a humanized antibody.

In more preferred embodiments, the antibody binds to human CD70 with a $K_D$ of $5.5 \times 10^{-9}$ M or less or binds to human CD70 with a $K_D$ of $3 \times 10^{-9}$ M or less or binds to human CD70 with a $K_D$ of $2 \times 10^{-9}$ M or less or binds to human CD70 with a $K_D$ of $1.5 \times 10^{-9}$ M or less.

In another embodiment, the antibody is internalized by 786-O renal cell carcinoma tumor cells after binding to CD70 expressed on those cells.

In another embodiment, the antibody binds to a B-cell tumor cell line. Preferably, the B-cell tumor cell line is selected from the group consisting of Daudi (ATCC Accession No. CCL-213), HuT 78 (ATCC Accession No. TIB-161), Raji (ATCC Accession No. CCL-86) and Granta-519 (DSMZ Accession No. 342).

In another embodiment, this disclosure provides an isolated monoclonal antibody or antigen binding portion thereof, wherein the antibody cross-competes for binding to CD70 with a reference antibody, wherein the reference antibody: (a) binds to human CD70 with a $K_D$ of $1 \times 10^{-7}$ M or less; and (b) binds to a renal cell carcinoma tumor cell line. In various embodiments, the reference antibody comprises:
  (a) a heavy chain variable region comprising the amino acid sequence of SEQ ID NO:1; and
  (b) a light chain variable region comprising the amino acid sequence of SEQ ID NO:6;
or the reference antibody comprises:
  (a) a heavy chain variable region comprising the amino acid sequence of SEQ ID NO:2; and
  (b) a light chain variable region comprising the amino acid sequence of SEQ ID NO:7;
or the reference antibody comprises:
  (a) a heavy chain variable region comprising the amino acid sequence of SEQ ID NO:3; and
  (b) a light chain variable region comprising the amino acid sequence of SEQ ID NO:8
or the reference antibody comprises:
  (a) a heavy chain variable region comprising the amino acid sequence of SEQ ID NO:4; and
  (b) a light chain variable region comprising the amino acid sequence of SEQ ID NO:9
or the reference antibody comprises:
  (a) a heavy chain variable region comprising the amino acid sequence of SEQ ID NO:5; and
  (b) a light chain variable region comprising the amino acid sequence of SEQ ID NO:10.

In one aspect, this disclosure pertains to an isolated monoclonal antibody or an antigen-binding portion thereof, comprising a heavy chain variable region that is the product of or derived from a human $V_H3$-30.3 gene, wherein the antibody specifically binds CD70. This disclosure also provides an isolated monoclonal antibody or an antigen-binding portion thereof, comprising a heavy chain variable region that is the product of or derived from a human $V_H3$-33 gene, wherein the antibody specifically binds CD70. This disclosure also provides an isolated monoclonal antibody or an antigen-binding portion thereof, comprising a heavy chain variable region that is the product of or derived from a human $V_H4$-61 gene, wherein the antibody specifically binds CD70. This disclosure still further provides an isolated monoclonal antibody or an antigen-binding portion thereof, comprising a light chain variable region that is the product of or derived from a human $V_K L6$ gene, wherein the antibody specifically binds CD70. This disclosure still further provides an isolated monoclonal antibody or an antigen-binding portion thereof, comprising a light chain variable region that is the product of or derived from a human $V_K L18$ gene, wherein the antibody specifically binds CD70. This disclosure further provides an isolated monoclonal antibody or an antigen-binding portion thereof, comprising a light chain variable region that is the product of or derived from a human $V_K L15$ gene, wherein the antibody specifically binds to CD70.

A preferred combination comprises:
- (a) a heavy chain variable region CDR1 comprising SEQ ID NO:11;
- (b) a heavy chain variable region CDR2 comprising SEQ ID NO:16;
- (c) a heavy chain variable region CDR3 comprising SEQ ID NO:21;
- (d) a light chain variable region CDR1 comprising SEQ ID NO:26;
- (e) a light chain variable region CDR2 comprising SEQ ID NO:31; and
- (f) a light chain variable region CDR3 comprising SEQ ID NO:36.

Another preferred combination comprises:
- (a) a heavy chain variable region CDR1 comprising SEQ ID NO:12;
- (b) a heavy chain variable region CDR2 comprising SEQ ID NO:17;
- (c) a heavy chain variable region CDR3 comprising SEQ ID NO:22;
- (d) a light chain variable region CDR1 comprising SEQ ID NO:27;
- (e) a light chain variable region CDR2 comprising SEQ ID NO:32; and
- (f) a light chain variable region CDR3 comprising SEQ ID NO:37.

Another preferred combination comprises:
- (a) a heavy chain variable region CDR1 comprising SEQ ID NO:13;
- (b) a heavy chain variable region CDR2 comprising SEQ ID NO:18;
- (c) a heavy chain variable region CDR3 comprising SEQ ID NO:23;
- (d) a light chain variable region CDR1 comprising SEQ ID NO:28;
- (e) a light chain variable region CDR2 comprising SEQ ID NO:33; and
- (f) a light chain variable region CDR3 comprising SEQ ID NO:38.

Another preferred combination comprises:
- (a) a heavy chain variable region CDR1 comprising SEQ ID NO:14;
- (b) a heavy chain variable region CDR2 comprising SEQ ID NO:19;
- (c) a heavy chain variable region CDR3 comprising SEQ ID NO:24;
- (d) a light chain variable region CDR1 comprising SEQ ID NO:29;
- (e) a light chain variable region CDR2 comprising SEQ ID NO:34; and
- (t) a light chain variable region CDR3 comprising SEQ ID NO:39.

Another preferred combination comprises:
- (a) a heavy chain variable region CDR1 comprising SEQ ID NO:15;
- (b) a heavy chain variable region CDR2 comprising SEQ ID NO:20;
- (c) a heavy chain variable region CDR3 comprising SEQ ID NO:25;
- (d) a light chain variable region CDR1 comprising SEQ ID NO:30;
- (e) a light chain variable region CDR2 comprising SEQ ID NO:35; and
- (f) a light chain variable region CDR3 comprising SEQ ID NO:40.

Other preferred antibodies of the disclosure or antigen binding portions thereof comprise:
- (a) a heavy chain variable region comprising the amino acid sequence of SEQ ID NO:1; and
- (b) a light chain variable region comprising the amino acid sequence of SEQ ID NO:6.

Another preferred combination comprises:
- (a) a heavy chain variable region comprising the amino acid sequence of SEQ ID NO:2; and
- (b) a light chain variable region comprising the amino acid sequence of SEQ ID NO:7.

Another preferred combination comprises:
- (a) a heavy chain variable region comprising the amino acid sequence of SEQ ID NO:3; and
- (b) a light chain variable region comprising the amino acid sequence of SEQ ID NO:8.

Another preferred combination comprises:
- (a) a heavy chain variable region comprising the amino acid sequence of SEQ ID NO:4; and
- (b) a light chain variable region comprising the amino acid sequence of SEQ ID NO:9.

Another preferred combination comprises:
- (a) a heavy chain variable region comprising the amino acid sequence of SEQ ID NO:5; and
- (b) a light chain variable region comprising the amino acid sequence of SEQ ID NO:10.

The antibodies of the disclosure can be, for example, full-length antibodies, for example of an IgG1 or IgG4 isotype. Alternatively, the antibodies can be antibody fragments, such as Fab or Fab'$_2$ fragments or single chain antibodies.

The disclosure also provides an immunoconjugate comprising an antibody of the disclosure or antigen-binding portion thereof, linked to a therapeutic agent, such as a cytotoxin or a radioactive isotope. The disclosure also provides a bispecific molecule comprising an antibody or antigen-binding portion thereof, of the disclosure, linked to a second functional moiety having a different binding specificity than said antibody or antigen binding portion thereof.

Compositions comprising an antibody or antigen-binding portion thereof or immunoconjugate or bispecific molecule of the disclosure and a pharmaceutically acceptable carrier are also provided.

Nucleic acid molecules encoding the antibodies or antigen-binding portions thereof, of the disclosure are also encompassed by the disclosure, as well as expression vectors comprising such nucleic acids, host cells comprising such expression vectors and methods for making anti-CD70 antibodies using such host cells. Moreover, the disclosure provides a transgenic mouse comprising human immunoglobulin heavy and light chain transgenes, wherein the mouse expresses an antibody of the disclosure, as well as hybridomas prepared from such a mouse, wherein the hybridoma produces the antibody of the disclosure.

In yet another aspect, the disclosure provides a method of treating or preventing a disease characterized by growth of tumor cells expressing CD70, comprising administering to a subject an anti-CD70 human antibody of the present disclosure in an amount effective to treat or prevent the disease. The disease can be a cancer, e.g., renal cell carcinoma cancer or lymphoma.

In yet another aspect, the disclosure provides a method of treating an autoimmune disorder, comprising administering to a subject an anti-CD70 human antibody of the present disclosure in an amount effective to treat the autoimmune disorder.

Other features and advantages of the instant disclosure will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1B shows the nucleotide sequence (SEQ ID NO:46) and amino acid sequence (SEQ ID NO:6) of the light chain variable region of the 2H5 human monoclonal antibody. The CDR1 (SEQ ID NO:26), CDR2 (SEQ ID NO:31) and CDR3 (SEQ ID NO:36) regions are delineated and the V and J germline derivations are indicated.

FIG. 2A shows the nucleotide sequence (SEQ ID NO:42) and amino acid sequence (SEQ ID NO:2) of the heavy chain variable region of the 10B4 human monoclonal antibody. The CDR1 (SEQ ID NO:12), CDR2 (SEQ ID NO:17) and CDR3 (SEQ ID NO:22) regions are delineated and the V, D, and J germline derivations are indicated.

FIG. 2B shows the nucleotide sequence (SEQ ID NO:47) and amino acid sequence (SEQ ID NO:7) of the light chain variable region of the 10B4 human monoclonal antibody. The CDR1 (SEQ ID NO:27), CDR2 (SEQ ID NO:32) and CDR3 (SEQ ID NO:37) regions are delineated and the V and J germline derivations are indicated.

FIG. 3A shows the nucleotide sequence (SEQ ID NO:43) and amino acid sequence (SEQ ID NO:3) of the heavy chain variable region of the 8B5 human monoclonal antibody. The CDR1 (SEQ ID NO:13), CDR2 (SEQ ID NO:18) and CDR3 (SEQ ID NO:23) regions are delineated and the V, D and J germline derivations are indicated.

FIG. 3B shows the nucleotide sequence (SEQ ID NO:48) and amino acid sequence (SEQ ID NO:8) of the light chain variable region of the 8B5 human monoclonal antibody. The CDR1 (SEQ ID NO:28), CDR2 (SEQ ID NO:33) and CDR3 (SEQ ID NO:38) regions are delineated and the V and J germline derivations are indicated.

FIG. 4A shows the nucleotide sequence (SEQ ID NO:44) and amino acid sequence (SEQ ID NO:4) of the heavy chain variable region of the 18E7 human monoclonal antibody. The CDR1 (SEQ ID NO:14), CDR2 (SEQ ID NO:19) and CDR3 (SEQ ID NO:24) regions are delineated and the V, D and J germline derivations are indicated.

FIG. 4B shows the nucleotide sequence (SEQ ID NO:49) and amino acid sequence (SEQ ID NO:9) of the light chain variable region of the 18E7 human monoclonal antibody. The CDR1 (SEQ ID NO:29), CDR2 (SEQ ID NO:34) and CDR3 (SEQ ID NO:39) regions are delineated and the V and J germline derivations are indicated.

FIG. 5A shows the nucleotide sequence (SEQ ID NO:45) and amino acid sequence (SEQ ID NO:5) of the heavy chain variable region of the 69A7 human monoclonal antibody. The CDR1 (SEQ ID NO:15), CDR2 (SEQ ID NO:20) and CDR3 (SEQ ID NO:25) regions are delineated and the V, D and J germline derivations are indicated.

FIG. 5B shows the nucleotide sequence (SEQ ID NO:50) and amino acid sequence (SEQ ID NO:10) of the light chain variable region of the 69A7 human monoclonal antibody. The CDR1 (SEQ ID NO:30), CDR2 (SEQ ID NO:35) and CDR3 (SEQ ID NO:40) regions are delineated and the V and J germline derivations are indicated.

FIG. 6 shows the alignment of the amino acid sequence of the heavy chain variable region of 2H5 and 10B4 with the human germline $V_H$3-30.3 amino acid sequence (SEQ ID NO:51).

FIG. 7 shows the alignment of the amino acid sequence of the heavy chain variable region of 8B5 and 18E7 with the human germline $V_H$3-33 amino acid sequence (SEQ ID NO:52).

FIG. 8 shows the alignment of the amino acid sequence of the heavy chain variable region of 69A7 with the human germline $V_H$4-61 amino acid sequence (SEQ ID NO:53).

FIG. 9 shows the alignment of the amino acid sequence of the light chain variable region of 2H5 with the human germline $V_k$ L6 amino acid sequence (SEQ ID NO:54).

FIG. 10 shows the alignment of the amino acid sequence of the light chain variable region of 10B4 with the human germline $V_k$ L18 amino acid sequence (SEQ ID NO:55).

FIG. 11 shows the alignment of the amino acid sequence of the light chain variable region of 8B5 and 18E7 with the human germline $V_k$ L15 amino acid sequence (SEQ ID NO:56).

FIG. 12 shows the alignment of the amino acid sequence of the light chain variable region of 69A7 with the human germline $V_k$ L6 amino acid sequence (SEQ ID NO:54).

DETAILED DESCRIPTION

Figure 1A:
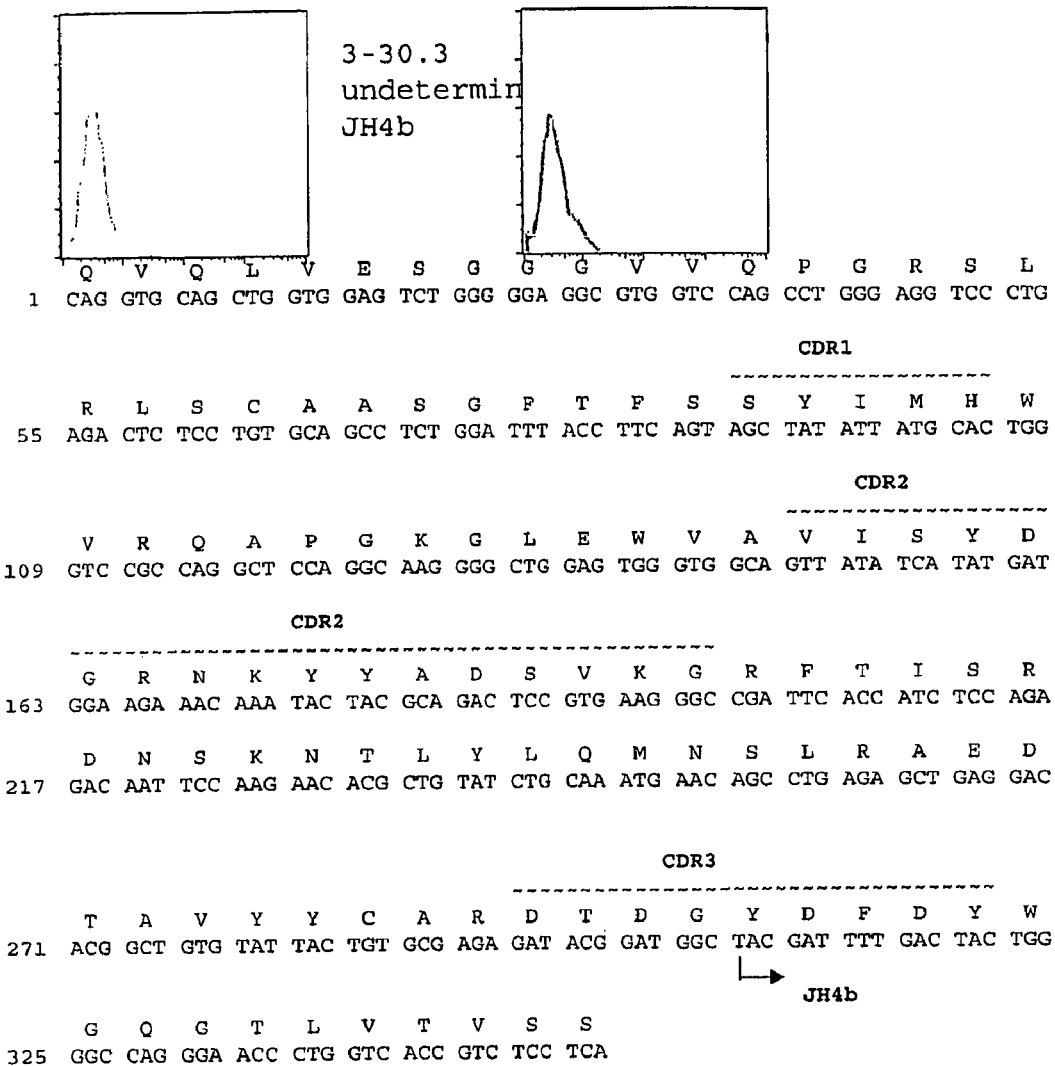
FIG. 1A shows the nucleotide sequence (SEQ ID NO:41) and amino acid sequence (SEQ ID NO:1) of the heavy chain variable region of the 2H5 human monoclonal antibody. The CDR1 (SEQ ID NO:11), CDR2 (SEQ ID NO:16) and CDR3 (SEQ ID NO:21) regions are delineated and the V and J germline derivations are indicated.

The present disclosure relates to isolated monoclonal antibodies, particularly human monoclonal antibodies, that bind specifically to CD70 with high affinity. In certain embodiments, the antibodies of the disclosure are derived from particular heavy and light chain germline sequences and/or comprise particular structural features such as CDR regions comprising particular amino acid sequences. This disclosure provides isolated antibodies, methods of making such antibodies, immunoconjugates and bispecific molecules comprising such antibodies and pharmaceutical compositions containing the antibodies, immunconjugates or bispecific molecules of the disclosure. This disclosure also relates to methods of using the antibodies, such as to treat diseases such as cancer.

In order that the present disclosure may be more readily understood, certain terms are defined. Additional definitions are set forth throughout the detailed description.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the CD70 receptor.

The term "antibody" as referred to herein includes whole antibodies and any antigen binding fragment (i.e., "antigen-binding portion") or single chains thereof. An "antibody" refers to a glycoprotein comprising at least two heavy (H)

chains and two light (L) chains inter-connected by disulfide bonds or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or "antibody portion"), as used herein, refers to one or more fragments of an antibody that retain the ability to specifically bind to an antigen (e.g., CD70). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, Fundamental Immunology (Paul ed., 3$^{rd}$ ed. 1993); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; and (vii) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds CD70 is substantially free of antibodies that specifically bind antigens other than CD70). An isolated antibody that specifically binds CD70 may, however, have cross-reactivity to other antigens, such as CD70 molecules from other species. In certain embodiments, an isolated antibody specifically binds to human CD70 and does not cross-react with other non-human CD70 antigens. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies may include later modifications, including natural or synthetic modifications. The human antibodies of the disclosure may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human CD70" is intended to refer to an antibody that binds to human CD70 with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-7}$ M or less, more preferably $10^{-8}$ M or less, more preferably $10^{-9}$ M or less, and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, fish, reptiles, etc.

Various aspects of the disclosure are described in further detail in the following subsections.

Anti-CD70 Antibodies

The antibodies of the disclosure are characterized by particular functional features or properties of the antibodies. For example, the antibodies bind specifically to human CD70. Preferably, an antibody of the disclosure binds to CD70 with high affinity, for example with a $K_D$ of $5\times10^{-7}$ M or less, even more preferably $5.5\times10^{-9}$ or less, even more preferably $3\times10^{-9}$ or less, even more preferably $2\times10^{-9}$ or less or even more preferably $1.5\times10^{-9}$ or less. Standard assays to evaluate the binding ability of the antibodies toward CD70 are known in the art, including for example, ELISAs, Western blots and RIAs. Suitable assays are described in detail in the Examples. The binding kinetics (e.g., binding affinity) of the antibodies also can be assessed by standard assays known in the art, such as by ELISA, Scatchard and Biacore analysis. As another example, the antibodies of the present disclosure may bind to a renal carcinoma tumor cell line, for example, the 786-O, A-498, ACHN, Caki-1 or Caki-2 cell lines. As yet another example, the antibodies of the present disclosure may bind to a B-cell tumor cell line, for example, the Daudi, HuT 78, Raji or Granta-519 cell lines.

Monoclonal Antibodies 2H5, 10B4, 8B5, 18E7 and 69A7

Exemplified antibodies of the disclosure include the human monoclonal antibodies 2H5, 10B4, 8B5, 18E7 and 69A7, isolated and structurally characterized as described in Examples 1 and 2. The $V_H$ amino acid sequences of 2H5, 10B4, 8B5, 18E7 and 69A7 are shown in SEQ ID NOs:1, 2, 3, 4 and 5, respectively. The $V_L$ amino acid sequences of 2H5, 10B4, 8B5, 18E7 and 69A7 are shown in SEQ ID NOs:6, 7, 8, 9 and 10, respectively.

Given that each of these antibodies can bind to CD70, the $V_H$ and $V_L$ sequences can be "mixed and matched" to create other anti-CD70 binding molecules of the disclosure. CD70 binding of such "mixed and matched" antibodies can be tested using the binding assays described above and in the Examples (e.g., FACS or ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the disclosure provides an isolated monoclonal antibody or antigen binding portion thereof comprising:

(a) a heavy chain variable region comprising an amino acid sequence selected from the group consisting of SEQ ID NOs: 1, 2, 3, 4 and 5; and (b) a light chain variable region comprising an amino acid sequence selected from the group consisting of SEQ ID NOs: 6, 7, 8, 9 and 10;

wherein the antibody specifically binds to CD70.

Preferred heavy and light chain combinations include:

(a) a heavy chain variable region comprising the amino acid sequence of SEQ ID NO:1; and (b) a light chain variable region comprising the amino acid sequence of SEQ ID NO:6; or (a) a heavy chain variable region comprising the amino acid sequence of SEQ ID NO:2; and (b) a light chain variable region comprising the amino acid sequence of SEQ ID NO:7; or (a) a heavy chain variable region comprising the amino acid sequence of SEQ ID NO:3; and (b) a light chain variable region comprising the amino acid sequence of SEQ ID NO:8; or (a) a heavy chain variable region comprising the amino acid sequence of SEQ ID NO:4; and (b) a light chain variable region comprising the amino acid sequence of SEQ ID NO:9; or (a) a heavy chain variable region comprising the amino acid sequence of SEQ ID NO:5; and (b) a light chain variable region comprising the amino acid sequence of SEQ ID NO:10.

In another aspect, the disclosure provides antibodies that comprise the heavy chain and light chain CDR1s, CDR2s and CDR3s of 2H5, 10B4, 8B5, 18E7 and 69A7 or combinations thereof. The amino acid sequences of the $V_H$ CDR1s of 2H5, 10B4, 8B5, 18E7 and 69A7 are shown in SEQ ID NOs:11, 12, 13, 14 and 15, respectively. The amino acid sequences of the $V_H$ CDR2s of 2H5, 10B4, 8B5, 18E7 and 69A7 are shown in SEQ ID NOs:16, 17, 18, 19 and 20, respectively. The amino acid sequences of the $V_H$ CDR3s of 2H5, 10B4, 8B5, 18E7 and 69A7 are shown in SEQ ID NOs:21 22, 23, 24 and 25, respectively. The amino acid sequences of the $V_k$ CDR1s of 2H5, 10B4, 8B5, 18E7 and 69A7 are shown in SEQ ID NOs:26, 27, 28, 29 and 30, respectively. The amino acid sequences of the $V_k$ CDR2s of 2H5, 10B4, 8B5, 18E7 and 69A7 are shown in SEQ ID NOs:31, 32, 33, 34 and 35, respectively. The amino acid sequences of the $V_k$ CDR3s of 2H5, 10B4, 8B5, 18E7 and 69A7 are shown in SEQ ID NOs:36, 37, 38, 39 and 40, respectively. The CDR regions are delineated using the Kabat system (Kabat, E. A., et al. (1991) Sequences of Proteins of immunological Interest, Fifth Edition, U.S. Department of Health and Human Services, NIH Publication No. 91-3242).

Given that each of these antibodies can bind to CD70 and that antigen-binding specificity is provided primarily by the CDR1, CDR2 and CDR3 regions, the $V_H$ CDR1, CDR2 and CDR3 sequences and $V_k$ CDR1, CDR2 and CDR3 sequences can be "mixed and matched" (i.e., CDRs from different antibodies can be mixed and matched, although each antibody must contain a $V_H$ CDR1, CDR2 and CDR3, and a $V_k$ CDR1, CDR2 and CDR3) to create other anti-CD70 binding molecules of the disclosure. CD70 binding of such "mixed and matched" antibodies can be tested using the binding assays described above and in the Examples (e.g., FACS, ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies 2H5, 10B4, 8B5, 18E7 and 69A7.

Accordingly, in another aspect, the disclosure provides an isolated monoclonal antibody or antigen binding portion thereof comprising:
 (a) a heavy chain variable region CDR1 comprising an amino acid sequence selected from the group consisting of SEQ ID NOs:11, 12, 13, 14 and 15;
 (b) a heavy chain variable region CDR2 comprising an amino acid sequence selected from the group consisting of SEQ ID NOs:16, 17, 18, 19 and 20;
 (c) a heavy chain variable region CDR3 comprising an amino acid sequence selected from the group consisting of SEQ ID NOs:21, 22, 23, 24 and 25;
 (d) a light chain variable region CDR1 comprising an amino acid sequence selected from the group consisting of SEQ ID NOs:26, 27, 28, 29 and 30;
 (e) a light chain variable region CDR2 comprising an amino acid sequence selected from the group consisting of SEQ ID NOs:31, 32, 33, 34 and 35; and
 (f) a light chain variable region CDR3 comprising an amino acid sequence selected from the group consisting of SEQ ID NOs:36, 37, 38, 39 and 40;
 wherein the antibody specifically binds CD70, preferably human CD70

In a preferred embodiment, the antibody comprises:
 (a) a heavy chain variable region CDR1 comprising SEQ ID NO:11;
 (b) a heavy chain variable region CDR2 comprising SEQ ID NO:16;
 (c) a heavy chain variable region CDR3 comprising SEQ ID NO:21;
 (d) a light chain variable region CDR1 comprising SEQ ID NO:26;
 (e) a light chain variable region CDR2 comprising SEQ ID NO:31; and
 (f) a light chain variable region CDR3 comprising SEQ ID NO:36.

In another preferred embodiment, the antibody comprises:
 (a) a heavy chain variable region CDR1 comprising SEQ ID NO:12;
 (b) a heavy chain variable region CDR2 comprising SEQ ID NO:17;
 (c) a heavy chain variable region CDR3 comprising SEQ ID NO:22;
 (d) a light chain variable region CDR1 comprising SEQ ID NO:27;
 (e) a light chain variable region CDR2 comprising SEQ ID NO:32; and
 (f) a light chain variable region CDR3 comprising SEQ ID NO:37.

In another preferred embodiment, the antibody comprises:
 (a) a heavy chain variable region CDR1 comprising SEQ ID NO:13;
 (b) a heavy chain variable region CDR2 comprising SEQ ID NO:18;
 (c) a heavy chain variable region CDR3 comprising SEQ ID NO:23;
 (d) a light chain variable region CDR1 comprising SEQ ID NO:28;
 (e) a light chain variable region CDR2 comprising SEQ ID NO:33; and
 (f) a light chain variable region CDR3 comprising SEQ ID NO:38.

In another preferred embodiment, the antibody comprises:
 (a) a heavy chain variable region CDR1 comprising SEQ ID NO:14;
 (b) a heavy chain variable region CDR2 comprising SEQ ID NO:19;
 (c) a heavy chain variable region CDR3 comprising SEQ ID NO:24;
 (d) a light chain variable region CDR1 comprising SEQ ID NO:29;
 (e) a light chain variable region CDR2 comprising SEQ ID NO:34; and
 (f) a light chain variable region CDR3 comprising SEQ ID NO:39.

In another preferred embodiment, the antibody comprises:
 (a) a heavy chain variable region CDR1 comprising SEQ ID NO:15;
 (b) a heavy chain variable region CDR2 comprising SEQ ID NO:20;
 (c) a heavy chain variable region CDR3 comprising SEQ ID NO:25;
 (d) a light chain variable region CDR1 comprising SEQ ID NO:30;
 (e) a light chain variable region CDR2 comprising SEQ ID NO:35; and
 (f) a light chain variable region CDR3 comprising SEQ ID NO:40.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. USA.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. USA.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present disclosure provides monoclonal antibodies comprising one or more heavy and/or light chain CDR3 domains from an antibody derived from a human or non-human animal, wherein the monoclonal antibody is capable of specifically binding to CD70. Within certain aspects, the present disclosure provides monoclonal antibodies comprising one or more heavy and/or light chain CDR3 domains from a non-human antibody, such as a mouse or rat antibody, wherein the monoclonal antibody is capable of specifically binding to CD70. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a human antibody, such as, for example, a human antibody obtained from a non-human animal, wherein the human antibody is capable of specifically binding to CD70. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to CD70 and wherein the CDR3 domain from the first human antibody replaces a CDR3 domain in a human antibody that is lacking binding specificity for CD70 to generate a second human antibody that is capable of specifically binding to CD70. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the disclosure comprises a heavy chain variable region from a particular germline heavy chain immunoglobulin gene and/or a light chain variable region from a particular germline light chain immunoglobulin gene.

For example, in a preferred embodiment, the disclosure provides an isolated monoclonal antibody or an antigen-binding portion thereof, comprising a heavy chain variable region that is the product of or derived from a human $V_H$ 3-30.3 gene, wherein the antibody specifically binds CD70. In another preferred embodiment, the disclosure provides an isolated monoclonal antibody or an antigen-binding portion thereof, comprising a heavy chain variable region that is the product of or derived from a human $V_H$ 3-33 gene, wherein the antibody specifically binds CD70. In another preferred embodiment, the disclosure provides an isolated monoclonal antibody or an antigen-binding portion thereof, comprising a heavy chain variable region that is the product of or derived from a human $V_H$ 4-61 gene, wherein the antibody specifically binds CD70. In another preferred embodiment, the disclosure provides an isolated monoclonal antibody or an antigen-binding portion thereof, comprising a light chain variable region that is the product of or derived from a human $V_K$ L6 gene, wherein the antibody specifically binds CD70. In another preferred embodiment, the disclosure provides an isolated monoclonal antibody or an antigen-binding portion thereof, comprising a light chain variable region that is the product of or derived from a human $V_K$ L18 gene, wherein the antibody specifically binds CD70. In another preferred embodiment, the disclosure provides an isolated monoclonal antibody or an antigen-binding portion thereof, comprising a light chain variable region that is the product of or derived from a human $V_K$ L15 gene, wherein the antibody specifically binds CD70.

In yet another preferred embodiment, the disclosure provides an isolated monoclonal antibody or antigen-binding portion thereof, wherein the antibody:

(a) comprises a heavy chain variable region that is the product of or derived from a human $V_H$ 3-30.3, 3-33 or 4-61 gene (which genes encode the amino acid sequences set forth in SEQ ID NOs:51, 52 and 53, respectively);

(b) comprises a light chain variable region that is the product of or derived from a human $V_K$ L6, L18 or L15 gene (which genes encode the amino acid sequences set forth in SEQ ID NOs:54, 55 and 56, respectively); and (c) the antibody specifically binds to CD70.

An example of an antibody having $V_H$ and $V_K$ of $V_H$ 3-30.3 and $V_K$ L6, respectively, is 2H5. An example of an antibody having $V_H$ and $V_K$ of $V_H$ 3-30.3 and $V_K$ L18, respectively, is 10B4. Examples of antibodies having $V_H$ and $V_K$ of $V_H$ 3-33 and $V_K$ L15, respectively, are 8B5 and 18E7. An example of an antibody having $V_H$ and $V_K$ of $V_H$ 4-61 and $V_K$ L6, respectively, is 69A7.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95% or even at least 96%, 97%, 98% or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5 or even no more than 4, 3, 2 or 1 amino acid difference from the amino acid sequence encoded by the germline immunoglobulin gene.

Homologous Antibodies

In yet another embodiment, an antibody of the disclosure comprises heavy and light chain variable regions comprising amino acid sequences that are homologous to the amino acid sequences of the preferred antibodies described herein and wherein the antibodies retain the desired functional properties of the anti-CD70 antibodies of the disclosure.

For example, the disclosure provides an isolated monoclonal antibody or antigen binding portion thereof, comprising a heavy chain variable region and a light chain variable region wherein:

(a) the heavy chain variable region comprises an amino acid sequence that is at least 80% homologous to an amino acid sequence selected from the group consisting of SEQ ID NOs:1, 2, 3, 4 and 5;

(b) the light chain variable region comprises an amino acid sequence that is at least 80% homologous to an amino acid sequence selected from the group consisting of SEQ ID NOs: 6, 7, 8, 9 and 10; and (c) the antibody specifically binds to CD70.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs:41, 42, 43, 44, 45, 46, 47, 48, 49 and 50, followed by testing of the encoded altered antibody for retained function (i.e., binding to human CD70 with a $K_D$ of $5\times10^{-8}$ M or less) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix and a gap weight of 16, 14, 12, 10, 8, 6 or 4 and a length weight of 1, 2, 3, 4, 5 or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain embodiments, an antibody of the disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 2H5, 10B4, 8B5, 18E7 or 69A7) or conservative modifications thereof and wherein the antibodies retain the desired functional properties of the anti-CD70 antibodies of the disclosure. Accordingly, the disclosure provides an isolated monoclonal antibody or antigen binding portion thereof, comprising a heavy chain variable region comprising CDR1, CDR2 and CDR3 sequences and a light chain variable region comprising CDR1, CDR2 and CDR3 sequences, wherein:

(a) the heavy chain variable region CDR3 sequence comprises an amino acid sequence selected from the group consisting of amino acid sequences of SEQ ID NOs:21, 22, 23, 24 and 25 and conservative modifications thereof;

(b) the light chain variable region CDR3 sequence comprises an amino acid sequence selected from the group consisting of amino acid sequence of SEQ ID NOs:36, 37, 38, 39 and 40 and conservative modifications thereof; and (c) the antibody specifically binds to CD70.

In a preferred embodiment, the heavy chain variable region CDR2 sequence comprises an amino acid sequence selected from the group consisting of amino acid sequences of SEQ ID NOs:16, 17, 18, 19 and 20 and conservative modifications thereof; and the light chain variable region CDR2 sequence comprises an amino acid sequence selected from the group consisting of amino acid sequences of SEQ ID NOs:31, 32, 33, 34 and 35 and conservative modifications thereof. In another preferred embodiment, the heavy chain variable region CDR1 sequence comprises an amino acid sequence selected from the group consisting of amino acid sequences of SEQ ID NOs:11, 12, 13, 14 and 15 and conservative modifications thereof; and the light chain variable region CDR1 sequence comprises an amino acid sequence selected from the group consisting of amino acid sequences of SEQ ID NOs:26, 27, 28, 29 and 30 and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the function set forth in (c)) using the functional assays described herein.

Antibodies that Bind to the Same Epitope as Anti-CD70 Antibodies of the Disclosure In another embodiment, the disclosure provides antibodies that bind to the same epitope on human CD70 as any of the CD70 monoclonal antibodies of the disclosure (i.e., antibodies that have the ability to cross-compete for binding to CD70 with any of the monoclonal antibodies of the disclosure). In preferred embodiments, the reference antibody for cross-competition studies can be the monoclonal antibody 2H5 (having $V_H$ and $V_L$ sequences as shown in SEQ ID NOs:1 and 6, respectively) or the monoclonal antibody 10B4 (having $V_H$ and $V_L$ sequences as shown in SEQ ID NOs:2 and 7, respectively) or the monoclonal antibody 8B5 (having $V_H$ and $V_L$ sequences as shown in SEQ ID NOs:3 and 8, respectively) or the monoclonal antibody 18E7 (having $V_H$ and $V_L$ sequences as shown in SEQ ID NOs:4 and 9, respectively) or the monoclonal antibody 69A7 (having $V_H$ and $V_L$ sequences as shown in SEQ ID NOs:5 and 10, respectively). Such cross-competing antibodies can be identified based on their ability to cross-compete with 2H5, 10B4, 8B5, 18E7 or 69A7 in standard CD70 binding assays. For example, BIAcore analysis, ELISA assays or flow cytometry may be used to demonstrate cross-competition with the antibodies of the current disclosure. The ability of a test antibody to inhibit the binding of, for example, 2H5, 10B4, 8B5, 18E7 or 69A7, to human CD70 demonstrates that the test antibody can compete with 2H5, 10B4, 8B5, 18E7 or 69A7 for binding to human CD70 and thus binds to the same epitope on human CD70 as 2H5, 10B4, 8B5, 18E7 or 69A7. In a preferred embodiment, the antibody that binds to the same epitope on human CD70 as 2H5, 10B4, 8B5, 18E7 or 69A7 is a human monoclonal antibody. Such human monoclonal antibodies can be prepared and isolated as described in the Examples.

Engineered and Modified Antibodies

An antibody of the disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter and U.S. Pat. Nos. 5,530,101; 5,585,089; 5,693,762 and 6,180,370 to Queen et al.)

Accordingly, another embodiment of the disclosure pertains to an isolated monoclonal antibody or antigen binding portion thereof, comprising a heavy chain variable region comprising CDR1, CDR2 and CDR3 sequences comprising an amino acid sequence selected from the group consisting of SEQ ID NOs:11, 12, 13, 14 and 15, SEQ ID NOs:16, 17, 18, 19 and 20 and SEQ ID NOs:21, 22, 23, 24 and 25, respectively and a light chain variable region comprising CDR1, CDR2 and CDR3 sequences comprising an amino acid sequence selected from the group consisting of SEQ ID NOs:26, 27, 28, 29 and 30, SEQ ID NOs:31, 32, 33, 34 and 35 and SEQ ID NOs:36, 37, 38, 39 and 40, respectively. Thus, such antibodies contain the $V_H$ and $V_L$ CDR sequences of monoclonal antibodies 2H5, 10B4, 8B5, 18E7 or 69A7 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_000109 and NT_024637). As another example, the following heavy chain-germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Preferred framework sequences for use in the antibodies of the disclosure are those that are structurally similar to the framework sequences used by selected antibodies of the disclosure, e.g., similar to the V$_H$ 3-30.3 framework sequences (SEQ ID NO:51) and/or the V$_H$ 3-33 framework sequences (SEQ ID NO:52) and/or the V$_H$ 4-61 framework sequences (SEQ ID NO:53) and/or the V$_K$ L6 framework sequences (SEQ ID NO:54) and/or the V$_K$ L18 framework sequences (SEQ ID NO:55) and/or the V$_K$ L15 framework sequences (SEQ ID NO:56) used by preferred monoclonal antibodies of the disclosure. The V$_H$ CDR1, CDR2 and CDR3 sequences and the V$_K$ CDR1, CDR2 and CDR3 sequences, can be grafted onto framework regions that have the identical sequence as that found in the germline immunoglobulin gene from which the framework sequence derive or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the V$_H$ and/or V$_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the disclosure provides isolated anti-CD70 monoclonal antibodies or antigen binding portions thereof, comprising a heavy chain variable region comprising: (a) a V$_H$ CDR1 region comprising an amino acid sequence selected from the group consisting of SEQ ID NOs:11, 12, 13, 14 and 15 or an amino acid sequence having one, two, three, four or five amino acid substitutions, deletions or additions as compared to SEQ ID NOs:11, 12, 13, 14 and 15; (b) a V$_H$ CDR2 region comprising an amino acid sequence selected from the group consisting of SEQ ID NOs: 16, 17, 18, 19 and 20 or an amino acid sequence having one, two, three, four or five amino acid substitutions, deletions or additions as compared to SEQ ID NOs:16, 17, 18, 19 and 20; (c) a V$_H$ CDR3 region comprising an amino acid sequence selected from the group consisting of SEQ ID NOs:21, 22, 23, 24 and 25 or an amino acid sequence having one, two, three, four or five amino acid substitutions, deletions or additions as compared to SEQ ID NOs:21, 22, 23, 24 and 25; (d) a V$_K$ CDR1 region comprising an amino acid sequence selected from the group consisting of SEQ ID NOs:26, 27, 28, 29 and 30 or an amino acid sequence having one, two, three, four or five amino acid substitutions, deletions or additions as compared to SEQ ID NOs:26, 27, 28, 29 and 30; (e) a V$_K$ CDR2 region comprising an amino acid sequence selected from the group consisting of SEQ ID NOs:31, 32, 33, 34 and 35 or an amino acid sequence having one, two, three, four or five amino acid substitutions, deletions or additions as compared to SEQ ID NOs:31, 32, 33, 34 and 35; and (f) a V$_K$ CDR3 region comprising an amino acid sequence selected from the group consisting of SEQ ID NOs:36, 37, 38, 39 and 40 or an amino acid sequence having one, two, three, four or five amino acid substitutions, deletions or additions as compared to SEQ ID NOs:36, 37, 38, 39 and 40.

Engineered antibodies of the disclosure include those in which modifications have been made to framework residues within V$_H$ and/or V$_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the disclosure. For example, for 10B4, amino acid residue #2 (within FR1) of V$_H$ is an isoleucine whereas this residue in the corresponding V$_H$ 3-30.3 germline sequence is a valine. To return the framework region sequences to their germline configuration, the somatic mutations can be "backmutated" to the germline sequence by, for example, site-directed mutagenesis or PCR-mediated mutagenesis (e.g., residue 2 of FR1 of the V$_H$ of 10B4 can be "backmutated" from isoleucine to valine).

As another example, for 10B4, amino acid residue #30 (within FR1) of V$_H$ is a glycine whereas this residue in the corresponding V$_H$ 3-30.3 germline sequence is a serine. To return the framework region sequences to their germline configuration, for example, residue 30 of FR1 of the V$_H$ of 10B4 can be "backmutated" from glycine to serine.

As another example, for 8B5, amino acid residue #24 (within FR1) of V$_H$ is a threonine whereas this residue in the corresponding V$_H$ 3-33 germline sequence is an alanine. To return the framework region sequences to their germline configuration, for example, residue 24 of FR1 of the V$_H$ of 8B5 can be "backmutated" from threonine to alanine.

As another example, for 8B5, amino acid residue #77 (within FR3) of V$_H$ is a lysine whereas this residue in the corresponding V$_H$ 3-33 germline sequence is an asparagine. To return the framework region sequences to their germline configuration, for example, residue 11 of FR3 of the V$_H$ of 8B5 can be "backmutated" from lysine to asparagine.

As another example, for 8B5, amino acid residue #80 (within FR3) of V$_H$ is a serine whereas this residue in the corresponding V$_H$ 3-33 germline sequence is a tyrosine. To return the framework region sequences to their germline configuration, for example, residue 14 of FR3 of the V$_H$ of 8B5 can be "backmutated" from serine to tyrosine.

As another example, for 69A7, amino acid residue #50 (within FR2) of V$_H$ is a leucine whereas this residue in the corresponding V$_H$ 4-61 germline sequence is an isoleucine. To return the framework region sequences to their germline configuration, for example, residue 13 of FR2 of the V$_H$ of 69A7 can be "backmutated" from leucine to isoleucine.

As another example, for 69A7, amino acid residue #85 (within FR3) of V$_H$ is an arginine whereas this residue in the corresponding V$_H$ 4-61 germline sequence is a serine. To return the framework region sequences to their germline configuration, for example, residue 18 of FR3 of the V$_H$ of 69A7 can be "backmutated" from arginine to serine.

As another example, for 69A7, amino acid residue #89 (within FR3) of V$_H$ is a threonine whereas this residue in the corresponding V$_H$ 4-61 germline sequence is an alanine. To return the framework region sequences to their germline configuration, for example, residue 22 of FR3 of the V$_H$ of 69A7 can be "backmutated" from threonine to alanine.

As another example, for 10B4, amino acid residue #46 (within FR2) of V$_L$ is a phenylalanine whereas this residue in the corresponding V$_L$ L18 germline sequence is a leucine. To return the framework region sequences to their germline configuration, for example, residue 12 of FR2 of the $V_L$ of 10B4 can be "backmutated" from phenylalanine to leucine.

As another example, for 69A7, amino acid residue #49 (within FR2) of $V_L$ is a phenylalanine whereas this residue in the corresponding $V_L$ L6 germline sequence is a tyrosine. To return the framework region sequences to their germline configuration, for example, residue 15 of FR2 of the $V_L$ of 69A7 can be "backmutated" from phenylalanine to tyrosine.

Another type of framework modification involves mutating one or more residues within the framework region or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Engineered antibodies of the disclosure also include those in which modifications have been made to amino acid residues to increase or decrease immunogenic responses through amino acid modifications that alter interaction of a T-cell epitope on the antibody (see e.g., U.S. Pat. Nos. 6,835,550; 6,897,049 and 6,936,249).

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example; one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705 and Ms709 lack the fucosyltransferase gene, FUT8 (alpha (1,6) fucosyltransferase), such that antibodies expressed in the Ms704, Ms705 and Ms709 cell lines lack fucose on their carbohydrates. The Ms704, Ms705 and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)—N-acetylglucosaminyltransferase III (GnIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the disclosure is pegylation. An antibody can be pegylated to, for example, increase the biological (e.g., serum) half life of the antibody. To pegylate an antibody, the antibody or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Antibody Physical Properties

The antibodies of the present disclosure may be further characterized by the various physical properties of the anti-CD19 antibodies. Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala FA and Morrison SL (2004) *J Immunol* 172:5489-94; Wallick et al (1988) *J Exp Med* 168:1099-109; Spiro R G (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N—X—S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-CD19 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present disclosure do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-CD19 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present disclosure is greater than 60° C., preferably greater than 65° C., even more preferably greater than 70° C. Alternatively, the thermal stability of an antibody may be measure using circular dichroism (Murray et al. (2002) *J Chromatogr Sci* 40:343-9).

In a preferred embodiment, antibodies are selected that do not rapidly degrade. Fragmentation of an anti-CD19 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-CD70 antibodies having $V_H$ and $V_K$ sequences disclosed herein can be used to create new anti-CD70 antibodies by modifying the $V_H$ and/or $V_K$ sequences or the constant region(s) attached thereto. Thus, in another aspect of the disclosure, the structural features of an anti-CD70 antibody of the disclosure, e.g. 2H5, 10B4, 8B5, 18E7 or 69A7, are used to create structurally related anti-CD70 antibodies that retain at least one functional property of the antibodies of the disclosure, such as binding to human CD70. For example, one or more CDR regions of 2H5, 10B4, 8B5, 18E7 or 69A7 or mutations thereof, can be combined recombinantly with known framework regions and/or other CDRs to create additional, recombinantly-engineered, anti-CD70 antibodies of the disclosure, as discussed above. Other types of modifications include those described in the previous section. The starting material for the engineering method is one or more of the $V_H$ and/or $V_K$ sequences provided herein or one or more CDR regions thereof. To create the engineered antibody, it is not necessary to actually prepare (i.e., express as a protein) an antibody having one or more of the $V_H$ and/or $V_K$ sequences provided herein or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the disclosure provides a method for preparing an anti-CD70 antibody comprising:

(a) providing: (i) a heavy chain variable region antibody sequence comprising a CDR1 sequence selected from the group consisting of SEQ ID NOs:11, 12, 13, 14 and 15, a CDR2 sequence selected from the group consisting of SEQ ID NOs:16, 17, 18, 19 and 20 and/or a CDR3 sequence selected from the group consisting of SEQ ID NOs:21, 22, 23, 24 and 25; and/or (ii) a light chain variable region antibody sequence comprising a CDR1 sequence selected from the group consisting of SEQ ID NOs:26, 27, 28, 29 and 30, a CDR2 sequence selected from the group consisting of SEQ ID NOs:31, 32, 33, 34 and 35 and/or a CDR3 sequence selected from the group consisting of SEQ ID NOs:36, 37, 38, 39 and 40;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CD70 antibodies described herein, which functional properties include, but are not limited to specifically binding to CD70.

The functional properties of the altered antibodies can be assessed using standard assays available in the art and/or described herein, such as those set forth in the Examples (e.g., flow cytometry, binding assays).

In certain embodiments of the methods of engineering antibodies of the disclosure, mutations can be introduced randomly or selectively along all or part of an anti-CD70 antibody coding sequence and the resulting modified anti-CD70 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Disclosure

Another aspect of the disclosure pertains to nucleic acid molecules that encode the antibodies of the disclosure. The nucleic acids may be present in whole cells, in a cell lysate or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the disclosure can be, for example, DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the disclosure are those encoding the VH and VL sequences of the 2H5, 10B4, 8B5, 18E7 or 69A7 monoclonal antibodies. DNA sequences encoding the VH sequences of 2H5, 10B4, 8B5, 18E7 and 69A7 are shown in SEQ ID NOs:41, 42, 43, 44 and 45, respectively. DNA sequences encoding the VL sequences of 2H5, 10B4, 8B5, 18E7 and 69A7 are shown in SEQ ID NOs:46, 47, 48, 49 and 50, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1, IgG2, IgG3 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of the Disclosure

Monoclonal antibodies (mabs) of the present disclosure can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter and U.S. Pat. Nos. 5,530,101; 5,585,089; 5,693,762 and 6,180,370 to Queen et al.).

In a preferred embodiment, the antibodies of the disclosure are human monoclonal antibodies. Such human monoclonal antibodies directed against CD70 can be generated using transgenic or transchromosomic mice carrying parts of the human immune system rather than the mouse system. These transgenic and transchromosomic mice include mice referred to herein as the HuMAb Mouse® and KM Mouse®, respectively and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93 and Harding, F. and Lonberg, N. (1995) Ann. N.Y. Acad. Sci, 764:536-546). The preparation and use of HuMab mice and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the disclosure can be raised using a mouse that carries human immunoglobulin sequences on transgenes and transchomosomes, such as a mouse that carries a human heavy chain transgene and a human light chain transchromosome. Such mice, referred to herein as the "KM Mouse®", are described in detail in PCT Publication WO 02/43478 to Ishida et al.

Still further, alternative transgenic animal systems expressing human immunoglobulin genes are available in the art and can be used to raise anti-CD70 antibodies of the disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CD70 antibodies of the disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. As another example, cows carrying human heavy and light chain transchromosomes have been described in the art (Kuroiwa et al. (2002) Nature Biotechnology 20:889-894) and can be used to raise anti-CD70 antibodies of the disclosure.

Human monoclonal antibodies of the disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the disclosure, such mice can be immunized with a CD70-expressing cell line, a purified or enriched preparation of CD70 antigen and/or recombinant CD70 or an CD70 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first immunization. For example, a purified or recombinant preparation (5-50 μg) of CD70 antigen can be used to immunize the human Ig mice intraperitoneally.

Detailed procedures to generate fully human monoclonal antibodies to CD70 are described in Example 1 below. Cumulative experience with various antigens has shown that the transgenic mice respond when initially immunized intraperitoneally (IP) with antigen in complete Freund's adjuvant, followed by every other week IP immunizations up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained, for example, by retroorbital bleeds. The plasma can be screened by ELISA and mice with sufficient titers of anti-CD70 human immunoglobulin can be used for fusions (as described in Example 1). Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. Generation of HCo7 and HCo12 mouse strains are described in U.S. Pat. No. 5,770,429 and Example 2 of PCT Publication WO 01/09187, respectively. In addition, both HCo7 and HCo12 transgene can be bred together into a single mouse having two different human heavy chain transgenes (HCo7/HCo12). Alternatively or additionally, the KM Mouse® strain can be used, as described in PCT Publication WO 02/43478.

Generation of Hybridomas Producing Human Monoclonal Antibodies of the Disclosure To generate hybridomas producing human monoclonal antibodies of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the single cell suspensions of splenic lymphocytes from immunized mice can be fused using an electric field based electrofusion method, using a Cyto Pulse large chamber cell fusion electroporator (Cyto Pulse Sciences, Inc., Glen Burnie, Md.). Cells are plated at approximately $2 \times 10^5$ in flat bottom microtiter plate, followed by a one week incubation in DMEM high glucose medium with L-glutamine and sodium pyruvate (Mediatech, Inc., Herndon, Va.) and further containing 20% fetal Bovine Serum (Hyclone, Logan, Utah), 18% P388D1 conditional media, 5% Origen Hybridoma cloning factor (BioVeris, Gaithersburg, Va.), 4 mM L-glutamine, 5 mM HEPES, 0.055 mM β-mercaptoethanol, 50 units/ml penicillin, 50 mg/ml streptomycin and 1× Hypoxanthine-aminopterin-thymidine (HAT) media (Sigma; the HAT is added 24 hours after the fusion). After one week, cells cultured in medium in which HAT was used was replaced with HT. Individual wells can then be screened by ELISA for human monoclonal IgM and IgG antibodies. Hybridoma growth can be observed usually after 10-14 days. The antibody secreting hybridomas can be replated, screened again and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS and the concentration can be determined by OD280 using 1.43 extinction coefficient. The monoclonal antibodies can be aliquoted and stored at −80° C.

Generation of Transfectomas Producing Monoclonal Antibodies of the Disclosure

Antibodies of the disclosure also can be produced in a host cell transfectoma using, for example, a combination of recombinant DNA techniques and gene transfection methods as is well known in the art (e.g., Morrison, S. (1985) *Science* 229:1202).

For example, to express the antibodies or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the disclosure may carry additional sequences, such as sequences that regulate replication of the vector in host cells (e.g. origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells and most preferably mammalian host cells, is the most preferred because such eukaryotic cells and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the disclosure can be tested for binding to CD70 by, for example, flow cytometry. Briefly, CD70-expressing cells are freshly harvested from tissue culture flasks and a single cell suspension prepared. CD70-expressing cell suspensions are either stained with primary antibody directly or after fixation with 1% paraformaldehyde in PBS. Approximately one million cells are resuspended in PBS containing 0.5% BSA and 50-200 μg/ml of primary antibody and incubated on ice for 30 minutes. The cells are washed twice with PBS containing 0.1% BSA, 0.01% $NaN_3$, resuspended in 100 μl of 1:100 diluted FITC-conjugated goat-anti-human IgG (Jackson ImmunoResearch, West Grove, Pa.) and incubated on ice for an additional 30 minutes. The cells are again washed twice, resuspended in 0.5 ml of wash buffer and analyzed for fluorescent staining on a FACSCalibur cytometer (Becton-Dickinson, San Jose, Calif.).

Alternatively, antibodies of the disclosure can be tested for binding to CD70 by standard ELISA. Briefly, microtiter plates are coated with purified CD70 at 0.25 μg/ml in PBS and then blocked with 5% bovine serum albumin in PBS. Dilutions of antibody (e.g., dilutions of plasma from CD70-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml) and analyzed at OD of 405-650. Preferably, mice which develop the highest titers will be used for fusions.

An ELISA assay as described above can also be used to screen for hybridomas that show positive reactivity with CD70 immunogen. Hybridomas that bind with high avidity to CD70 are subcloned and further characterized. One clone from each hybridoma, which retains the reactivity of the parent cells (by ELISA), can be chosen for making a 5-10 vial cell bank stored at −140° C. and for antibody purification.

To purify anti-CD70 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS and the concentration can be determined by $OD_{280}$ using 1.43 extinction coefficient. The monoclonal antibodies can be aliquoted and stored at −80° C.

To determine if the selected anti-CD70 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD70 coated-ELISA plates as described above. Biotinylated mAb binding can be detected with a strep-avidin-alkaline phosphatase probe. Alternatively, competition studies can be performed using radiolabelled antibody and unlabelled competing antibodies can be detected in a Scatchard analysis, as further described in the Examples below.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted With 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CD70 human IgGs can be further tested for reactivity with CD70 antigen by Western blotting. Briefly, CD70 can be prepared and subjected to sodium dodecyl sulfate polyacrylamide gel electrophoresis. After electrophoresis, the separated antigens are transferred to nitrocellulose membranes, blocked with 10% fetal calf serum and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present disclosure features an anti-CD70 antibody or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thiotepa, chlorambucil, melphalan, carmustine (BSNU) and lomustine (CCNU), cyclothosphamide, busulfan, dibromomannitol, streptozotocin, mitomycin C and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin and anthramycin (AMC)) and anti-mitotic agents (e.g., vincristine and vinblastine).

Other preferred examples of therapeutic cytotoxins that can be conjugated to an antibody of the disclosure include duocarmycins, calicheamicins, maytansines and auristatins and derivatives thereof. An example of a calicheamicin antibody conjugate is commercially available (Mylotarg™; Wyeth-Ayerst).

Cytoxins can be conjugated to antibodies of the disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, iodine$^{125}$, indium$^{111}$, yttrium$^{90}$ and lutetium$^{177}$. Method for preparing radioununconjugates are established in the art. Examples of radioimmunoconjugates are commercially available, including Zevalin™ (IDEC Pharmaceuticals) and Bexxar™ (Corixa Pharmaceuticals) and similar methods can be used to prepare radioimmunoconjugates using the antibodies of the disclosure.

The antibody conjugates of the disclosure can be used to modify a given biological response and the drug moiety is not to be construed as limited to classical chemical therapeutic agents. For example, the drug moiety may be a protein or polypeptide possessing a desired biological activity. Such proteins may include, for example, an enzymatically active toxin or active fragment thereof, such as abrin, ricin A, pseudomonas exotoxin or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF") or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstroin et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results and Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985) and Thorpe et al., "The Preparation And Cytotoxic Properties Of Antibody-Toxin Conjugates", Immunol. Rev., 62:119-58 (1982).

Bispecific Molecules

In another aspect, the present disclosure features bispecific molecules comprising an anti-CD70 antibody or a fragment thereof, of the disclosure. An antibody of the disclosure or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the disclosure, an antibody of the disclosure can be functionally linked (e.g., by chemical coupling, genetic fusion, non-covalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for CD70 and a second binding specificity for a second target epitope. In a particular embodiment of the disclosure, the second target epitope is an Fc receptor, e.g., human FcγRI (CD64) or a human Fcα receptor (CD89). Therefore, the disclosure includes bispecific molecules capable of binding both to FcγR or FcαR expressing effector cells (e.g., monocytes, macrophages or polymorphonuclear cells (PMNs)) and to target cells expressing CD70. These bispecific molecules target CD70 expressing cells to effector cell and trigger Fc receptor-mediated effector cell activities, such as phagocytosis of an CD70 expressing cells, antibody dependent cell-mediated cytotoxicity (ADCC), cytokine release or generation of superoxide anion.

In an embodiment of the disclosure in which the bispecific molecule is multispecific, the molecule can further include a third binding specificity, in addition to an anti-Fc binding specificity and an anti-CD70 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor and thereby results in an enhancement of the effect of the binding determinants for the $F_C$ receptor or target cell antigen. The "anti-enhancement factor portion" can bind an $F_C$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the disclosure comprise as a binding specificity at least one antibody or an antibody fragment thereof, including, e.g., an Fab, Fab', F(ab')$_2$, Fv or a single chain Fv. The antibody may also be a light chain or heavy chain dimer or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), Fcγ RII(CD32) and FcγRIII (CD16). In one preferred embodiment, the Fcγ receptor a human high affinity FcγRIII. The human FcγRI is a 72 kDa molecule, which shows high affinity for monomeric IgG ($10^8$-$10^9$ M$^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J Immunol 155 (10): 4996-5002 and PCT Publication WO 94/10332. The H22 antibody producing cell line was deposited at the American Type Culture Collection under the designation HA022CLI and has the accession no. CRL 11177.

In still other preferred embodiments, the binding specificity for an Fc receptor is provided by an antibody that binds to a human IgA receptor, e.g., an Fc-alpha receptor (FcγRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity (Q 5×10$^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) J. Immunol. 148: 1764).

FcαRI and FcγRI are preferred trigger receptors for use in the bispecific molecules of the disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the disclosure include, e.g., murine, chimeric and humanized monoclonal antibodies.

The bispecific molecules of the present disclosure can be prepared by conjugating the constituent binding specificities, e.g., the anti-FcR and anti-CD70 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP) and sulfosuccinimidyl 4-(N-maleimidomethyl)cyclohaxane-1-carboxylate (sulfo-SMCC) (see e.g., Karpovslcy et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83) and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×nAb, mAb×Fab, Fab×F(ab')$_2$ or ligand× Fab fusion protein. A bispecific molecule of the disclosure can be a single chain molecule comprising one single chain antibody and a binding determinant or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition) or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present disclosure provides a composition, e.g., a pharmaceutical composition, containing one or a combination of monoclonal antibodies or antigeri-binding portion(s) thereof, of the present disclosure, formulated together with a pharmaceutically acceptable carrier. Such compositions may include one or a combination of (e.g., two or more different) antibodies or immunoconjugates or bispecific molecules of the disclosure. For example, a pharmaceutical composition of the disclosure can comprise a combination of antibodies (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include an anti-CD70 antibody of the present disclosure combined with at least one other anti-inflammatory or immunosuppressant agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol and the like; and (3) metal chelating agents, such as citric acid, ethylenediamine tetraacetic acid (EDTA), sorbitol, tartaric acid, phosphoric acid and the like.

Examples of suitable aqueous and nonaqueous carriers that may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of presence of microorganisms may be ensured both by sterilization procedures, supra and by the inclusion of various antibacterial and antifungal agents, for example, paraben, chlorobutanol, phenol sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome or other ordered structure suitable to high drug concentration. The carrier can be a solvent or dispersion medium containing, for example, water, ethanol, polyol (for example, glycerol, propylene glycol and liquid polyethylene glycol and the like) and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved and (b) the limitations inherent in the art of compounding such an active compound for the treatment of sensitivity in individuals.

For administration of the antibody, the dosage ranges from about 0.0001 to 100 mg/kg and more usually 0.01 to 25 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. Higher dosages, e.g., 15 mg/kg body weight, 20 mg/kg body weight or 25 mg/kg body weight can be used as needed. An exemplary treatment regime entails administration once per week, once every two weeks, once every three weeks, once every four weeks, once a month, once every 3 months or once every three to 6 months. Particular dosage regimens for an anti-CD70 antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more anti-CD70 monoclonal antibodies of the disclosure with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition and mode of administration, without being toxic to the patient. The selected dosage level will depend upon a variety of pharmacokinetic factors including the activity of the particular compositions of the present disclosure employed or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated and like factors well known in the medical arts.

A "therapeutically effective dosage" of an anti-CD70 antibody of the disclosure preferably results in a decrease in severity of disease symptoms, an increase in frequency and duration of disease symptom-free periods or a prevention of impairment or disability due to the disease affliction. For example, for the treatment of CD70+ tumors, a "therapeutically effective dosage" preferably inhibits cell growth or tumor growth by at least about 20%, more preferably by at least about 40%, even more preferably by at least about 60% and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection and includes, without limitation, intravenous, intramuscular, intraarterial, intrathecal, intracapsular, intraorbital, intracardiac, intradeimal, intraperitoneal, transtracheal, subcutaneous, subcuticular, intraarticular, subcapsular, subarachnoid, intraspinal, epidural and intrasternal injection and infusion.

Alternatively, an antibody of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches and microencapsulated delivery systems. Biodegradable, biocompatible polymers can be used, such as ethylene vinyl acetate, polyanhydrides, polyglycolic acid, collagen, polyorthoesters and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems and modules are known to those skilled in the art.

In certain embodiments, the human monoclonal antibodies of the disclosure can be formulated to ensure proper distribution in viva. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Disclosure

The antibodies, particularly the human antibodies, antibody compositions and methods of the present disclosure have numerous in vitro and in vivo diagnostic and therapeutic utilities involving the diagnosis and treatment of CD70 mediated disorders. For example, these molecules can be administered to cells in culture, in vitro or ex vivo or to human subjects, e.g., in vivo, to treat, prevent and to diagnose a variety of disorders. As used herein, the term "subject" is intended to include human and non-human animals. The term "non-human animals" includes all vertebrates, e.g., mammals and non-mammals, such as non-human primates, sheep, dogs, cats, cows, horses, chickens, amphibians and reptiles. Preferred subjects include human patients having disorders mediated by CD70 activity. The methods are particularly suitable for treating human patients having a disorder associated with aberrant CD70 expression. When antibodies to CD70 are administered together with another agent, the two can be administered in either order or simultaneously.

Given the specific binding of the antibodies of the disclosure for CD70, the antibodies of the disclosure can be used to specifically detect CD70 expression on the surface of cells and, moreover, can be used to purify CD70 via immunoaffinity purification.

CD70 is expressed in a variety of human cancers, including renal cell carcinomas, metastatic breast cancers, brain tumors, leukemias, lymphomas and nasopharangeal carcinomas (Junker et al. (2005) *J Urol.* 173:2150-3; Sloan et al. (2004) *Am J Pathol.* 164:315-23; Held-Feindt and Mentlein (2002) *Int J Cancer* 98:352-6; Hishima et al. (2000) *Am J Surg Pathol.* 24:742-6; Lens et al. (1999) *Br J Haematol.* 106:491-503). An anti-CD70 antibody may be used alone to inhibit the growth of cancerous tumors. Alternatively, an anti-CD70 antibody may be used in conjunction with other immunogenic agents, standard cancer treatments or other antibodies, as described below.

Preferred cancers whose growth may be inhibited using the antibodies of the disclosure include cancers typically responsive to immunotherapy. Non-limiting examples of preferred cancers for treatment include renal cancer (e.g., renal cell carcinoma), breast cancer, brain tumors, chronic or acute leukemias including acute myeloid leukemia, chronic myeloid leukemia, acute lymphoblastic leukemia, chronic lymphocytic leukemia, lymphomas (e.g., Hodgkin's and, non-Hodgkin's lymphoma, lymphocytic lymphoma, primary CNS lymphoma, T-cell lymphoma) and nasopharangeal carcinomas. Examples of other cancers that may be treated using the methods of the disclosure include melanoma (e.g., metastatic malignant melanoma), prostate cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, environmentally induced cancers including those induced by asbestos, e.g., mesothelioma and combinations of said cancers.

Furthermore, given the expression of CD70 on various tumor cells, the human antibodies, antibody compositions and methods of the present disclosure can be used to treat a subject with a tumorigenic disorder, e.g., a disorder characterized by the presence of tumor cells expressing CD70 including, for example, renal cell carcinomas (RCC), such as clear cell RCC, glioblastoma, breast cancer, brain tumors, nasopharangeal carcinomas, non-Hodgkin's lymphoma (NHL), acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas. of B lineage, angioimmunoblastic lymphadenopathy (AILD)-like T cell lymphoma, HIV associated body cavity based lymphomas, embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas.

Accordingly, in one embodiment, the disclosure provides a method of inhibiting growth of tumor cells in a subject, comprising administering to the subject a therapeutically effective amount of an anti-CD70 antibody or antigen-binding portion thereof. Preferably, the antibody is a human anti-CD70 antibody (such as any of the human anti-human CD70 antibodies described herein). Additionally or alternatively, the antibody may be a chimeric or humanized anti-CD70 antibody.

Additionally, the interaction of CD70 with CD27 has also been proposed to play a role in cell-mediated autoimmune diseases, such as experimental autoimmune encephalomyelitis (EAE) (Nakajima et al. (2000) *J. Neuroimmunol.* 109:188-96). This effect was thought to be mediated in part by an inhibition of TNF-alpha production. Furthermore, blocking of CD70 signaling inhibits CD40-mediated clonal expansion of CD8+ T-cells and reduces the generation of CD8+ memory T-cells (Taraban et al. (2004) *J. Immunol.* 173:6542-6). As such, the human antibodies, antibody compositions and methods of the present disclosure can be used to treat a subject with an autoimmune disorder, e.g., a disorder characterized by the presence of B-cells expressing CD70 including, for example, experimental autoimmune encephalomyelitis. Additional autoimmune disorders in which the antibodies of the disclosure can be used include, but are not limited to systemic lupus erythematosus (SLE), insulin dependent diabetes mellitus (IDDM), inflammatory bowel disease (IBD) (including Crohn's Disease, ulcerative colitis and Celiac disease), multiple sclerosis (MS), psoriasis, autoimmune thyroiditis, rheumatoid arthritis (RA) and glomerulonephritis. Furthermore, the antibody compositions of the disclosure can be used for inhibiting or preventing transplant rejection or in the treatment of graft versus host disease (GVHD).

Additionally, the interaction of CD70 with CD27 has also been proposed to play a role in signalling on CD4+ T cells. Some viruses have been shown to signal the CD27 pathway, leading to destruction of neutralizing antibody responses (Matter et al. (2006) *J Exp Med* 203:2145-55). As such, the human antibodies, antibody compositions and methods of the present disclosure can be used to treat a subject with a viral infection including, for example, infections from human immunodeficiency virus (HIV), Hepatitis (A, B, & C), Herpesvirus, (e.g., VZV, HSV-1, HAV-6, HSV-II and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus and lymphocytic choriomeningitis virus (LCMV).

or in the treatment of HIV infection/AIDS. Additionally, the human antibodies, antibody compositions and methods of the present disclosure can be used to inhibit TNF-alpha production.

In one embodiment, the antibodies (e.g., human monoclonal antibodies, multispecific and bispecific molecules and compositions) of the disclosure can be used to detect levels of CD70 or levels of cells which contain CD70 on their membrane surface, which levels can then be linked to certain disease symptoms. Alternatively, the antibodies can be used to inhibit or block CD70 function which, in turn, can be linked to the prevention or amelioration of certain disease symptoms, thereby implicating CD70 as a mediator of the disease. This can be achieved by contacting an experimental sample and a control sample with the anti-CD70 antibody under conditions that allow for the formation of a complex between the antibody and CD70. Any complexes formed between the antibody and CD70 are detected and compared in the experimental sample and the control.

In another embodiment, the antibodies (e.g., human antibodies, multispecific and bispecific molecules and compositions) of the disclosure can be initially tested for binding activity associated with therapeutic or diagnostic use in vitro.

For example, compositions of the disclosure can be tested using the flow cytometric assays described in the Examples below.

The antibodies (e.g., human antibodies, multispecific and bispecific molecules, immunoconjugates and compositions) of the disclosure have additional utility in therapy and diagnosis of CD70-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing CD70; to mediate phagocytosis or ADCC of a cell expressing CD70 in the presence of human effector cells; or to block CD70 ligand binding to CD70.

In a particular embodiment, the antibodies (e.g., human antibodies, multispecific and bispecific molecules and compositions) are used in vivo to treat, prevent or diagnose a variety of CD70-related diseases. Examples of CD70-related diseases include, among others, autoimmune disorders, experimental autoimmune encephalomyelitis (EAE), cancer, renal cell carcinomas (RCC), such as clear cell RCC, glioblastoma, breast cancer, brain tumors, nasopharangeal carcinomas, non-Hodgkin's lymphoma, acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, and other B-cell lymphomas.

Suitable routes of administering the antibody compositions (e.g., human monoclonal antibodies, multispecific and bispecific molecules and immunoconjugates) of the disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CD70 antibodies of the disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-CD70 antibodies or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the disclosure can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CD70 and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the disclosure and/or effector cells armed with these compositions can be used in conjunction with chemotherapy. Additionally, combination immunotherapy may be used to direct two distinct cytotoxic effector populations toward tumor cell rejection. For example, anti-CD70 antibodies linked to anti-Fc-gamma RI or anti-CD3 may be used in conjunction with IgG- or IgA-receptor specific binding agents.

Bispecific and multispecific molecules of the disclosure can also be used to modulate FcγR or FcγR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the disclosure which have complement binding sites, such as portions from IgG1, -2 or -3 or IgM which bind complement, can also be used in the presence of complement. In one embodiment, ex vivo treatment of a population of cells comprising target cells with a binding agent of the disclosure and appropriate effector cells can be supplemented by the addition of complement or serum containing complement. Phagocytosis of target cells coated with a binding agent of the disclosure can be improved by binding of complement proteins. In another embodiment target cells coated with the compositions (e.g., human antibodies, multispecific and bispecific molecules) of the disclosure can also be lysed by complement. In yet another embodiment, the compositions of the disclosure do not activate complement.

The compositions (e.g., human antibodies, multispecific and bispecific molecules and immunoconjugates) of the disclosure can also be administered together with complement. Accordingly, within the scope of the disclosure are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the disclosure and the complement or serum can be administered separately.

Also within the scope of the present disclosure are kits comprising the antibody compositions of the disclosure (e.g., human antibodies, bispecific or multispecific molecules or immunoconjugates) and instructions for use. The kit can further contain one or more additional reagents, such as an immunosuppressive reagent, a cytotoxic agent or a radiotoxic agent or one or more additional human antibodies of the disclosure (e.g., a human antibody having a complementary activity which binds to an epitope in the CD70 antigen distinct from the first human antibody).

Accordingly, patients treated with antibody compositions of the disclosure can be additionally administered (prior to, simultaneously with or following administration of a human antibody of the disclosure) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ) and tumor necrosis factor (TNF).

The compositions (e.g., human antibodies, multispecific and bispecific molecules) of the disclosure can also be used to target cells expressing FcγR or CD70, for example for labeling such cells. For such use, the binding agent can be linked to a molecule that can be detected. Thus, the disclosure provides methods for localizing ex vivo or in vitro cells expressing Fc receptors, such as FcγR or CD70. The detectable label can be, e.g., a radioisotope, a fluorescent compound, an enzyme or an enzyme co-factor.

In a particular embodiment, the disclosure provides methods for detecting the presence of CD70 antigen in a sample or measuring the amount of CD70 antigen, comprising contacting the sample and a control sample, with a human monoclonal antibody or an antigen binding portion thereof, which specifically binds to CD70, under conditions that allow for formation of a complex between the antibody or portion thereof and CD70. The formation of a complex is then detected, wherein a difference complex formation between the sample compared to the control sample is indicative the presence of CD70 antigen in the sample.

In yet another embodiment, immunoconjugates of the disclosure can be used to target compounds (e.g., therapeutic agents, labels, cytotoxins, radiotoxoins immunosuppressants, etc.) to cells which have CD70 cell surface receptors by linking such compounds to the antibody. For example, an anti-CD70 antibody can be conjugated to any of the toxin compounds described in U.S. Pat. Nos. 6,281,354 and 6,548,530, US patent publication Nos. 20030050331, 20030064984, 20030073852 and 20040087497 or published in WO 03/022806, which are hereby incorporated by reference in their entireties. Thus, the disclosure also provides methods for localizing ex vivo or in vivo cells expressing CD70 (e.g., with a detectable label, such as a radioisotope, a fluorescent compound, an enzyme or an enzyme co-factor). Alternatively, the immunoconjugates can be used to kill cells which have CD70 cell surface receptors by targeting cytotoxins or radiotoxins to CD70.

The present disclosure is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against CD70

Antigen

Immunization protocols utilized as antigen recombinant human CD70 fused with a dual myc-His tag. Alternatively, whole cell immunization using the renal carcinoma cell line 786-O (ATCC Accession No. CRL-1932) and boosted with the renal carcinoma cell line A-498 (ATCC Accession No. HTB-44) was used in some immunizations.

Transzenic HuMAb Mouse® and KM Mouse®

Fully human monoclonal antibodies to CD70 were prepared using the HCo7, HCo12 and HCo17 strains of HuMab transgenic mice and the KM strain of transgenic transchromosomic mice, each of which express human antibody genes. In these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al. (1996) *Nature Biotechnology* 14:845-851 and a human heavy chain transgene, HCo7, HCo 12 or HCo 17 as described in Example 2 of PCT Publication WO 01/09187. The KM Mouse® strain contains the SC20 transchromosome as described in PCT Publication WO 02/43478.

HuMab and KM Immunizations:

To generate fully human monoclonal antibodies to CD70, mice of the HuMAb Mouse® and KM Moused were immunized with recombinant human CD70 as antigen or whole cells expressing CD70 on the cell surface. General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen. 5-10×10$^6$ cells were used to immunize the HuMab mice intraperitonealy (IP), subcutaneously (Sc) or via footpad injection.

Transgenic mice were immunized twice with antigen in complete Freund's adjuvant or Ribi adjuvant IP, followed by 3-21 days IP (up to a total of 11 immunizations) with the antigen in incomplete Freund's or Ribi adjuvant. The immune response was monitored by retroorbital bleeds. The plasma was screened by ELISA and FACS (as described below) and mice with sufficient titers of anti-CD70 human immunogolobulin were used for fusions. Mice were boosted intravenously with antigen 3 days before sacrifice and removal of the spleen. Typically, 10-35 fusions for each antigen were performed. Several dozen mice were immunized for each antigen.

Selection of a HuMab Mouse® or KM Mouse® Producing Anti-CD70 Antibodies:

To select a HuMab Mouse® or KM Mouse® producing antibodies that bound CD70, sera from immunized mice were screened by flow cytometry for binding to a cell line expressing recombinant human CD70, but not to a control cell line that does not express CD70. In addition, the sera were screened by flow cytometry for binding to 786-O or A-498 cells. Briefly, the binding of anti-CD70 antibodies was assessed by incubating CD70-expressing CHO cells, 786-O cells or A498 cells with the anti-CD70 antibody at 1:20 dilution. The cells were washed and binding was detected with a FITC-labeled anti-human IgG Ab. Flow cytometric analyses were performed using a FACSCalibur flow cytometry (Becton Dickinson, San Jose, Calif.). Antibodies that bound to the CD70 expressing CHO cells but not the non-CD70 expressing parental CHO cells were further tested for binding to CD70 by ELISA, as described by Fishwild, D. et al. (1996). Briefly, microtiter plates were coated with purified recombinant CD70 fusion protein from transfected CHO cells at 1-2 µg/ml in PBS, 100 µl/wells incubated 4° C. overnight then blocked with 200 µl/well of 5% chicken serum in PBS/Tween (0.05%). Dilutions of sera from CD70-immunized mice were added to each well and incubated for 1-2 hours at ambient temperature. The plates were washed with PBS/Tween and then incubated with a goat-anti-human IgG polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-CD70 antibodies were used for fusions. Fusions were performed as described below and hybridoma supernatants were tested for anti-CD70 activity by ELISA.

Generation of Hybridomas Producing Human Monoclonal Antibodies to CD70:

The mouse splenocytes, isolated from a HuMab Mouse® and/or a KM Mouse®, were fused to a mouse myeloma cell line either using PEG based upon standard protocols or electric field based electrofusion using a Cyto Pulse large chamber cell fusion electroporator (Cyto Pulse Sciences, Inc., Glen Burnie, Md.). The resulting hybridomas were then screened for the production of antigen-specific antibodies. Single cell suspensions of splenocytes from immunized mice were fused to one-fourth the number of SP2/0 nonsecreting mouse myeloma cells (ATCC, CRL 1581) with 50% PEG (Sigma). Cells were plated at approximately $1\times10^5$/well in flat bottom microtiter plate, followed by a one week incubation in DMEM high glucose medium with L-glutamine and sodium pyruvate (Mediatech, Inc., Herndon, Va.) and further containing 10% fetal Bovine Serum (Hyclone, Logan, Utah), 18% P388D1 conditional media, 5% Origen Hybridoma cloning factor (BioVeris, Gaithersburg, Va.), 4 mM L-glutamine, 5 mM HEPES, 0.055 mM β-mercaptoethanol, 50 units/ml penicillin, 50 mg/ml streptomycin and 1× Hypoxanthine-aminopterin-thymidine (HAT) media (Sigma; the HAT is added 24 hours after the fusion). After one week, cells cultured in medium in which HAT was used was replaced with HT. Individual wells were then screened by FACS or ELISA (described above) for human anti-CD70 monoclonal IgG antibodies. Once extensive hybridoma growth occurred, medium was monitored usually after 10-14 days. The antibody-secreting hybridomas were replated, screened again and, if still positive for human IgG, anti-CD70 monoclonal antibodies were subcloned at least twice by limiting dilution. The stable subclones were then cultured in vitro to generate small amounts of antibody in tissue culture medium for further characterization.

Hybridoma clones 2H5, 10B4, 8B5, 18E7 and 69A7, were selected for further analysis;

Example 2

Structural Characterization of Human Monoclonal Antibodies 2H5, 10B4, 8B5, 18E7 and 69A7

The cDNA sequences encoding the heavy and light chain variable regions of the 2H5, 10B4, 8B5, 18E7 and 69A7 monoclonal antibodies were obtained from the 2H5, 10B4, 8B5, 18E7 and 69A7 hybridomas, respectively, using standard PCR techniques and were sequenced using standard DNA sequencing techniques.

The nucleotide and amino acid sequences of the heavy chain variable region of 2H5 are shown in FIG. 1A and in SEQ ID NO:41 and 1, respectively.

The nucleotide and amino acid sequences of the light chain variable region of 2H5 are shown in FIG. 1B and in SEQ ID NO:46 and 6, respectively.

Comparison of the 2H5 heavy chain immunoglobulin sequence to the known human germline immunoglobulin heavy chain sequences demonstrated that the 2H5 heavy chain utilizes a VH segment from human germline VH 3-30.3, an undetermined D segment and a JH segment from human germline JH 4b. The alignment of the 2H5 VH sequence to the germline VH 3-30.3 sequence is shown in FIG. 6. Further analysis of the 2H5 VH sequence using the Kabat system of CDR region determination led to the delineation of the heavy chain CDR1, CDR2 and CDR3 regions as shown in FIGS. 1A and 6 and in SEQ ID NOs:11, 16 and 21, respectively.

Comparison of the 2H5 light chain immunoglobulin sequence to the known human germline immunoglobulin light chain sequences demonstrated that the 2H5 light chain utilizes a VL segment from human germline VK L6 and a JK segment from human germline JK 4. The alignment of the 2H5 VL sequence to the germline VK L6 sequence is shown in FIG. 9. Further analysis of the 2H5 VL sequence using the Kabat system of CDR region determination led to the delineation of the light chain CDR1, CDR2 and CDR3 regions as shown in FIGS. 1B and 9 and in SEQ ID NOs:26, 31 and 36, respectively.

The nucleotide and amino acid sequences of the heavy chain variable region of 10B4 are shown in FIG. 2A and in SEQ ID NO:42 and 2, respectively.

The nucleotide and amino acid sequences of the light chain variable region of 10B4 are shown in FIG. 2B and in SEQ ID NO:47 and 7, respectively.

Comparison of the 10B4 heavy chain immunoglobulin sequence to the known human germline immunoglobulin heavy chain sequences demonstrated that the 10B4 heavy chain utilizes a VH segment from human germline VH 3-30.3, a D segment from human germline 4-11 and a JH segment from human germline JH 4b. The alignment of the 10B4 VH sequence to the germline VH 3-30.3 sequence is shown in FIG. 6. Further analysis of the 10B4 VH sequence using the Kabat system of CDR region determination led to the delineation of the heavy chain CDR1, CDR2 and CDR3 regions as shown in FIGS. 2A and 6 and in SEQ ID NOs:12, 17 and 22, respectively.

Comparison of the 10B4 light chain immunoglobulin sequence to the known human germline immunoglobulin light chain sequences demonstrated that the 10B4 light chain utilizes a VL segment from human germline VK L18 and a JK segment from human germline JK 3. The alignment of the 10B4 VL sequence to the germline VK L18 sequence is shown in FIG. 10. Further analysis of the 10B4 VL sequence using the Kabat system of CDR region determination led to the delineation of the light chain CDR1, CDR2 and CDR3 regions as shown in FIGS. 2B and 10 and in SEQ ID NOs:27, 32 and 37, respectively.

The nucleotide and amino acid sequences of the heavy chain variable region of 8B5 are shown in FIG. 3A and in SEQ ID NO:43 and 3, respectively.

The nucleotide and amino acid sequences of the light chain variable region of 8B5 are shown in FIG. 3B and in SEQ ID NO:48 and 8, respectively.

Comparison of the 8B5 heavy chain immunoglobulin sequence to the known human germline immunoglobulin heavy chain sequences demonstrated that the 8B5 heavy chain utilizes a VH segment from human germline VH 3-33, a D segment from human germline 3-10 and a JH segment from human germline JH 4b. The alignment of the 8B5 VH sequence to the germline VH 3-33 sequence is shown in FIG. 7. Further analysis of the 8B5 VH sequence using the Kabat system of CDR region determination led to the delineation of the heavy chain CDR1, CDR2 and CDR3 regions as shown in FIGS. 3A and 7 and in SEQ ID NOs:13, 18 and 23, respectively.

Comparison of the 8B5 light chain immunoglobulin sequence to the known human germline immunoglobulin light chain sequences demonstrated that the 8B5 light chain utilizes a VL segment from human germline VK L15 and a JK segment from human germline JK 4. The alignment of the 8B5 VL sequence to the germline VK L15 sequence is shown in FIG. 11. Further analysis of the 8B5 VL sequence using the Kabat system of CDR region determination led to the delineation of the light chain CDR1, CDR2 and CDR3 regions as shown in FIGS. 3B and 11 and in SEQ ID NOs:28, 33 and 38, respectively.

The nucleotide and amino acid sequences of the heavy chain variable region of 18E7 are shown in FIG. 4A and in SEQ ID NO:44 and 4, respectively.

The nucleotide and amino acid sequences of the light chain variable region of 18E7 are shown in FIG. 4B and in SEQ ID NO:49 and 9, respectively.

Comparison of the 18E7 heavy chain immunoglobulin sequence to the known human germline immunoglobulin heavy chain sequences demonstrated that the 18E7 heavy chain utilizes a VH segment from human germline VH 3-33, a D segment from human germline 3-10 and a JH segment from human germline JH 4b. The alignment of the 18E7 VH sequence to the germline VH 3-33 sequence is shown in FIG. 7. Further analysis of the 18E7 VH sequence using the Kabat system of CDR region determination led to the delineation of the heavy chain CDR1, CDR2 and CDR3 regions as shown in FIGS. 4A and 7 and in SEQ ID NOs:14, 19 and 24, respectively.

Comparison of the 18E7 light chain immunoglobulin sequence to the known human germline immunoglobulin light chain sequences demonstrated that the 18E7 light chain utilizes a VL segment from human germline VK L15 and a JK segment from human germline JK 4. The alignment of the 18E7 VL sequence to the germline VK L15 sequence is shown in FIG. 11. Further analysis of the 18E7 VL sequence using the Kabat system of CDR region determination led to the delineation of the light chain CDR1, CDR2 and CDR3 regions as shown in FIGS. 4B and 11 and in SEQ ID NOs:29, 34 and 39, respectively.

The nucleotide and amino acid sequences of the heavy chain variable region of 69A7 are shown in FIG. 5A and in SEQ ID NO:45 and 5, respectively.

The nucleotide and amino acid sequences of the light chain variable region of 69A7 are shown in FIG. 5B and in SEQ ID NO:50 and 10, respectively.

Comparison of the 69A7 heavy chain immunoglobulin sequence to the known human germline immunoglobulin heavy chain sequences demonstrated that the 69A7 heavy chain utilizes a VH segment from human germline VH 4-61, a D segment from human germline 4-23 and a JH segment from human germline JH 4b. The alignment of the 69A7 VH sequence to the germline VH 4-61 sequence is shown in FIG. 8. Further analysis of the 69A7 VH sequence using the Kabat system of CDR region determination led to the delineation of the heavy chain CDR1, CDR2 and CDR3 regions as shown in FIGS. 5A and 9 and in SEQ ID NOs:15, 20 and 25, respectively.

Comparison of the 69A7 light chain immunoglobulin sequence to the known human germline immunoglobulin light chain sequences demonstrated that the 69A7 light chain utilizes a VL segment from human germline VK L6 and a JK segment from human germline JK 4. The alignment of the 69A7 VL sequence to the germline VK L6 sequence is shown in FIG. 12. Further analysis of the 69A7 VL sequence using the Kabat system of CDR region determination led to the delineation of the light chain CDR1, CDR2 and CDR3 regions as shown in FIGS. 5B and 12 and in SEQ ID NOs:30, 35 and 40, respectively.

Example 3

Characterization of Binding Specificity of Anti-CD70 Human Monoclonal Antibodies A comparison of anti-CD70 antibodies on binding to immunopurified CD70 was performed by standard ELISA to examine the specificity of binding for CD70.

Figure 13:
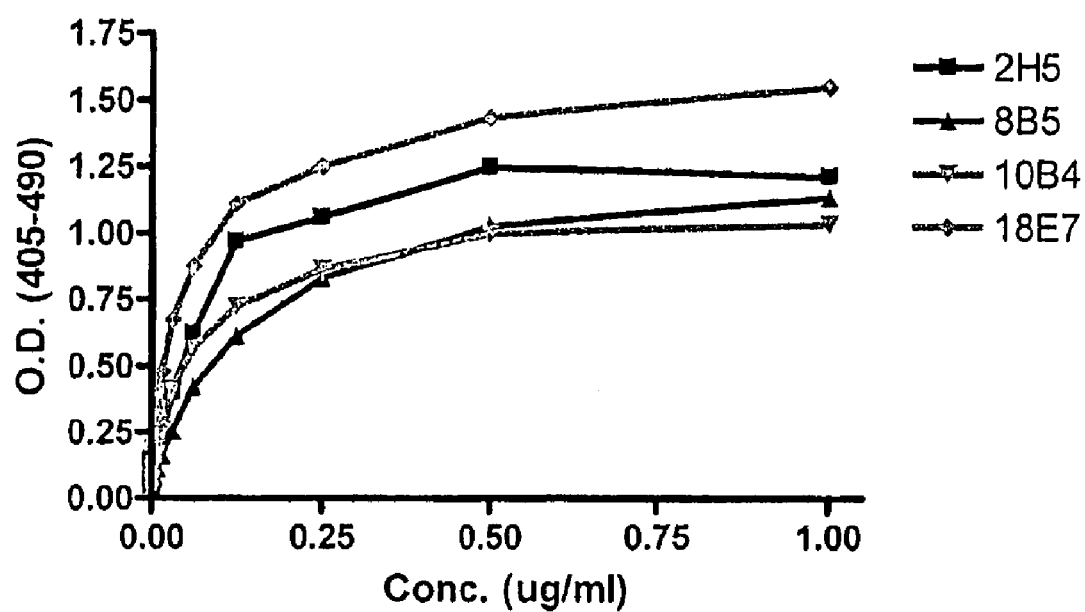
FIG. 13 shows the results of ELISA experiments demonstrating that human monoclonal antibodies against human CD70 specifically bind to CD70.

Recombinant myc-tagged CD70 was coated on a plate overnight., then tested for binding against the anti-CD70 human monoclonal antibodies 2H5, 10B4, 8B5, 18E7 and 69A7. Standard ELISA procedures were performed. The anti-CD70 human monoclonal antibodies were added at a concentration of 1 µg/ml and titrated down at 1:2 serial dilutions. Goat-anti-human IgG (Fc or kappa chain-specific) polyclonal antibody conjugated with horseradish peroxidase (HRP) was used as secondary antibody. The results are shown in FIG. 13. The anti-CD70 human monoclonal antibodies 2H5, 10B4, 8B5 and 18E7 bound with high specificity to CD70.

Example 4

Characterization of Anti-CD70 Antibody Binding to CD70 Expressed on the Surface of Renal Cancer Carcinoma Cell Lines Anti-CD70 antibodies were tested for binding to renal cell carcinoma cells expressing CD70 on their cell surface by flow cytometry.

Figure 14:
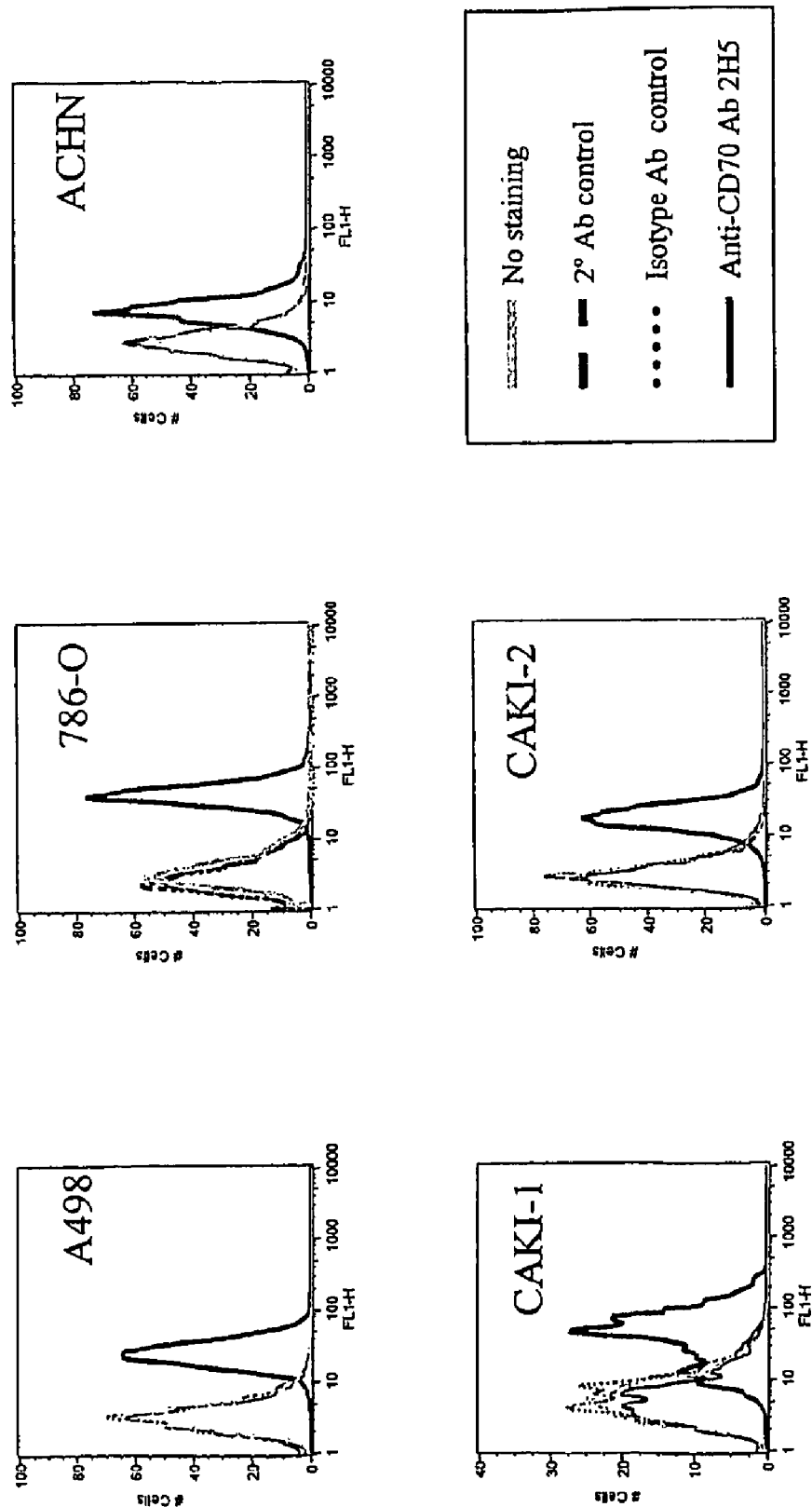
FIG. 14 shows the results of flow cytometry experiments demonstrating that the anti-CD70 human monoclonal antibody 2H5 binds to renal carcinoma cell lines.

The renal cell carcinoma cell lines A-498 (ATCC Accession No. HTB-44), 786-O (ATCC Accession No. CRL-1932), ACHN (ATCC Accession No. CRL-1611), Caki-1 (ATCC Accession No. HTB-46) and Caki-2 (ATCC Accession No. HTB-47) were each tested for antibody binding. Binding of the HuMAb 2H5 anti-CD70 human monoclonal antibody was assessed by incubating $1 \times 10^5$ cells with 2H5 at a concentration of 1 µg/ml. The cells were washed and binding was detected with a FITC-labeled anti-human IgG Ab. Flow cytometric analyses were performed using a FACSCalibur flow cytometry (Becton Dickinson, San Jose, Calif.). The results are shown in FIG. 14. The anti-CD70 monoclonal antibody 2H5 bound to the renal carcinoma cell lines A-498, 786-O, ACHN, Caki-1 and Caki-2.

Figure 15A:
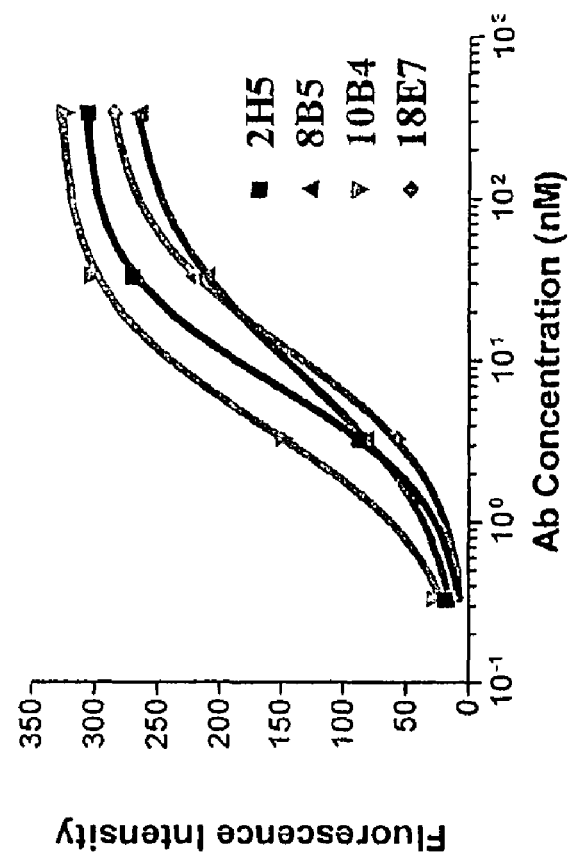
FIGS. 15A and B show the results of flow cytometry experiments demonstrating that human monoclonal antibodies against human CD70 bind in a concentration dependent manner to renal cell carcinoma (RCC) cell lines. (A) 786-O RCC cell line (B) A498 RCC cell line.
Figure 15B:
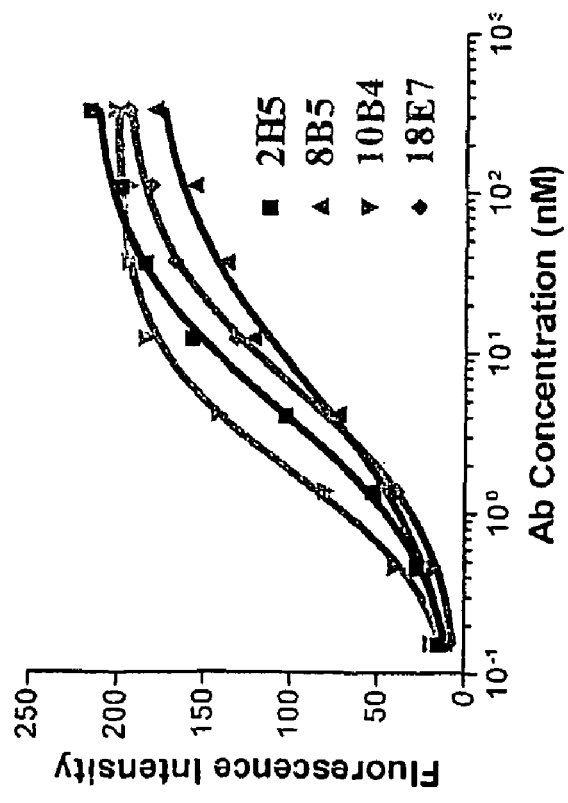
FIG. 15C shows the results of flow cytometry experiments demonstrating that human monoclonal antibodies against human CD70 bind to the renal carcinoma cell line 786-O.
FIG. 15D shows the results of flow cytometry experiments demonstrating that the HuMAb 69A7 antibody against human CD70 binds in a concentration dependent manner to renal cell carcinoma (RCC) cell lines.

The renal cell carcinoma cell lines 786-O and A-498 were tested for binding of the HuMAb anti-CD70 human monoclonal antibodies 2H5, 8B5, 10B4 and 18E7 at different concentrations. Binding of the anti-CD70 human monoclonal antibodies was assessed by incubating $5 \times 10^5$ cells with antibody at a starting concentration of 50 µg/ml and serially diluting the antibody at a 1:3 dilution. The cells were washed and binding was detected with a PE-labeled anti-human IgG Ab. Flow cytometric analyses were performed using a FACSCalibur flow cytometry (Becton Dickinson, San Jose, Calif.). The results are shown in FIG. 15A (786-O) and FIG. 15B (A-498). The anti-CD70 monoclonal antibodies 2H5, 8B5, 10B4 and 18E7 bound to the renal carcinoma cell lines 786-O and A-498 in a concentration dependent manner, as measured by the mean fluorescent intensity (MFI) of staining. The $EC_{50}$ values for the anti-CD70 monoclonal antibodies ranged from 1.844 nM to 6.669 nM for the 786-O cell line and 3.984 nM to 11.84 nM for the A-498 cell line.

Figure 15C:
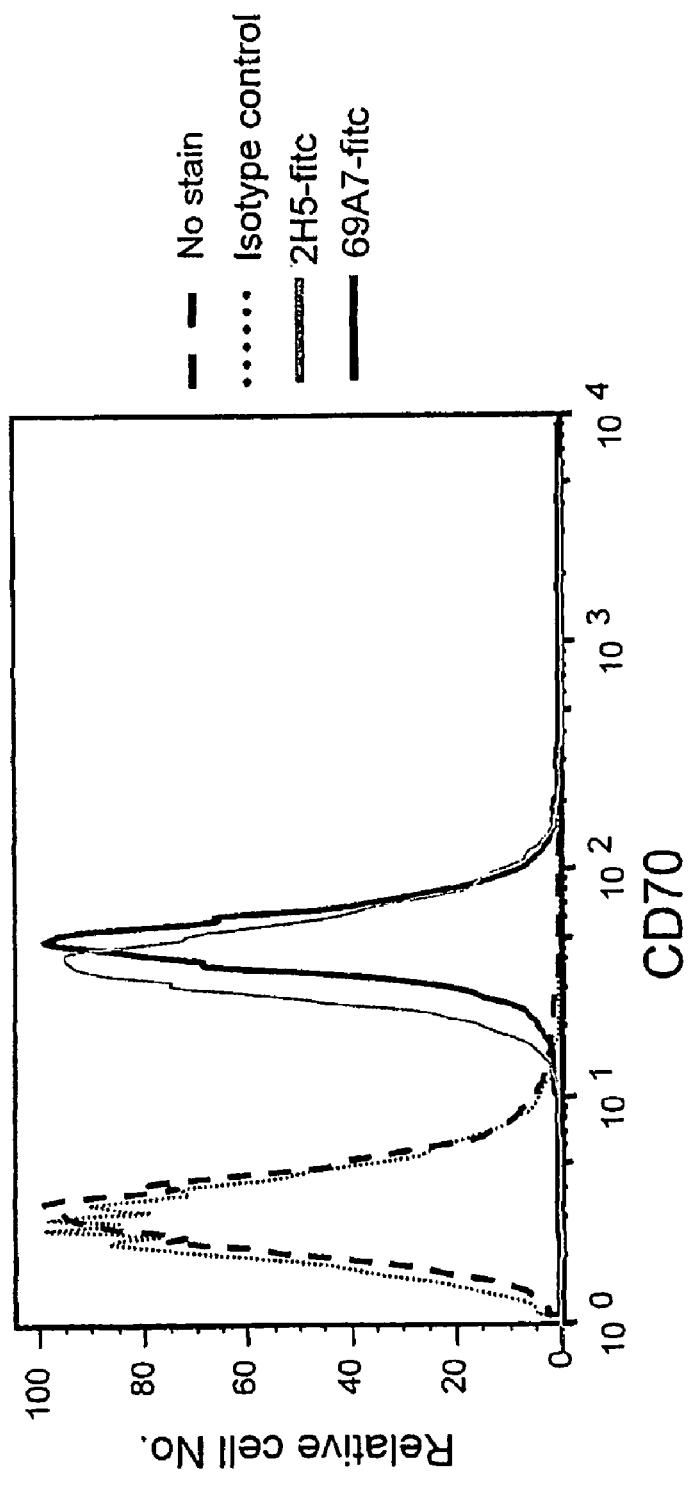

Binding of the HuMAb 2H5 and 69A7 anti-CD70 human monoclonal antibodies to the renal cell carcinoma cell line 786-O was assessed by incubating $2 \times 10^5$ cells with either 2H5 or 69A7 at a concentration of 10 µg/ml. An isotype control antibody was used as a negative control. The cells were washed and binding was detected with a FITC-labeled anti-human IgG Ab. Flow cytometric analyses were performed using a FACSCalibur flow cytometry (Becton Dickinson, San Jose, Calif.). The results are shown in FIG. 15C. Both anti-CD70 monoclonal antibodies bound to the renal carcinoma cell line 786-O.

Figure 15D:
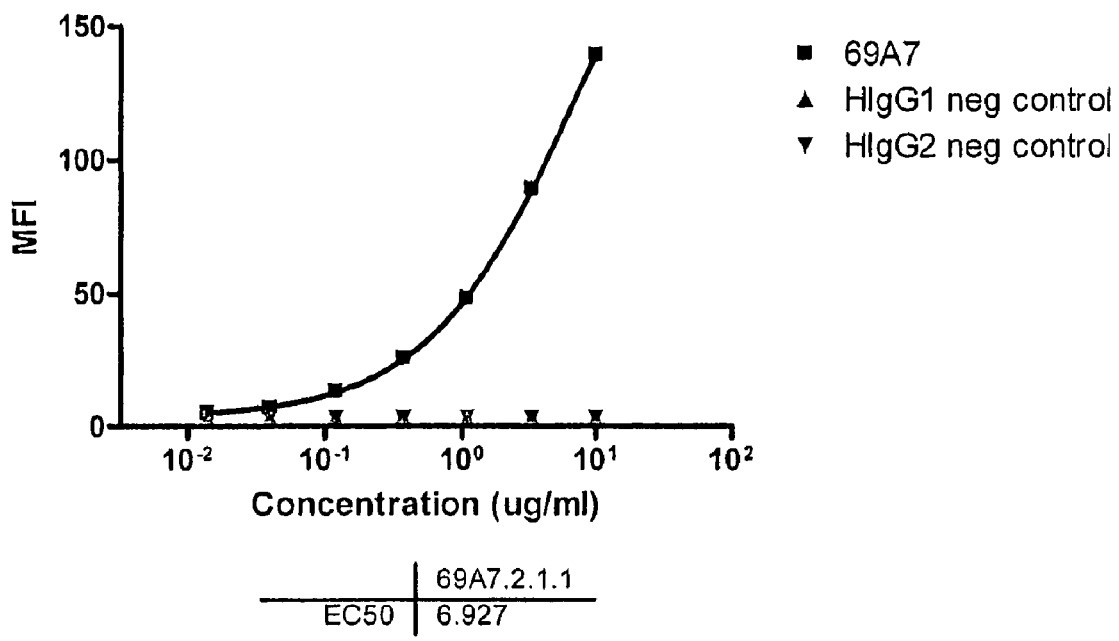

The renal cell carcinoma cell line 786-O was tested for binding of the HuMAb anti-CD70 human monoclonal antibody 69A7 at different concentrations. Binding of the anti-CD70 human monoclonal antibodies was assessed by incubating $5 \times 10^5$ cells with antibody at a starting concentration of 10 µg/ml and serially diluting the antibody at a 1:3 dilution. The cells were washed and binding was detected with a PE-labeled anti-human IgG Ab. Flow cytometric analyses were performed using a FACSCalibur flow cytometry (Becton Dickinson, San Jose, Calif.). The results are shown in FIG. 15D. The anti-CD70 monoclonal antibody 69A7 bound to the renal carcinoma cell line 786-O in a concentration dependent manner, as measured by the mean fluorescent intensity (MFI) of staining. The $EC_{50}$ value for the anti-CD70 monoclonal antibody 69A7 binding to 786-O cells was 6.927 nM.

These data demonstrate that the anti-CD70 HuMAbs bind to renal cell carcinoma cell lines.

Example 5

Characterization of Anti-CD70 Antibody Binding to CD70 Expressed on the Surface of Lymphoma Cell Lines Anti-CD70 antibodies were tested for binding to lymphoma cells expressing CD70 on their cell surface by flow cytometry.

Figure 16:
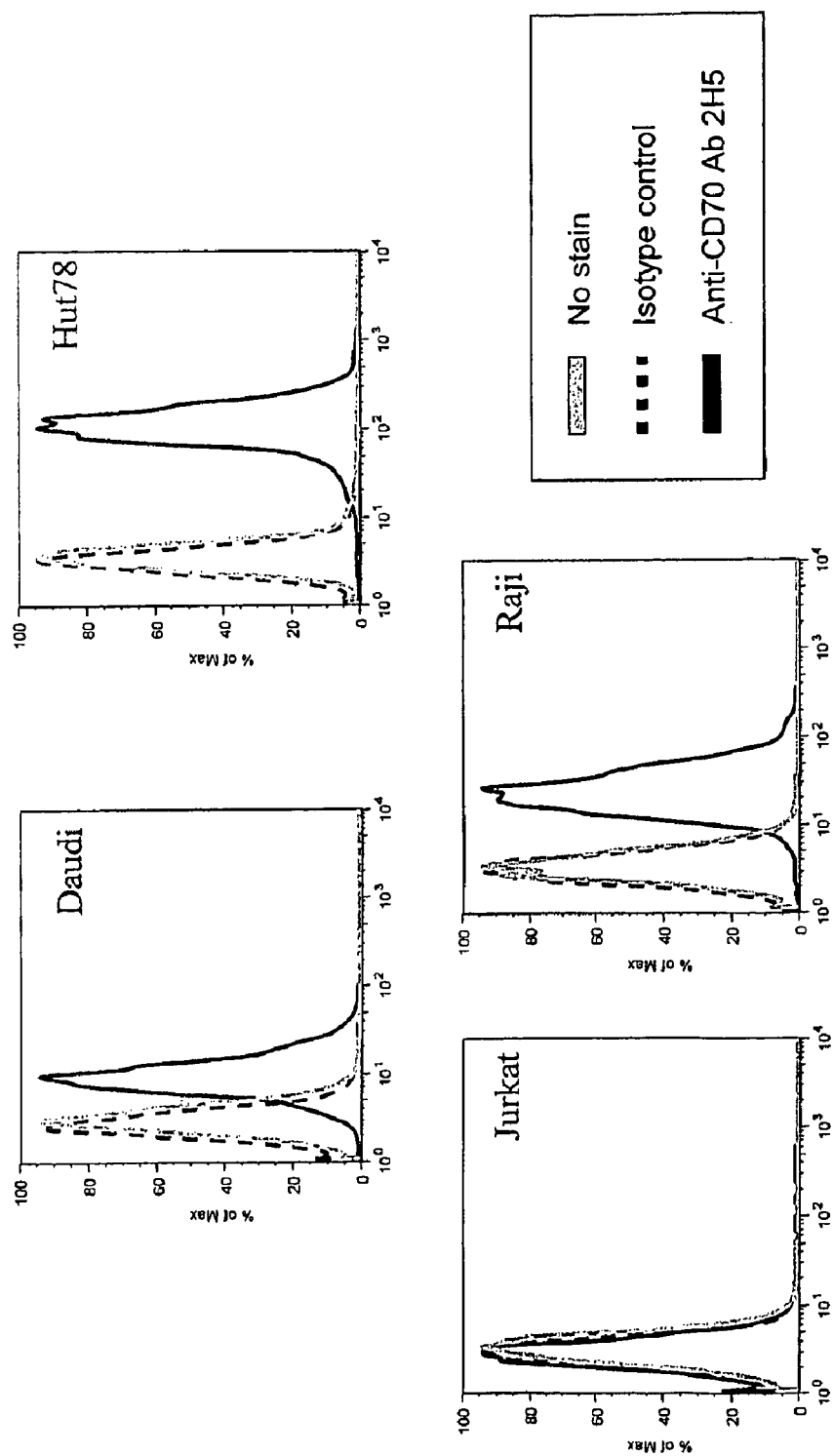
FIG. 16 shows the results of flow cytometry experiments demonstrating that the anti-CD70 human monoclonal antibody 2H5 binds to human lymphoma cell lines.

The lymphoma cell lines Daudi (ATCC Accession No. CCL-213), HuT 78 (ATCC Accession No. TIB-161) and Raji (ATCC Accession No. CCL-86) were each tested for antibody binding. Binding of the HuMAb 2H5 anti-CD70 human monoclonal antibody was assessed by incubating $1 \times 10^5$ cells with 2H5 at a concentration of 1 µg/ml. The cells were washed and binding was detected with a FITC-labeled anti-human IgG Ab. The Jurkat cell line, which does not express CD70 on the cell surface, was used as a negative control. Flow cytometric analyses were performed using a FACSCalibur flow cytometry (Becton Dickinson, San Jose, Calif.). The results are shown in FIG. 16. The anti-CD70 monoclonal antibody 2H5 bound to the lymphoma cell lines Daudi, HuT 78 and Raji, as measured by the mean fluorescent intensity (MFI) of staining.

Figure 17A:
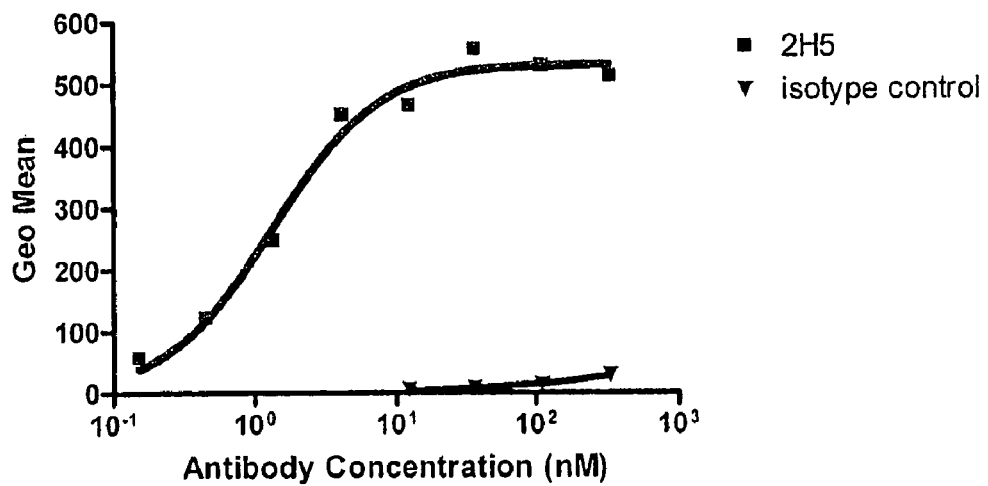
FIGS. 17A and B show the results of flow cytometry experiments demonstrating that the anti-CD70 human monoclonal antibody 2H5 binds to human lymphoma cell lines in a concentration dependent manner. (A) Raji lymphoma cell line (B) Granta-519 lymphoma cell line.
Figure 17B:
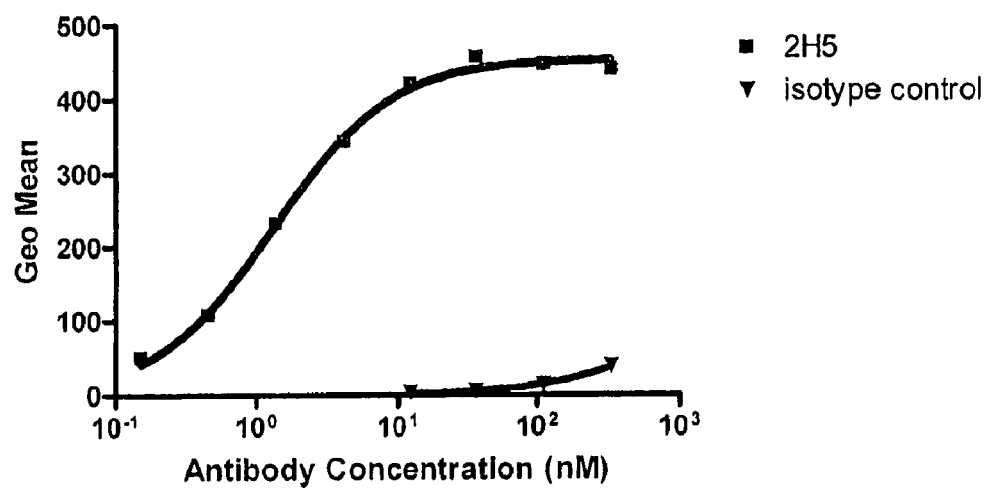
FIG. 17C shows the results of flow cytometry experiments demonstrating that human monoclonal antibodies against human CD70 bind to the Raji lymphoma cell line.
FIG. 17D shows the results of a competition flow cytometry assay demonstrating that the HuMAbs 2H5 and 69A7 share a similar binding epitope.
FIG. 17E shows the results of flow cytometry experiments demonstrating that human monoclonal antibodies against human CD70 bind to the Daudi lymphoma cell line and 786-O renal carcinoma cell line.

The lymphoma cell lines Raji and Granta 519 (DSMZ Accession No. 342) were tested for binding of the HuMAb anti-CD70 human monoclonal antibody 2H5 at varying concentrations. Binding of the anti-CD70 human monoclonal antibodies was assessed by incubating $5 \times 10^5$ cells with antibody at a starting concentration of 50 µg/ml and serially diluting the antibody at a 1:3 dilution. An isotype control antibody was used as a negative control. The cells were washed and binding was detected with a PE-labeled anti-human IgG Ab. Flow cytometric analyses were performed using a FACSCalibur flow cytometry (Becton Dickinson, San Jose, Calif.). The results are shown in FIGS. 17A (Raji) and 17B (Granta 519). The anti-CD70 monoclonal antibody 2H5 bound to the lymphoma cell lines Raji and Granta 519 in a concentration dependent manner, as measured by the mean fluorescent intensity (MFI) of staining. The $EC_{50}$ values for the anti-CD70 antibody were 1.332 nM for the Raji cells and 1.330 nM for the Granta 519 cells.

Figure 17C:
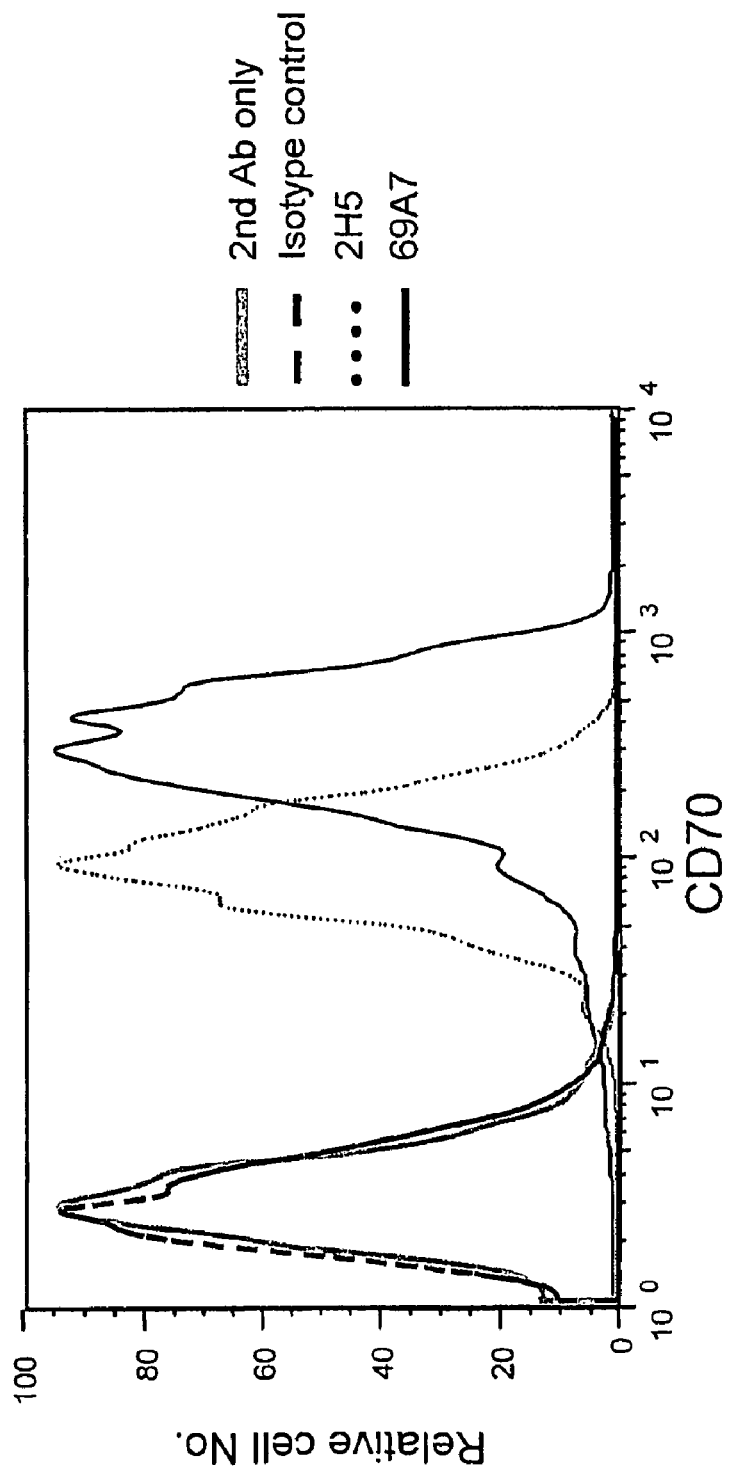

Binding of the HuMAbs 2H5 and 69A7 anti-CD70 human monoclonal antibodies to the Raji lymphoma cell line was assessed by incubating $2 \times 10^5$ cells with HuMAb at a concentration of 10 µg/ml. The cells were washed and binding was detected with a FITC-labeled anti-human IgG Ab. An isotype control antibody and secondary antibody alone were used as negative control. Flow cytometric analyses were performed using a FACSCalibur flow cytometry (Becton Dickinson, San Jose, Calif.). The results are shown in FIG. 17C. Both anti-CD70 monoclonal antibodies bound to the Raji lymphoma cell line, as measured by the mean fluorescent intensity (MFI) of staining.

Figure 17D:
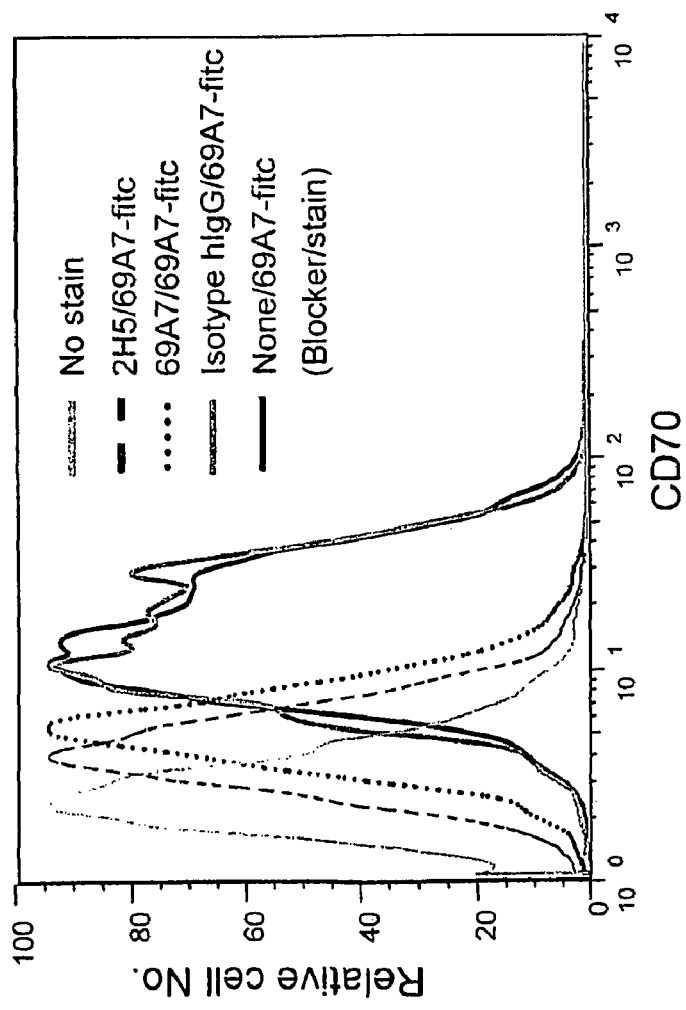

A competition FACS assay was carried out to elucidate the binding specificity of 69A7 against 2H5. Raji cells were incubated with either naked 69A7, 2H5, an isotype control antibody or no antibody at a concentration of 10 µg/ml. After wash, the cells were incubated with FITC-conjugated 69A7 at a concentration of 10 µg/ml. The cells were washed and binding was detected with a FITC-labeled anti-human IgG Ab. Flow cytometric analyses were performed using a FACSCalibur flow cytometry (Becton Dickinson, San Jose, Calif.). The results are shown in FIG. 17D. Both the anti-CD70 antibody 69A7 and 2H5 blocked binding of FITC-labelled 69A7, indicating that both 2H5 and 69A7 share a similar binding epitope.

Figure 17E:
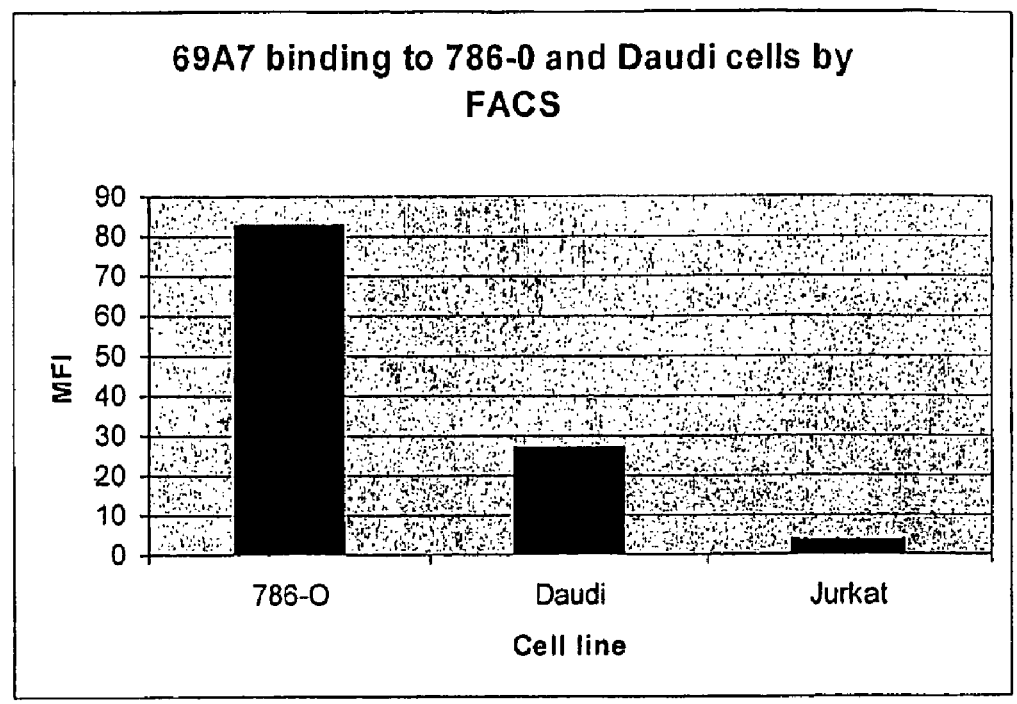

The Daudi lymphoma cell line and 786-O renal carcinoma cell were further tested for antibody binding. Binding of the HuMAb 69A7 anti-CD70 human monoclonal antibody was assessed by incubating $2 \times 10^5$ cells with 69A7 at a concentration of 1 µg/ml. The cells were washed and binding was detected with a FITC-labeled anti-human IgG Ab. The Jurkat cell line, which does not express CD70 on the cell surface, was used as a negative control. Flow cytometric analyses were performed using a FACSCalibur flow cytometry (Becton Dickinson, San Jose, Calif.). The results are shown in FIG. 17E. The anti-CD70 monoclonal antibody 69A7 bound to the Daudi lymphoma cell line and 786-O renal carcinoma cell line, as measured by the mean fluorescent intensity (MFI) of staining.

These data demonstrate that the anti-CD70 HuMAbs bind to lymphoma cell lines.

Example 6

Scatchard Analysis of Binding Affinity of Anti-CD70 Monoclonal Antibodies

The binding affinity of the 2H5, 8B5, 10B4 and 18E7 monoclonal antibodies was tested for binding affinity to a CD70 transfected CHO cell line using a Scatchard analysis.

CHO cells were transfected with full length CD70 using standard techniques and grown in RPMI media containing 10% fetal bovine serum (FBS). The cells were trypsinized and washed once in Tris based binding buffer (24 mM Tris pH 7.2, 137 mM NaCl, 2.7 mM KCl, 2 mM Glucose, 1 mM $CaCl_2$, 1 mM $MgCl_2$, 0.1% BSA) and the cells were adjusted to $2\times10^6$ cells/ml in binding buffer. Millipore plates (MAFB NOB) were coated with 1% nonfat dry milk in water and stored a 4° C. overnight. The plates were washed three times with 0.2 ml of binding buffer. Fifty microliters of buffer alone was added to the maximum binding wells (total binding). Twenty-five microliters of buffer alone was added to the control wells (non-specific binding). Varying concentration of $^{125}$-anti-CD70 antibody was added to all wells in a volume of 25 µl. Varying concentrations of unlabeled antibody at 100 fold excess was added in a volume of 25 µl to control wells and 25 µl of CD70 transfected CHO cells ($2\times10^6$ cells/ml) in binding buffer were added to all wells. The plates were incubated for 2 hours at 200 RPM on a shaker at 4° C. At the completion of the incubation the Millipore plates were washed three times with 0.2 ml of cold wash buffer (24 mM Tris pH 7.2, 500 mM NaCl, 2.7 mM KCl, 2 mM Glucose, 1 mM $CaCl_2$, 1 mM $MgCl_2$, 0.1% BSA.). The filters were removed and counted in a gamma counter. Evaluation of equilibrium binding was performed using single site binding parameters with the Prism software (San Diego, Calif.).

Using the above scatchard binding assay, the $K_D$ of the antibody for CD70 transfected CHO cells was approximately 2.1 nM for 2H5, 5.1 nM or 8B5, 1.6 nM for 10B4 and 1.5 nM for 18E7.

Example 7

Internalization of Anti-CD70 Monoclonal Antibody

Anti-CD70 HuMAbs were tested for the ability to internalize into CD70-expressing renal carcinoma cells using a Hum-Zap internalization assay. The Hum-Zap assay tests for internalization of a primary human antibody through binding of a secondary antibody with affinity for human IgG conjugated to the toxin saporin.

Figure 18:
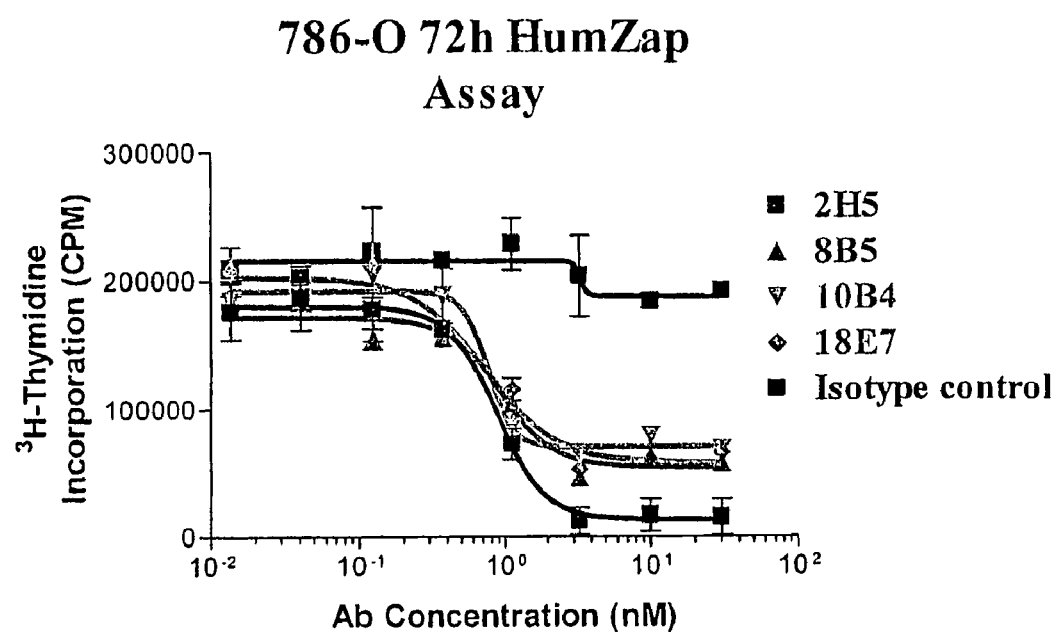
FIG. 18 shows the results of Hum-Zap internalization experiments demonstrating that human monoclonal antibodies against human CD70 can internalize into CD70+ cells.

The CD70-expressing renal carcinoma cancer cell line 786-O was seeded at $1.25\times10^4$ cells/well in 100 µl wells overnight. The anti-CD70 HuMAb antibodies 2H5, 8B5, 10B4 or 18E7 were added to the wells at a starting concentration of 30 nM and titrated down at 1:3 serial dilutions. An isotype control antibody that is non-specific for CD70 was used as a negative control. The Hum-Zap (Advanced Targeting Systems, San Diego, Calif., IT-22-25) was added at a concentration of 11 nM and plates were allowed to incubate for 72 hours. The plates were then pulsed with 1.0 µCi of $^3$H-thymidine for 24 hours, harvested and read in a Top Count Scintillation Counter (Packard Instruments, Meriden, Conn.). The results are shown in FIG. 18. The anti-CD70 antibodies 2H5, 8B5, 10B4 and 18E7 showed an antibody concentration dependent decrease in $^3$H-thymidine incorporation in CD70-expressing 786-O renal carcinoma cancer cells. The $EC_{50}$ value for the anti-CD70 antibody 2H5 was 0.9424 nM. This data demonstrates that the anti-CD70 antibodies 2H5, 8B5, 10B4 and 18E7 internalize into a renal carcinoma cancer cell line.

Example 8

Assessment of Cell Killing of a Toxin-Conjugated Anti-CD70 Antibody on Renal Cell Carcinoma Cell Lines In this example, anti-CD70 monoclonal antibodies conjugated to a toxin were tested for the ability to kill CD70+ renal cell carcinoma cell lines in a cell proliferation assay.

Figure 19:
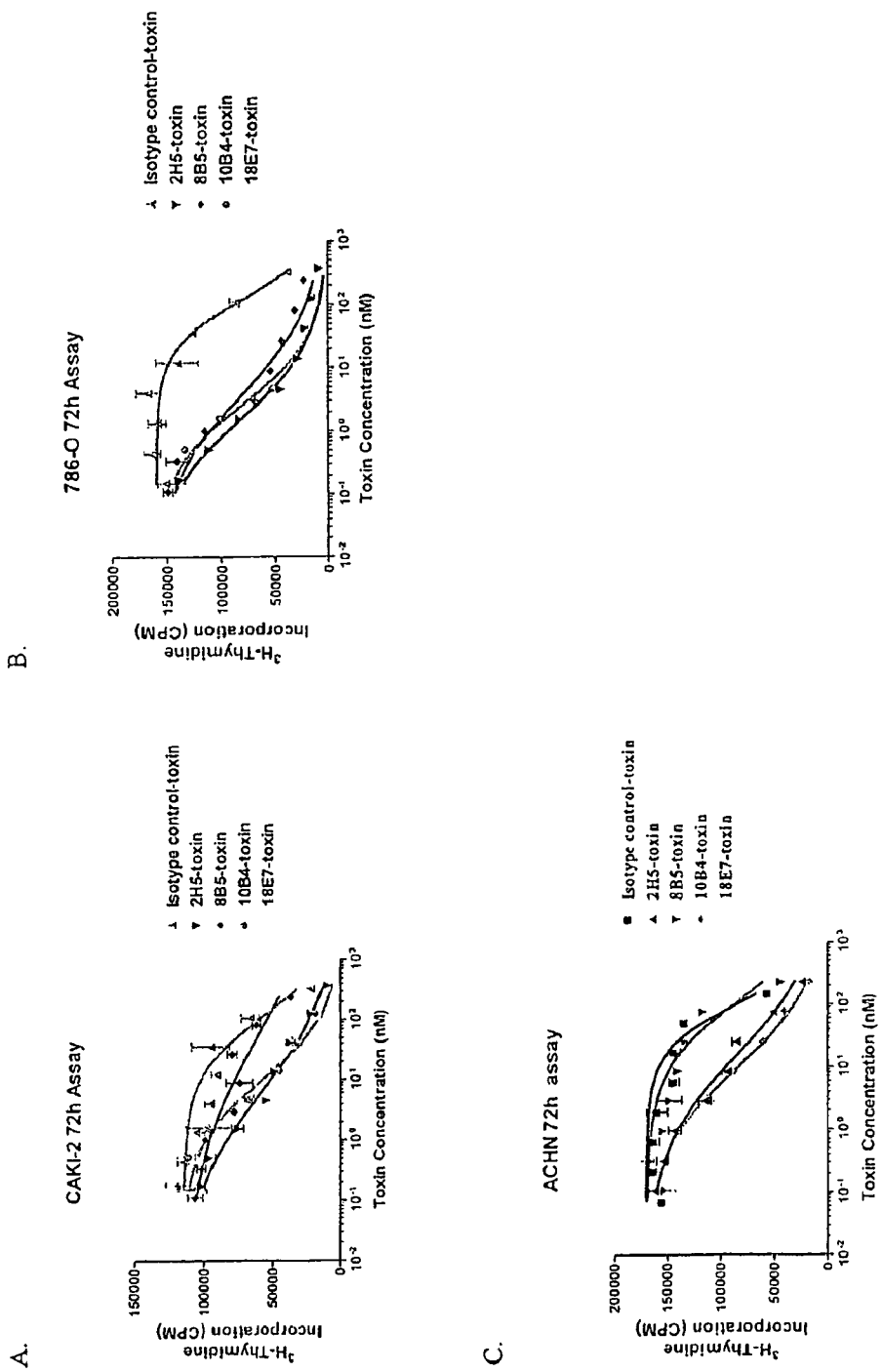
FIGS. 19A-C show the results of cell proliferation assays demonstrating that toxin-conjugated human monoclonal anti-CD70 antibodies kill renal cell carcinoma cell (RCC) lines. (A) Caki-2 RCCs (B) 786-O RCCs (C) ACHN RCCs.
Figure 20A:
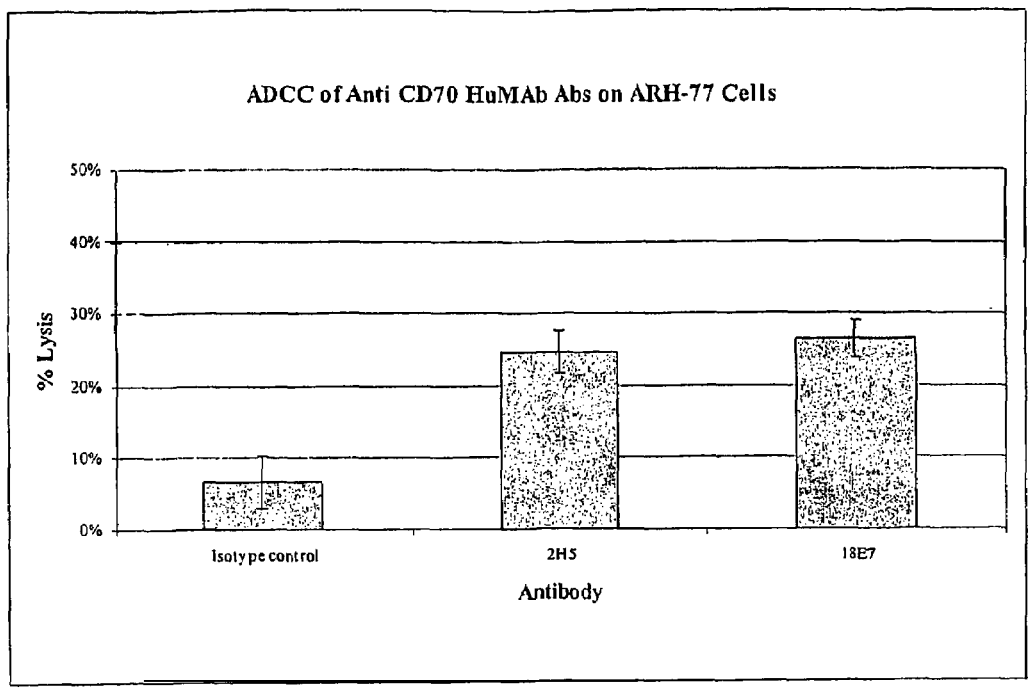
FIGS. 20A-D show the results of antibody dependent cellular cytotoxicity (ADCC) assays demonstrating that human monoclonal anti-CD70 antibodies kill human leukemia and lymphoma cell lines in an ADCC dependent manner. (A) ARH-77 leukemia cell line (B) HuT 78 lymphoma cell line (C) Raji lymphoma cell line and (D) L-540 cell line which does not express CD70.
Figure 20B:
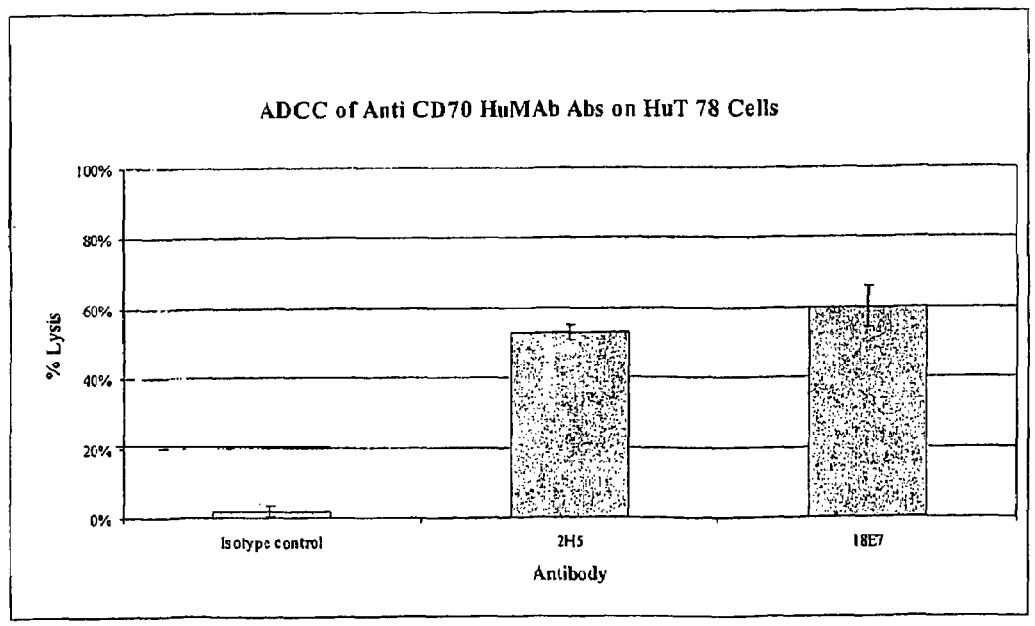
Figure 20C:
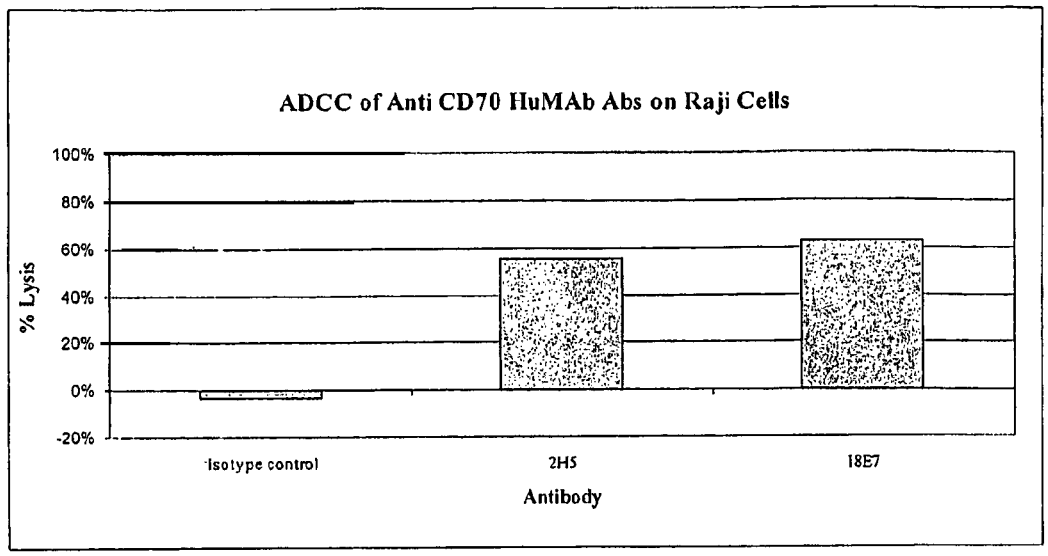
Figure 20D:
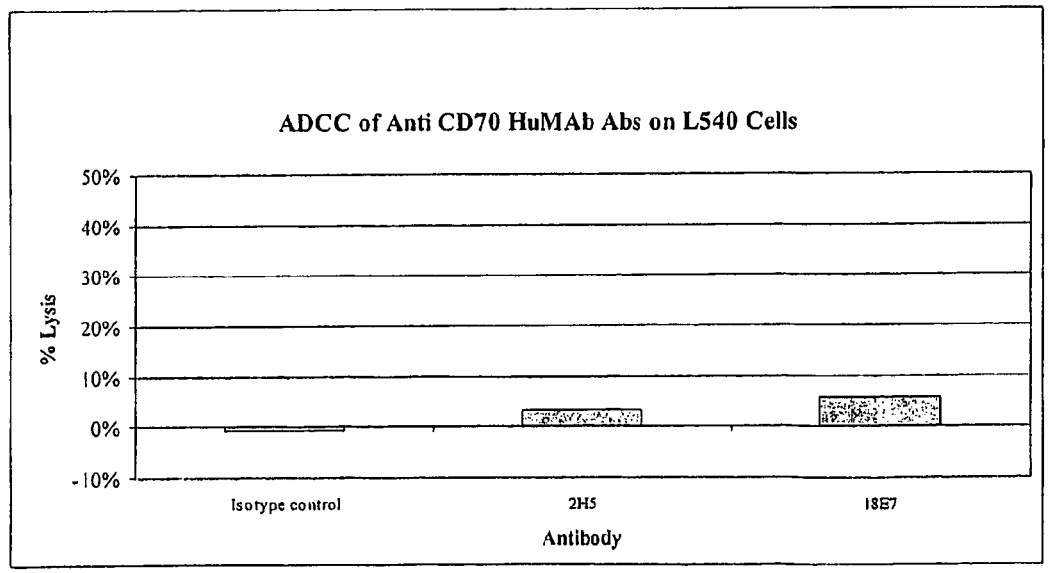

The anti-CD70 HuMAb antibodies 2H5, 8B5, 10B4 or 18E7 were conjugated to a toxin via a linker, such as a peptidyl, hydrazone or disulfide linker. The CD70-expressing renal carcinoma cancer cell lines ACHN and Caki-2 were seeded at $2.5\times10^4$ cells/wells and the CD70-expressing renal carcinoma cancer cell line 786-O was seeded at $1.25\times10^4$ cells/wells in 100 µl wells for 3 hours. An anti-CD70 antibody-toxin conjugate was added to the wells at a starting concentration of 30 nM and titrated down at 1:3 serial dilutions. An isotype control antibody that is non-specific for CD70 was used as a negative control. Plates were allowed to incubate for 69 hours. The plates were then pulsed with 1.0 µCi of $^3$H-thymidine for 24 hours, harvested and read in a Top Count Scintillation Counter (Packard Instruments, Meriden, Conn.). The results are shown in FIGS. 19A (Caki-2), 19B (786-O) and 19C (ACHN). The anti-CD70 antibodies 2H5, 8B5, 10B4 and 18E7 showed an antibody-toxin concentration dependent decrease in $^3$H-thymidine incorporation in CD70-expressing Caki-2, 786-O and ACHN renal carcinoma cancer cells. The $EC_{50}$ values for the anti-CD70 antibodies ranged from 6.728 nM to 76.05 nM in the CAKI-2 cells, 1.635 nM to 3.940 nM in the 786-O cells and 9.406 nM to 108.5 nM in the ACHN cells. This data demonstrates that the anti-CD70 antibodies 2H5, 8B5, 10B4 and 18E7 are cytotoxic to renal carcinoma cancer cells when conjugated to a toxin.

Example 9

Assessment of ADCC Activity of Anti-CD70 Antibody

In this example, anti-CD70 monoclonal antibodies were tested for the ability to kill CD70+ cell lines in the presence of effector cells via antibody dependent cellular cytotoxicity (ADCC) in a fluorescence cytotoxicity assay.

Human effector cells were prepared from whole blood as follows. Human peripheral blood mononuclear cells were purified from heparinized whole blood by standard Ficoll-paque separation. The cells were resuspended in RPMI1640 media containing 10% FBS and 200 U/ml of human IL-2 and incubated overnight at 37° C. The following day, the cells were collected and washed four times in culture media and resuspended at $2\times10^7$ cells/ml. Target CD70+ cells were incubated with BATDA reagent (Perkin Elmer, Wellesley, Mass.) at 2.5 µl BATDA per $1\times10^6$ target cells/mL for 20 minutes at 37° C. The target cells were washed four times, spun down and brought to a final volume of $1\times10^5$ cells/ml.

The CD70+ cell lines ARH-77 (human B lymphoblast leukemia; ATCC Accession No. CRL-1621), HuT 78 (human cutaneous lymphocyte lymphoma; ATCC Accession No. TIB-161), Raji (human B lymphocyte Burkitt's lymphoma; ATCC Accession No. CCL-86) and a negative control cell line L540 (human Hodgkin's lymphoma; DSMZ Deposit No. ACC 72) were tested for antibody specific ADCC to the human anti-CD70 monoclonal antibodies using the Delfia fluorescence emission analysis as follows. Each target cell line (100 µl of labeled target cells) was incubated with 50 µl of effector cells and 50 µl of antibody. A target to effector ratio of 1:50 was used throughout the experiments. In all studies, a human IgG1 isotype control was used as a negative control. Following a 2000 rpm pulse spin and one hour incubation at 37° C., the supernatants were collected, quick spun again and 20 µl of supernatant was transferred to a flat bottom plate, to which 180 µl of Eu solution (Perkin Elmer, Wellesley, Mass.) was added and read in a RubyStar reader (BMG Labtech). The % lysis was calculated as follows: (sample release−spontaneous release*100)/(maximum release−spontaneous release), where the spontaneous release is the fluorescence from wells which only contain target cells and maximum release is the fluorescence from wells containing target cells and have been treated with 2% Triton-X. Cell cytotoxicity % lysis for the ARH-77, HuT 78, Raji and L-540 cell lines are shown in FIGS. 20A-D, respectively. Each of the CD70+ expressing cell lines ARH-77, HuT 78 and Raji showed antibody mediated cytotoxicity with the HuMAb anti-CD70 antibodies 2H5 and 18E7, while the negative control cell line L-540 did not have appreciable cell cytotoxicity in the presence of anti-CD70 antibodies. This data demonstrates that HuMAb anti-CD70 antibodies show specific cytotoxicity to CD70+ expressing cells.

Example 10

Assessment of Cell Killing of a Toxin-Conjugated Anti-CD70 Antibody on Human Lymphoma Cell Lines In this example, anti-CD70 monoclonal antibodies conjugated to a toxin were tested for the ability to kill CD70+ human lymphoma cell lines in a cell proliferation assay.

Figure 21:
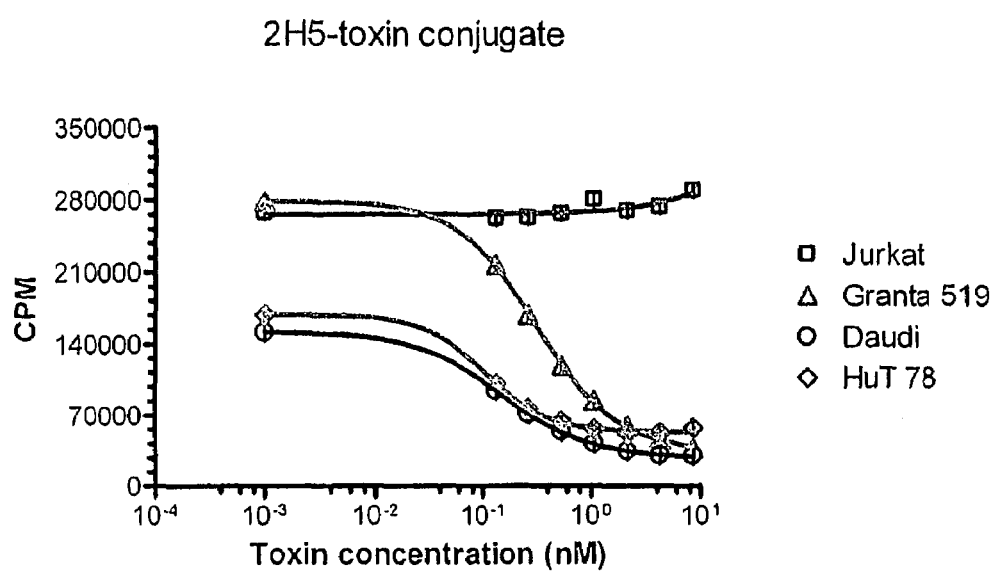
FIG. 21 shows the results of a cell proliferation assay demonstrating that toxin-conjugated human monoclonal anti-CD70 antibodies kill human lymphoma cell lines.

The anti-CD70 HuMAb antibody 2H5 was conjugated to a toxin via a linker, such as a peptidyl, hydrazone or disulfide linker. Examples of toxin compounds that may be conjugated to the antibodies of the current disclosure are described in the concurrently filed application filed on Sep. 26, 2005. The CD70-expressing human lymphoma cancer cell lines Daudi, HuT 78, Granta 519 and Raji were seeded at $10^5$ cells/well in 100 µl wells for 3 hours. An anti-CD70 antibody-toxin conjugate was added to the wells at a starting concentration of 30 nM and titrated down at 1:2 serial dilutions. The HuMAb antibody 2H5-toxin conjugate was also tested on Jurkat cells, a negative control cell line that does not express CD70 on the cell surface. Plates were allowed to incubate for 72 hours. The plates were then pulsed with 0.5 µCi of $^3$H-thymidine for 8 hours before termination of the culture, harvested and read in a Top Count Scintillation Counter (Packard Instruments). FIG. 21 showed the effects of the 2H5-conjugate on the Daudi, HuT 78, Granta 519 and Jurkat cells. The anti-CD70 antibody 2H5 showed an antibody-toxin concentration dependent decrease in $^3$H-thymidine incorporation in CD70-expressing Daudi, HuT 78 and Granta 519 B-cell lymphoma cancer cells, but not in the Jurkat cells.

Figure 22A:
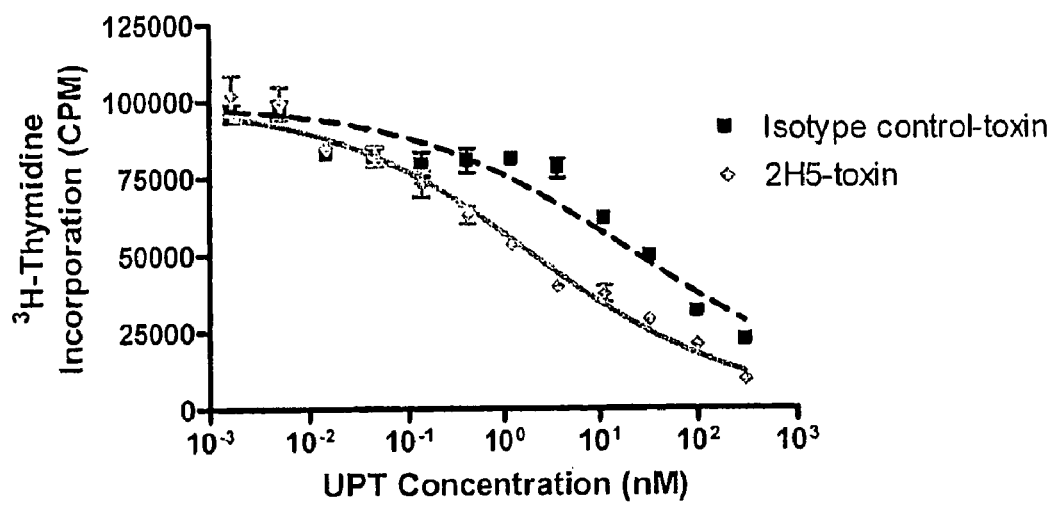
FIGS. 22A-B show the results of a cell proliferation assay demonstrating that toxin-conjugated human monoclonal anti-CD70 antibodies show cytotoxicity to Raji cells (A) with a three-hour wash and (B) with a continuous wash.
Figure 22B:
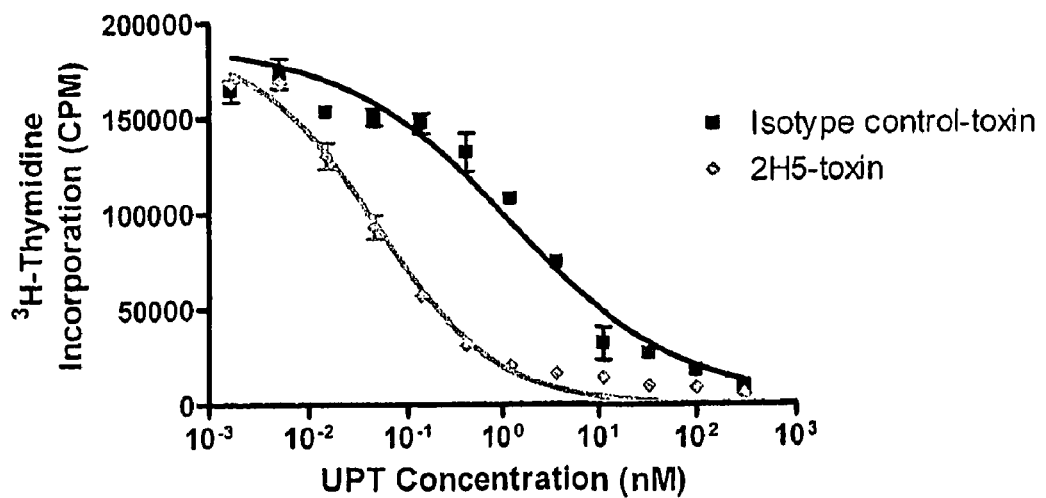

In a separate assay, the CD70-expressing human lymphoma cancer cell line Raji was seeded at $10^4$ cells/well in 100 µl wells for 3 hours. An anti-CD70 antibody-toxin conjugate was added to the wells at a starting concentration of 30 nM and titrated down at 1:3 serial dilutions. A toxin-conjugate isotype control antibody was used as a control. Plates were allowed to incubate for 72 hours with either a wash at 3 hours or a continuous wash. The plates were then pulsed with 0.5 µCi of $^3$H-thymidine for 8 hours before termination of the culture, harvested and read in a Top Count Scintillation Counter (Packard Instruments). FIGS. 22A and 22B showed an antibody-toxin concentration dependent decrease in $^3$H-thymidine incorporation on Raji cells with a 3 hour wash or with a continuous wash, respectively.

This data demonstrates that anti-CD70 antibodies conjugated to toxin show specific cytotoxicity to human lymphoma cancer cells.

Example 11

Treatment of In Vivo Tumor Xenograft Model Using Naked and Cytotoxin-Conjugated Anti-CD70 Antibodies Mice implanted with a renal cell carcinoma tumor were treated in vivo with toxin-conjugated anti-CD70 antibodies to examine the in vivo effect of the antibodies on tumor growth.

Figure 23A:
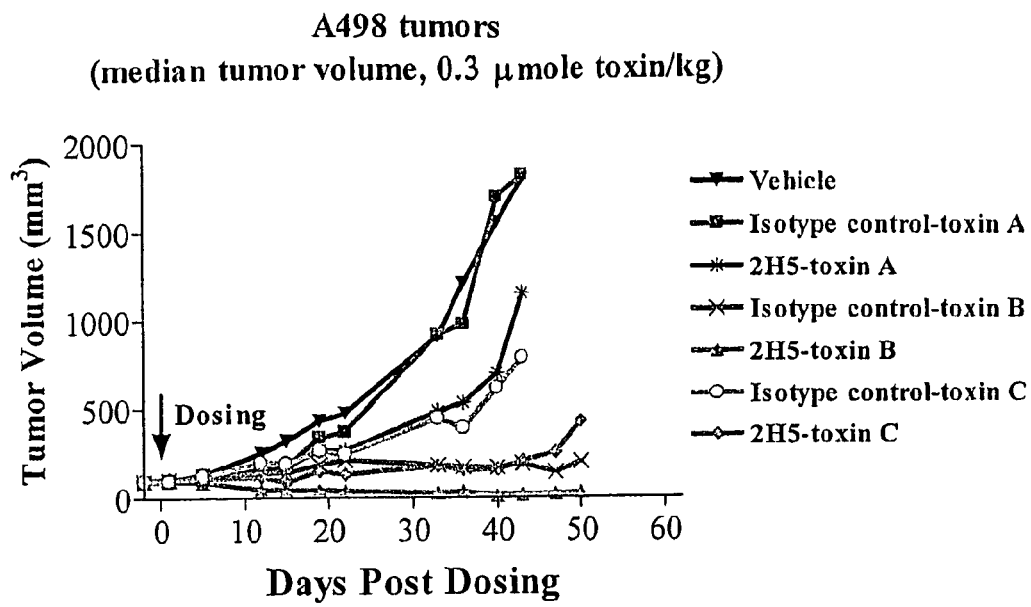
FIGS. 23A-B show the results of an in vivo mouse tumor model study demonstrating that treatment with the toxin conjugated anti-CD70 antibody 2H5 has a direct inhibitory effect on renal cell carcinoma (RCC) tumors in vivo. (A) A-498 RCC tumors (B) ACHN RCC tumors.
Figure 23B:
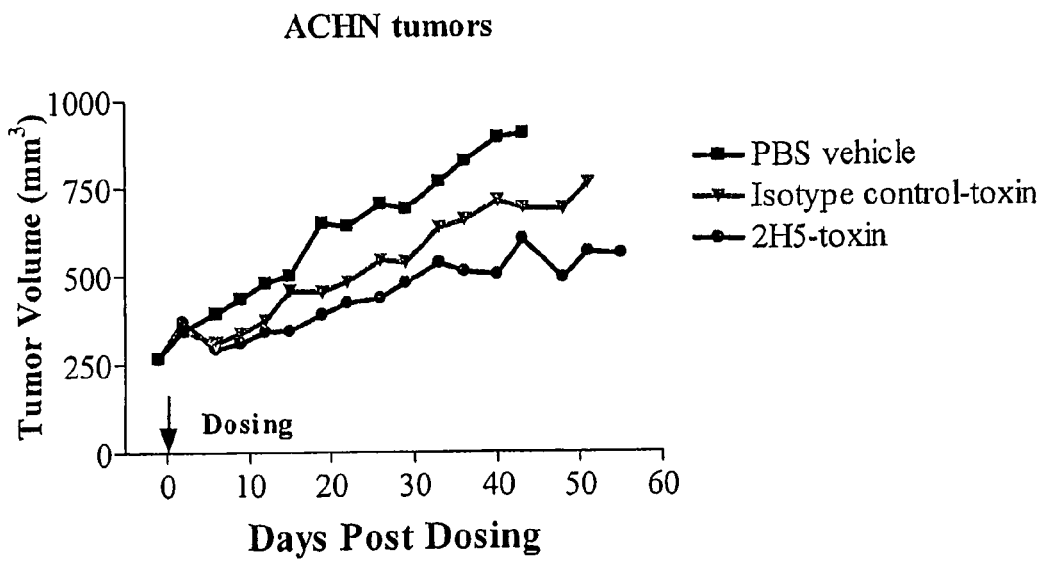
Figure 24A:
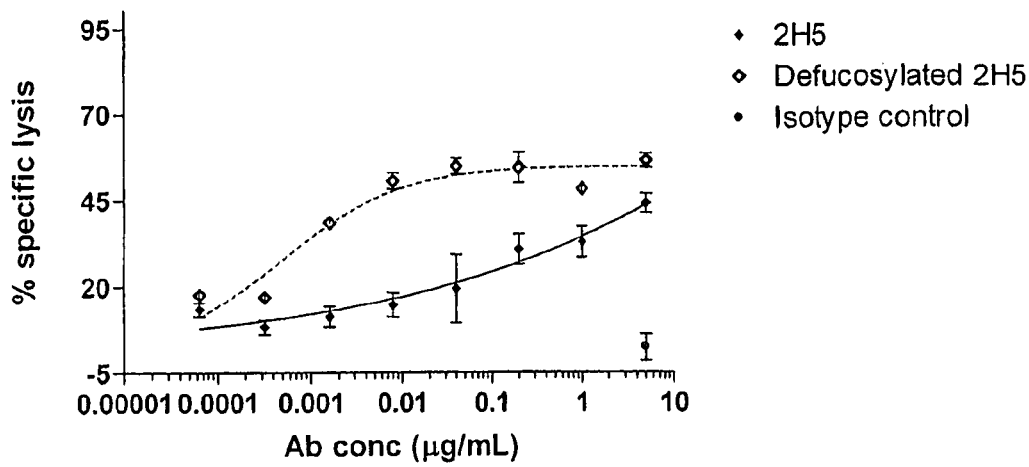
FIGS. 24A-F show the results of an antibody dependent cellular cytotoxicity (ADCC) assay demonstrating that defucosylated human monoclonal anti-CD70 antibodies have increased cell cytotoxicity on human leukemia cells in an ADCC dependent manner. (A) ARH-77 cells; (B) MEC-1 cells; (C) MEC-1 cells treated with anti-CD16 antibody; (D) SU-DHL-6 cells; (E) IM-9 cells; (F) HuT 78 cells.
Figure 24B:
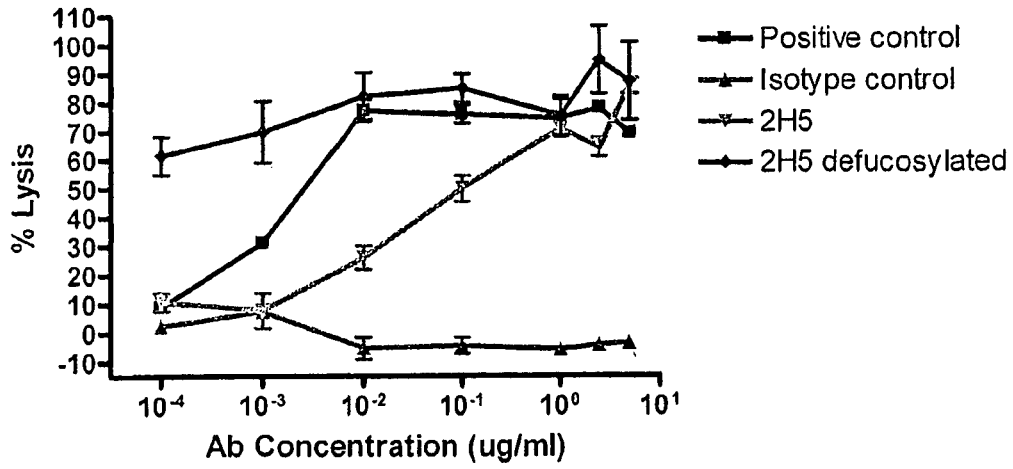
Figure 24C:
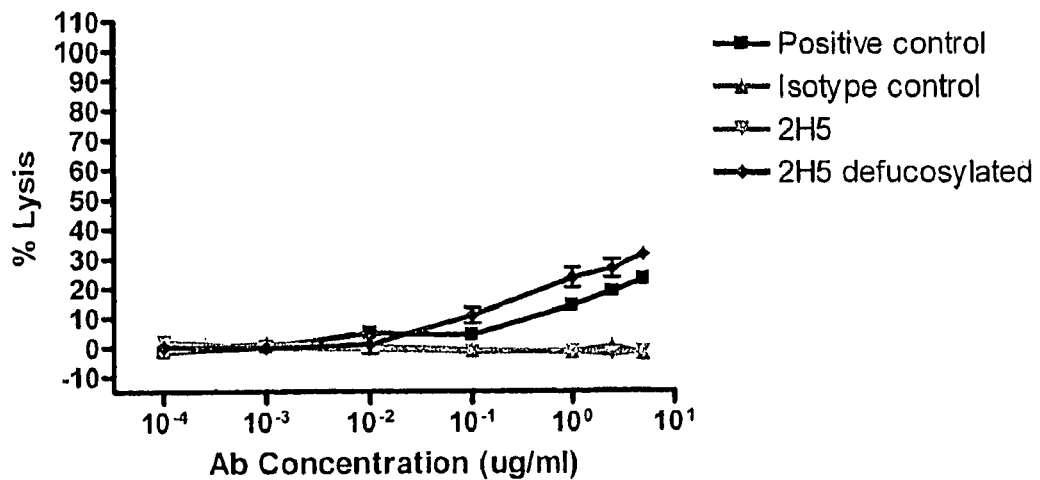
Figure 24D:
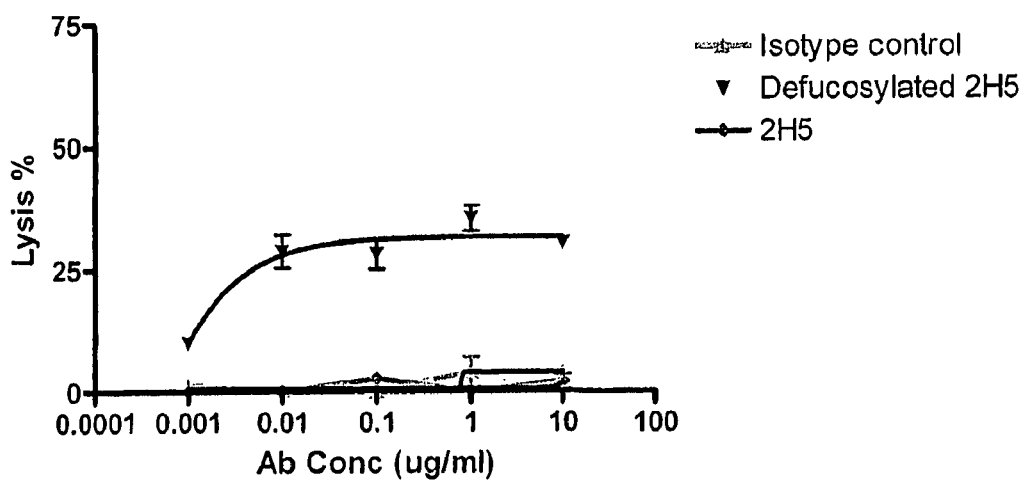
Figure 24E:
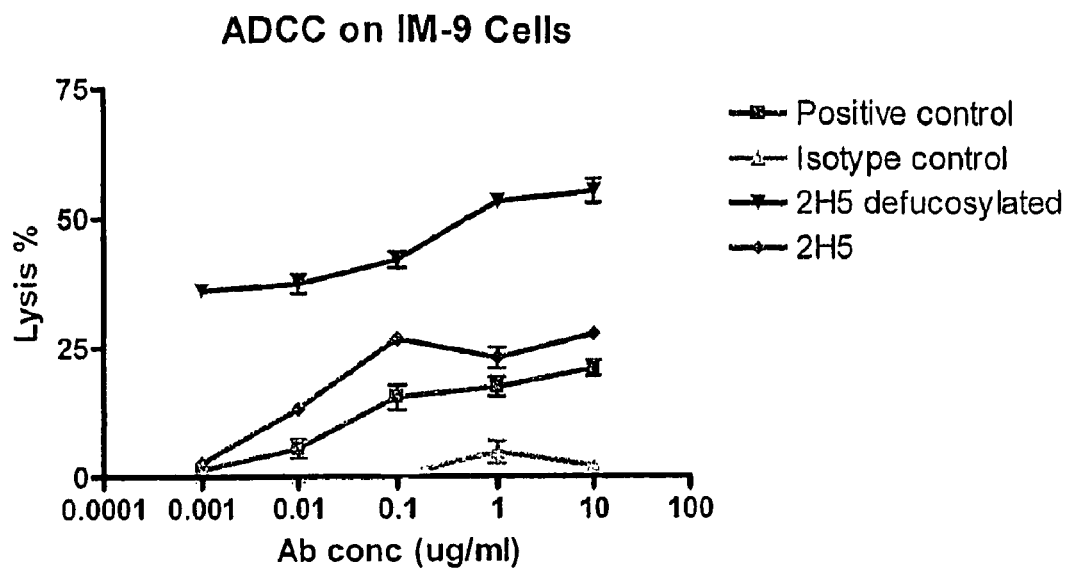
Figure 24F:
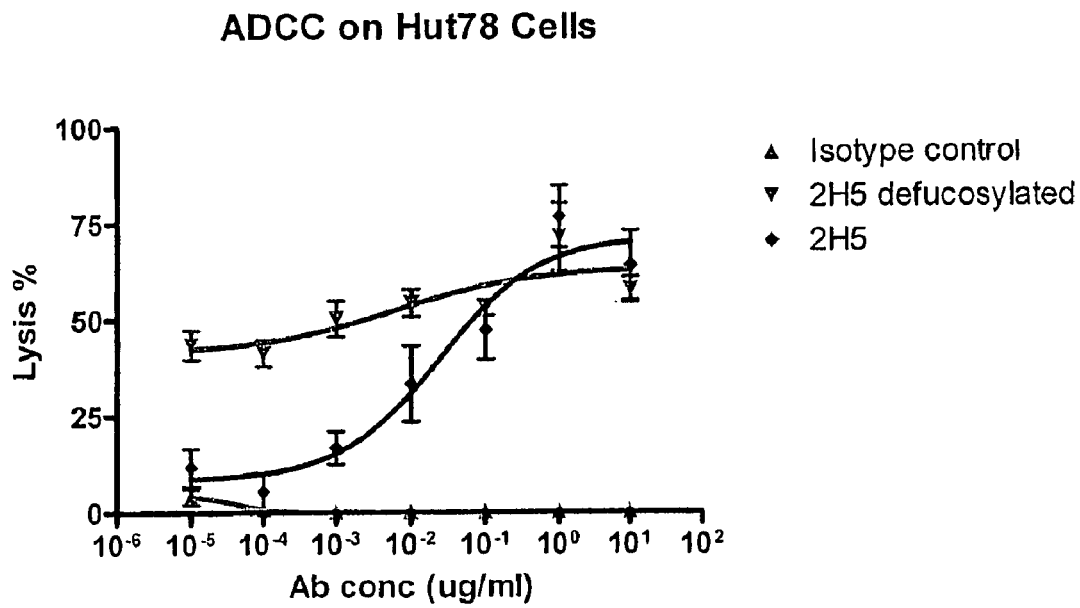

A-498 (ATCC Accession No. HTB-44) and ACHN (ATCC Accession No. CRL-1611) cells were expanded in vitro using standard laboratory procedures. Male Ncr athymic nude mice (Taconic, Hudson, N.Y.) between 6-8 weeks of age were implanted subcutaneously in the right flank with $7.5 \times 10^6$ ACHN or A-498 cells in 0.2 ml of PBS/Matrigel (1:1) per mouse. Mice were weighed and measured for tumors three dimensionally using an electronic caliper twice weekly after implantation. Tumor volumes were calculated as height× width×length. Mice with ACHN tumors averaging 270 mm$^3$ or A498 tumors averaging 110 mm$^3$ were randomized into treatment groups. The mice were dosed intraperitoneally with PBS vehicle, toxin-conjugated isotype control antibody or toxin-conjugated anti-CD70 HuMAb 2H5 on Day 0. Examples of toxin compounds that may be conjugated to the antibodies of the current disclosure are described in the concurrently filed application with reference number MEDX-0034US4. The mice in the A-498 sample group were tested with three different toxin compounds. Mice were monitored for tumor growth for 60 days post dosing. Mice were euthanized when the tumors reached tumor end point (2000 mm$^3$). The results are shown in FIG. 23A (A-498 tumors) and 23B (ACHN tumors). The anti-CD70 antibody 2H5 conjugated to a toxin extended the mean time to reaching the tumor end point volume (2000 mm$^3$) and slowed tumor growth progression. Thus, treatment with an anti-CD70 antibody-toxin conjugate has a direct in vivo inhibitory effect on tumor growth.

Example 12

Immunohistochemistry with 2H5

The ability of the anti-CD70 HuMAb 2H5 to recognize CD70 by immunohistochemistry was examined using clinical biopsies from clear cell renal cell carcinoma (ccRCC), lymphoma and glioblastoma patients.

For immunohistochemistry, 5 µm frozen sections were used (Ardais Inc, USA). After drying for 30 minutes, sections were fixed with acetone (at room temperature for 10 minutes) and air-dried for 5 minutes. Slides were rinsed in PBS and then pre-incubated with 10% normal goat serum in PBS for 20 min and subsequently incubated with 10 µg/ml fitcylated 2H5 in PBS with 10% normal goat serum for 30 min at room temperature. Next, slides were washed three times with PBS and incubated for 30 min with mouse anti-FITC (10 µg/ml DAKO) at room temperature. Slides were washed again with PBS and incubated with Goat anti-mouse HRP conjugate (DAKO) for 30 minutes at room temperature. Slides were washed again 3× with PBS. Diaminobenzidine (Sigma) was used as substrate, resulting in brown staining. After washing with distilled water, slides were counter-stained with hematoxyllin for 1 min. Subsequently, slides were washed for 10 secs in running distilled water and mounted in glycergel (DAKO). Clinical biopsy immunohistochemical staining displayed positive staining in the Non-Hodgkin's Lymphoma, plasmacytoma, ccRcc and glioblastoma sections. Only malignant cells were positive in each case, adjacent normal tissue was not stained.

Example 13

Production of Defucosylated HuMAbs

Antibodies with reduced amounts of fucosyl residues have been demonstrated to increase the ADCC ability of the antibody. In this example, the 2H5 HuMAb has been produced that is lacking in fucosyl residues.

The CHO cell line Ms704-PF, which lacks the fucosyltransferase gene, FUT 8 (Biowa, Inc., Princeton, N.J.) was electroporated with a vector which expresses the heavy and light chains of antibody 2H5. Drug-resistant clones were selected by growth in Ex-Cell 325-PF CHO media (JRH Biosciences, Lenexa, Kans.) with 6 mM L-glutamine and 500 µg/ml G418 (Invitrogen, Carlsbad, Calif.). Clones were screened for IgG expression by standard ELISA assay. Two separate clones were produced, B8A6 and B8C11, which had production rates ranging from 1.0 to 3.8 picograms per cell per day.

Example 14

Assessment of ADCC Activity of Defucosylated Anti-CD70 Antibody

In this example, a defucosylated and non-defucosylated anti-CD70 monoclonal antibody was tested for the ability to kill CD70+ cells in the presence of effector cells via antibody dependent cellular cytotoxicity (ADCC) in a fluorescence cytotoxicity assay.

Human Anti-CD70 monoclonal antibody 2H5 was defucosylated as described above. Human effector cells were prepared from whole blood as follows. Human peripheral blood mononuclear cells were purified from heparinized whole blood by standard Ficoll-paque separation. The cells were resuspended in RPMI1640 media containing 10% FBS (culture media) and 200 U/ml of human IL-2 and incubated overnight at 37° C. The following day, the cells were collected and washed once in culture media and resuspended at $2 \times 10^7$ cells/ml. Target CD70+ cells were incubated with BATDA reagent (Perkin Elmer, Wellesley, Mass.) at 2.5 µl BATDA per $1 \times 10^6$ target cells/mL in culture media supplemented with 2.5 mM probenecid (assay media) for 20 minutes at 37° C. The target cells were washed four times in PBS with 20 mM HEPES and 2.5 mM probenecid, spun down and brought to a final volume of $1 \times 10^5$ cells/ml in assay media.

The CD70+ cell lines ARH-77 (human B lymphoblast leukemia; ATCC Accession No. CRL-1621), MEC-1 (human chronic B cell leukemia; DSMZ Accession No. ACC 497), SU-DHL-6 (human B cell lymphoma, DSMZ Accession No. Acc572), IM-9 (human B lymphoblast; ATCC Accession No. CCL-159) and HuT 78 (human cutaneous lymphocyte lymphoma; ATCC Accession No. TIB-161), were tested for antibody specific ADCC to the defucosylated and non-defucosylated human anti-CD70 monoclonal antibody 2H5 using the Delfia fluorescence emission analysis as follows. The target cell line ARH77 (100 µl of labeled target cells) was incubated with 50 µl of effector cells and 50 µl of either 2H5 or defucosylated 2H5 antibody. A target to effector ratio of 1:50 was used throughout the experiments. A human IgG1 isotype control was used as a negative control. Following a 2100 rpm pulse spin and one hour incubation at 37° C., the supernatants were collected, quick spun again and 20 µl of supernatant was transferred to a flat bottom plate, to which 180 µl of Eu solution (Perkin Elmer, Wellesley, Mass.) was added and read in a Fusion Alpha TRF plate reader (Perkin Elmer). The % lysis was calculated as follows: (sample release−spontaneous release*100)/(maximum release−spontaneous release), where the spontaneous release is the fluorescence from wells which only contain target cells and maximum release is the fluorescence from wells containing target cells and have been treated with 3% Lysol. Cell cytotoxicity % specific lysis for the ARH-77 cell line is shown in FIG. 24. The CD70+ expressing cell lines ARH-77, MEC-1, SU-DHL-6, IM-9 and HuT 78 showed antibody mediated cytotoxicity with the HuMAb anti-CD70 antibody 2H5 and an increased percentage of specific lysis associated with the defucosylated form of the anti-CD70 antibody 2H5. In addition, anti-CD16 antibody was shown to block the ADCC effect in the MEC-1 cell line. This data demonstrates that defucosylated HuMAb anti-CD70 antibodies show increased specific cytotoxicity to CD70+ expressing cells.

Example 15

Assessment of ADCC Activity of Anti-CD70 Antibody Using a $^{51}$Cr-Release Assay In this example, an anti-CD70 monoclonal antibody was tested for the ability to kill CD70+ Raji B lymphocyte cells in the presence of effector cells via antibody dependent cellular cytotoxicity (ADCC) in a $^{51}$Cr-release assay.

Figure 25:
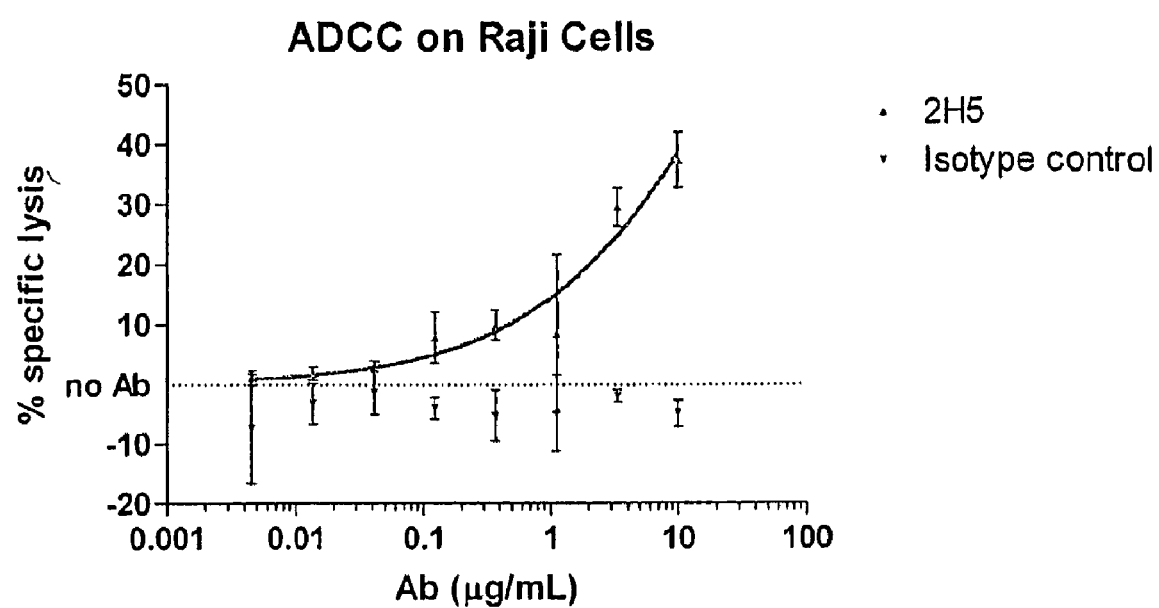
FIG. 25 shows the results of an antibody dependent cellular cytotoxicity (ADCC) assay demonstrating that human monoclonal anti-CD70 antibodies kill human leukemia cells in an ADCC concentration-dependent manner.
Figure 26:
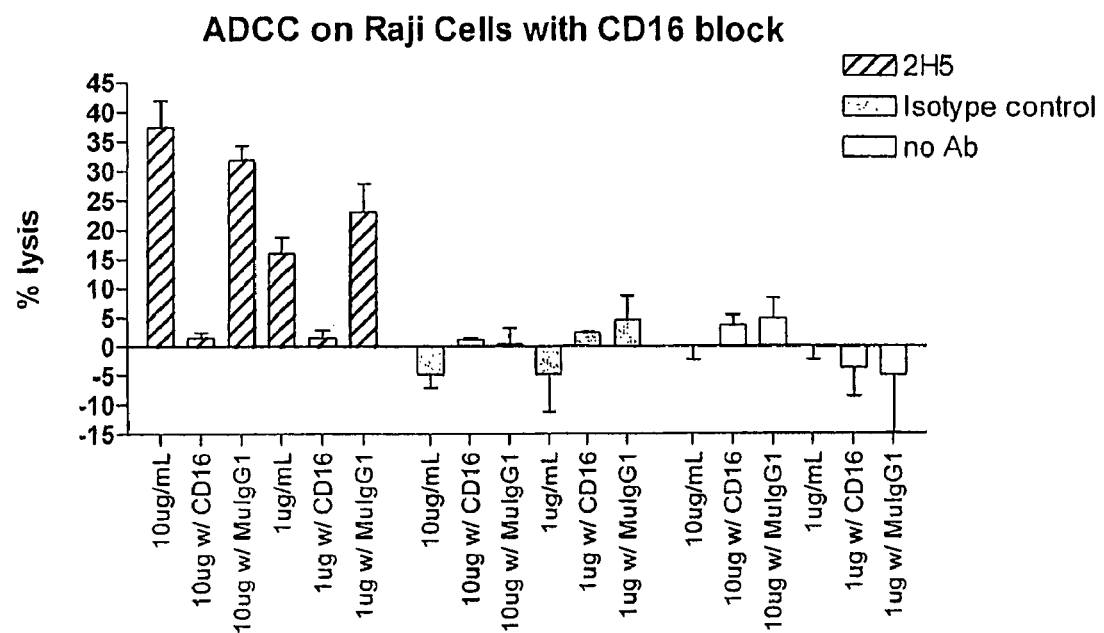
FIG. 26 shows the results of an antibody dependent cellular cytotoxicity (ADCC) assay demonstrating that human monoclonal anti-CD70 antibodies kill human leukemia cells in an ADCC dependent manner, but cytotoxicity is dependent upon CD16.

Human peripheral blood mononuclear cells (effector cells) were purified from heparinized whole blood by standard Ficoll-paque separation. The cells were resuspended at $2 \times 10^6$/mL in RPMI1640 media containing 10% FBS and 200 U/ml of human IL-2 and incubated overnight at 37° C. The following day, the cells were collected and washed once in culture media and resuspended at $2 \times 10^7$ cells/ml. Two million target Raji cells (human B lymphocyte Burkitt's lymphoma; ATCC Accession No. CCL-86) were incubated with 200 µCi $^{51}$Cr in 1 ml total volume for 1 hour at 37° C. The target cells were washed once, resuspended in 1 ml of media, and incubated at 37° C. for an additional 30 minutes. After the final incubation, the target cells were washed once and brought to a final volume of $1 \times 10^5$ cells/ml. For the final ADCC assay, 100 µl of labeled Raji cells were incubated with 50 µl of effector cells and 50 µl of antibody. A target to effector ratio of 1:100 was used throughout the experiments. In all studies, human IgG1 isotype control was used as a negative control. In some studies, the PBMC culture was separated equally into tubes containing either 20 µg/mL of an anti-human CD16 antibody, an irrelevant mouse IgG1 antibody, or no antibody prior to adding PB MC to the assay plate. Following a 15 minute incubation at 27° C., the blood cells were used as described above without washing. Following a 4 hour incubation at 37° C., the supernatants were collected and counted on a Cobra II auto-gamma Counter (Packard Instruments) with a reading window of 240-400 keV. The counts per minute were plotted as a function of antibody concentration and the data was analyzed by non-linear regression, sigmoidal dose response (variable slope) using Prism software (San Diego, Calif.). The percent lysis was determined by the following equation: % Lysis=(Sample CPM−no antibody CPM)/TritonX CPM-No antibody CPM)×100. An antibody titration curve for cell cytotoxicity % specific lysis for the Raji cell line is shown in FIG. 25. This data demonstrates that anti-CD70 antibodies have an ADCC effect on the Raji cell line. The $EC_{50}$ value for the anti-CD70 antibody against Raji cells was 36.61 nM. A graph of cytotoxicity on Raji cells in the presence of an anti-CD16 antibody is shown in FIG. 26. This data demonstrates that the ADCC effect of anti-CD70 antibodies on Raji cells is dependent upon CD16.

Example 16

Assessment of ADCC Activity of Anti-CD70 Antibody on Activated T Cells

In this example, a defucosylated and non-defucosylated anti-CD70 monoclonal antibody was tested for the ability to kill activated T cells in the presence of effector cells via antibody dependent cellular cytotoxicity (ADCC) in a fluorescence cytotoxicity assay.

Human Anti-CD70 monoclonal antibody 2H5 was defucosylated as described above. Human effector cells were prepared as described above. Human spleen T cells were positively selected with anti-CD3 coated magnetic beads (Purity >90%). The cells were stimulated with anti-CD3 and anti-CD28 coated beads and 25 ng/ml IL-2 in Iscove's media+ 10% heat inactivated FCS for 6 days. Cells were collected and assayed for viability by propidium iodide incorporation (60% viable) and live cells were gated and analyzed for CD70 expression (~65% CD70+ on live cells) prior to inclusion in ADCC assays.

Figure 27:
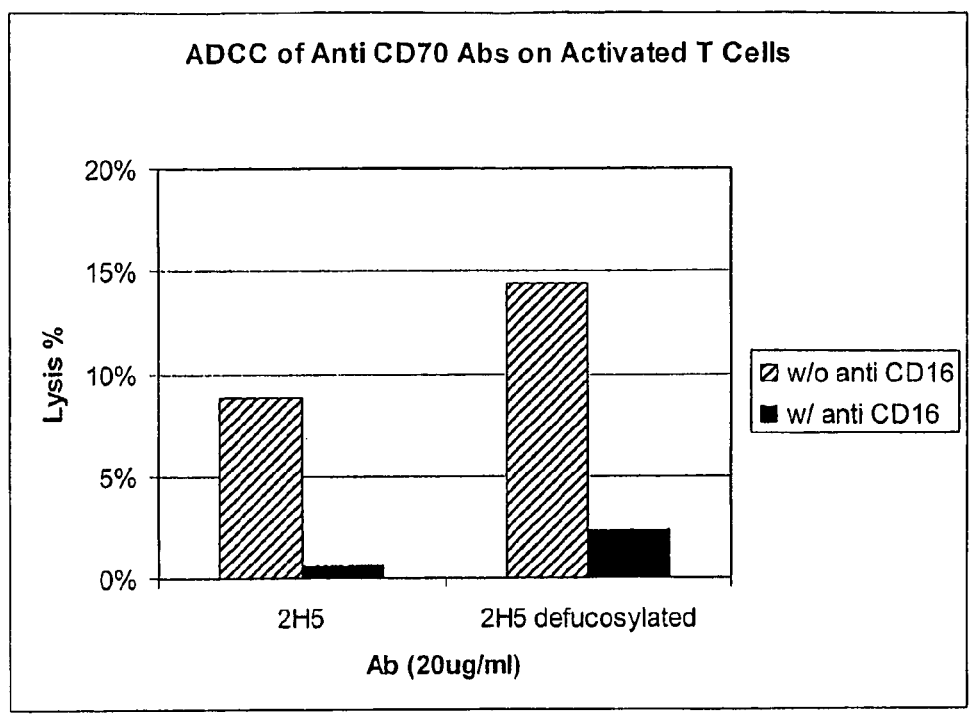
FIG. 27 shows the results of an antibody dependent cellular cytotoxicity (ADCC) assay demonstrating that human monoclonal anti-CD70 antibodies kill human activated T cells and the effect is reversed with the addition of anti-CD16 antibody.

The activated T cells were tested for antibody specific ADCC to the defucosylated and non-defucosylated human anti-CD70 monoclonal antibody 2H5 using the Delfia fluorescence emission analysis as follows. The target activated T cells (100 µl of labeled target cells) was incubated with 50 µl of effector cells and 50 µl of either 2H5 or defucosylated 2H5 antibody. A target to effector ratio of 1:50 was used throughout the experiments. A human IgG1 isotype control was used as a negative control. Following a 2100 rpm pulse spin and one hour incubation at 37° C., the supernatants were collected, quick spun again and 20 µl of supernatant was transferred to a flat bottom plate, to which 180 µl of Eu solution (Perkin Elmer, Wellesley, Mass.) was added and read in a Fusion Alpha TRF plate reader (Perkin Elmer). The % lysis was calculated as follows: (sample release–spontaneous release*100)/(maximum release–spontaneous release), where the spontaneous release is the fluorescence from wells which only contain target cells and maximum release is the fluorescence from wells containing target cells and have been treated with 3% Lysol. Cell cytotoxicity % specific lysis for the activated T cells is shown in FIG. 27. The activated T cells showed antibody mediated cytotoxicity with the HuMAb anti-CD70 antibody 2H5 and an increased percentage of specific lysis associated with the defucosylated form of the anti-CD70 antibody 2H5. The antibody mediated cytotoxicity was blocked by the addition of anti-CD16 antibody in both the defucosylated and non-defucosylated forms of anti-CD70 antibody. The control IgG had no effect on cytotoxicity. This data demonstrates that defucosylated HuMAb anti-CD70 antibodies show increased specific cytotoxicity to activated T cells.

Example 17

Blocking Assay for Receptor-Ligand CD70-CD27 Binding

In this example, anti-CD70 monoclonal antibodies were tested for their ability to block the interaction of CD70 with the ligand CD27 using a blocking assay.

Figure 28:
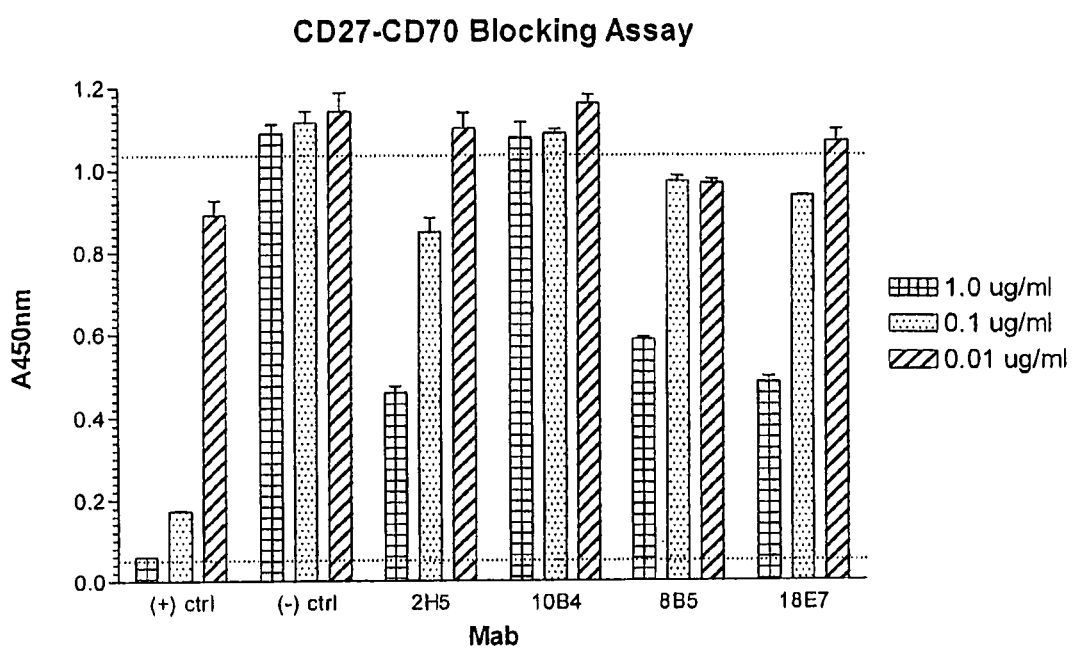
FIG. 28 shows the results of a blocking assay demonstrating that some human monoclonal anti-CD70 antibodies block binding of CD70 to CD27 and other human monoclonal anti-CD70 antibodies do not block binding of CD70 to CD27.

Wells were coated overnight with 100 µl/well of an anti-IgG antibody (Fc-sp.) at 2 µg/ml at 4° C. The wells were blocked with 200 µl/well 1% BSA/PBS for 1 hour at room temperature. To each well was added 100 µl/well of CD27-Fc-his at 0.16 µg/ml for 1 hour at 37° C. while shaking. Each well was washed 5 times with 200 µl/well PBS/Tween 20 (0.05% (v:v)). Anti-CD70 antibody was diluted in 10% NHS+1% BSA/PBS and mixed with CD70-myc-his at 0.05 µg/ml, incubated for 1 hour at room temperature and washed 5 times with 200 µl/well PBS/Tween 20 (0.05% (v:v)). A known antibody that blocks CD70/CD27 interaction was used as a positive control and an isotype control antibody was used as a negative control. The mixture of CD70 and anti-CD70 antibody was blocked with an anti-Fc antibody and 100 µl/well CD70-myc-his+antibody was added to the wells containing CD27-Fc-his. The mixture was incubated for 1 hour shaking at 37° C. To the mixture was added 100 µl/well of anti-myc-HRP (1:1000 diluted in 10% NHS+1% BSA/PBS) and incubated for 1 hour while shaking at 37° C. The signal was detected by adding 100 µl TMB substrate, incubated for 5-10 min at RT, then 75 µl 0.25 M H2SO4 was added and the results were read at A450 nm. The results are shown in FIG. 28. This data demonstrates that some anti-CD70 antibodies, including 2H5, 8B5, and 18E7, block binding of CD70 to CD27, while other antibodies do not affect the interaction between CD70 and CD27.

Example 18

Treatment of In Vivo Tumor Xenograft Model Using Naked Anti-CD70 Antibodies

Mice implanted with a lymphoma tumor were treated in vivo with naked anti-CD70 antibodies to examine the in vivo effect of the antibodies on tumor growth.

Figure 29A:
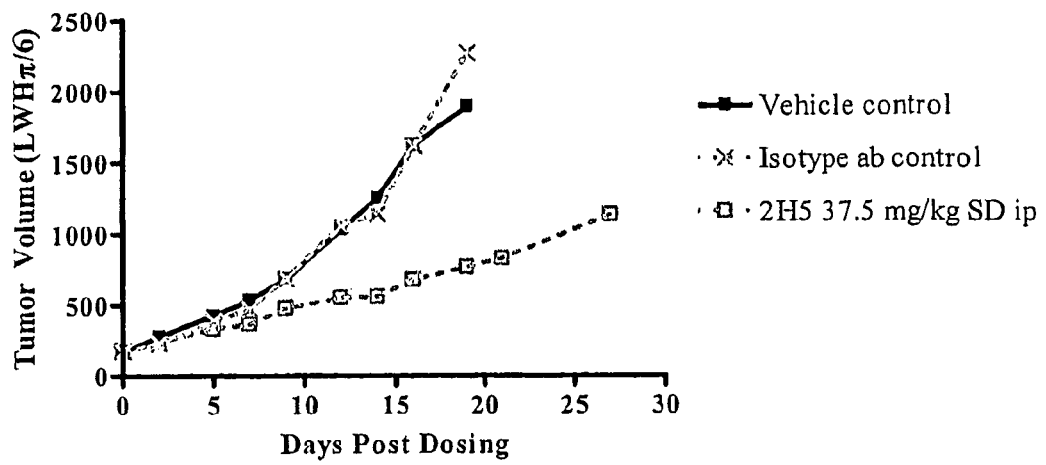
FIGS. 29A-B show the results of an in vivo mouse tumor model study demonstrating that treatment with naked anti-CD70 antibody 2H5 has a direct inhibitory effect on lymphoma tumors in vivo. (A) Raji tumors; (B) ARH-77 tumors.
Figure 29B:
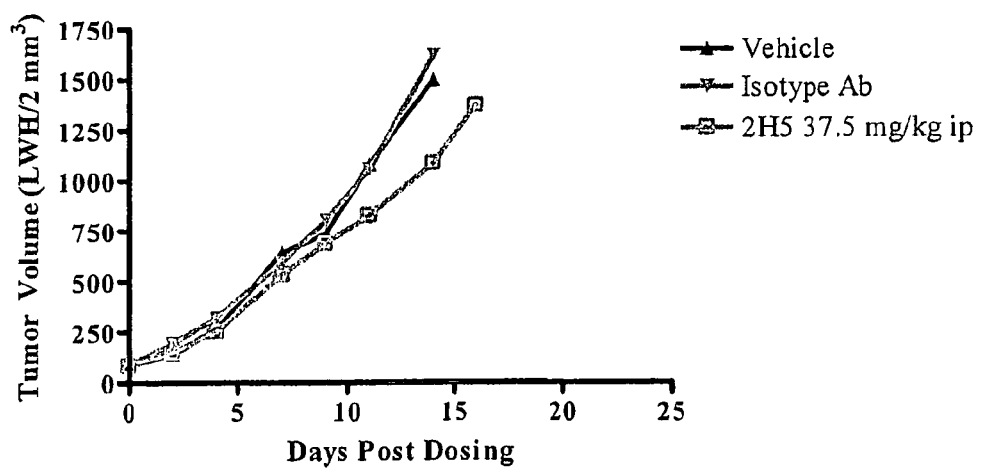

ARH-77 (human B lymphoblast leukemia; ATCC Accession No. CRL-1621) and Raji (human B lymphocyte Burkitt's lymphoma; ATCC Accession No. CCL-86) cells were expanded in vitro using standard laboratory procedures. Male Ncr athymic nude mice (Taconic, Hudson, N.Y.) between 6-8 weeks of age were implanted subcutaneously in the right flank with $5 \times 10^6$ ARH-77 or Raji cells in 0.2 ml of PBS/Matrigel (1:1) per mouse. Mice were weighed and measured for tumors three dimensionally using an electronic caliper twice weekly after implantation. Tumor volumes were calculated as height×width×length/2. Mice with ARH-77 tumors averaging 80 mm$^3$ or Raji tumors averaging 170 mm$^3$ were randomized into treatment groups. The mice were dosed intraperitoneally with PBS vehicle, isotype control antibody or naked anti-CD70 HuMAb 2H5 on Day 0. Mice were euthanized when the tumors reached tumor end point (2000 mm$^3$). The results are shown in FIG. 29A (Raji tumors) and 29B (ARH-77 tumors). The naked anti-CD70 antibody 2H5 extended the mean time to reaching the tumor end point volume (2000 mm$^3$) and slowed tumor growth progression. Thus, treatment with an anti-CD70 antibody alone has a direct in vivo inhibitory effect on tumor growth.

Example 19

Treatment of In Vivo Lymphoma Tumor Xenograft Model Using Cytotoxin-Conjugated Anti-CD70 Antibodies Mice implanted with a lymphoma tumor were treated in vivo with toxin-conjugated anti-CD70 antibodies to examine the in vivo effect of the antibodies on tumor growth.

Figure 30A:
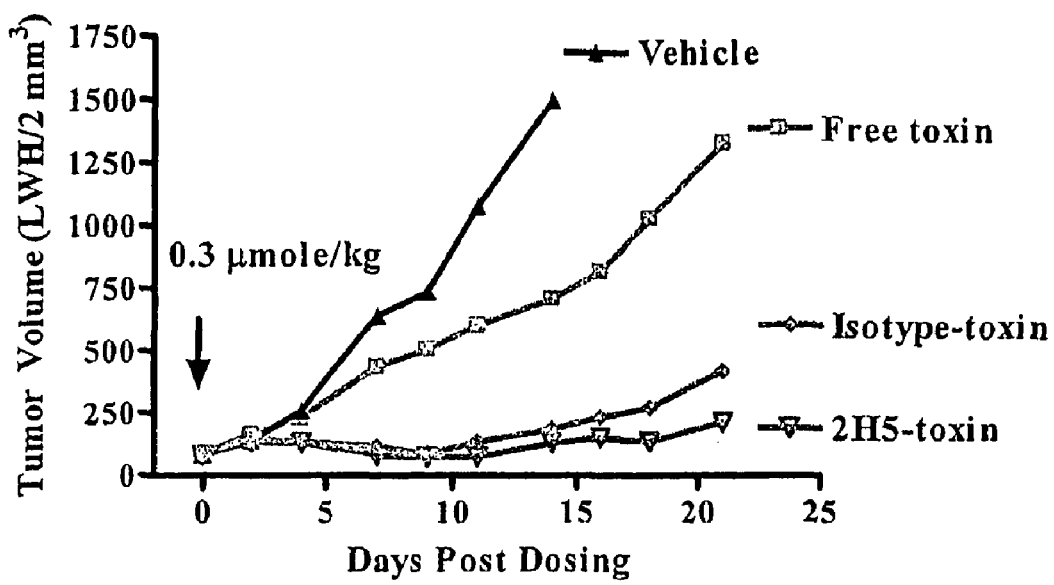
FIGS. 30A-C show the results of an in vivo mouse tumor model study demonstrating that treatment with the toxin conjugated anti-CD70 antibody 2H5 has a direct inhibitory effect on lymphoma tumors in vivo. (A) ARH-77 tumors; (B) Granta 519 tumors; (C) Raji tumors.
Figure 30B:
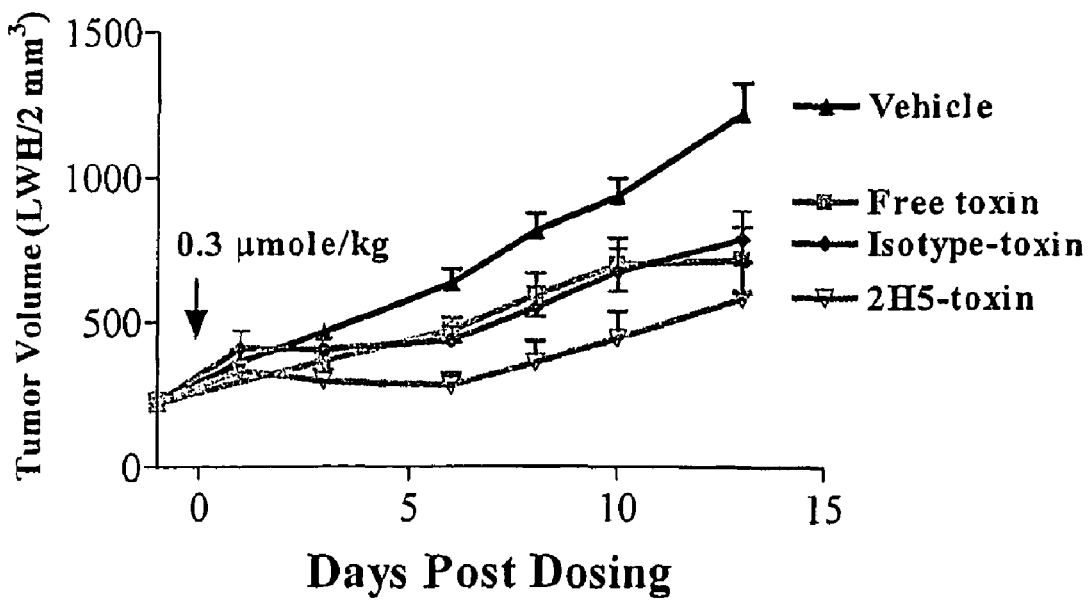
Figure 30C:
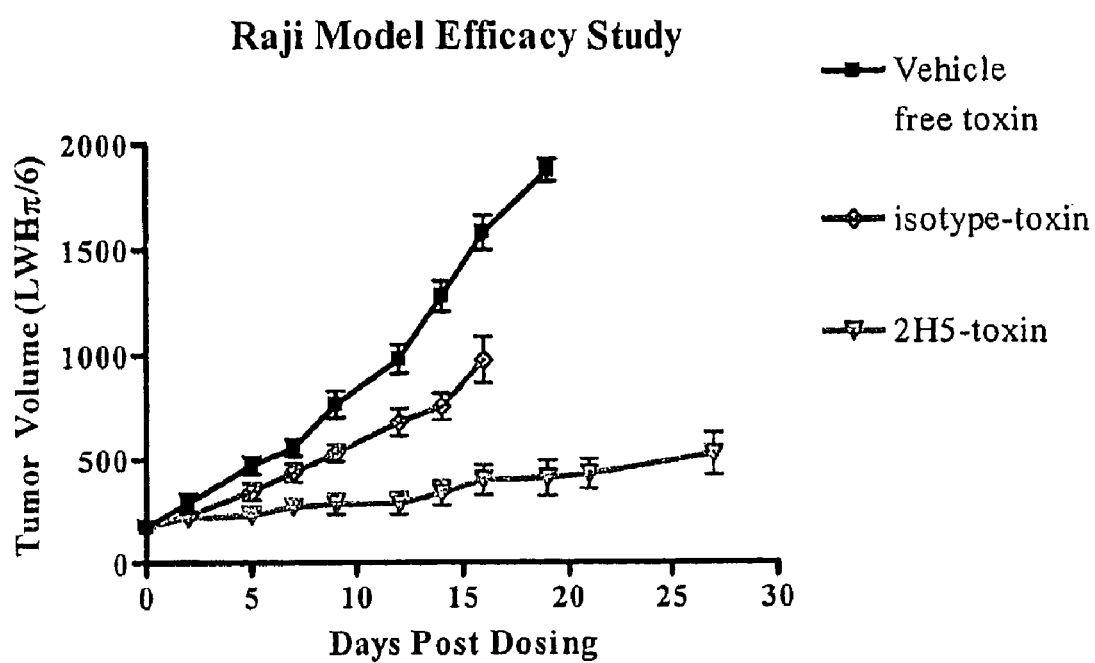

ARH-77 (human B lymphoblast leukemia; ATCC Accession No. CRL-1621), Granta 519 (DSMZ Accession No. 342)

and Raji (human B lymphocyte Burkitt's lymphoma; ATCC Accession No. CCL-86) cells were expanded in vitro using standard laboratory procedures. Male Ncr athymic nude mice (Taconic, Hudson, N.Y.) between 6-8 weeks of age were implanted subcutaneously in the right flank with 5×10$^6$ ARH-77, 10×10$^6$ Granta 519 or 5×10$^6$ Raji cells in 0.2 ml of PBS/Matrigel (1:1) per mouse. Mice were weighed and measured for tumors three dimensionally using an electronic caliper twice weekly after implantation. Tumor volumes were calculated as height×width×length/2. Mice with tumors averaging 80 mm$^3$ (ARH-77), 220 mm$^3$ (Granta 519), or 170 mm$^3$ (Raji), were randomized into treatment groups. The mice were dosed intraperitoneally with PBS vehicle, toxin-conjugated isotype control antibody or toxin-conjugated anti-CD70 HuMAb 2H5 on Day 0. Examples of toxin compounds that may be conjugated to the antibodies of the current disclosure are described in U.S. Provisional Application Ser. No. 60/720,499, filed on Sep. 26, 2005. Mice were euthanized when the tumors reached tumor end point (2000 mm$^3$). The results are shown in FIG. 30A (ARH-77), 30B (Granta 519) and 30C (Raji tumors). The anti-CD70 antibody 2H5 conjugated to a toxin extended the mean time to reaching the tumor end point volume (2000 mm$^3$) and slowed tumor growth progression. Thus, treatment with an anti-CD70 antibody-toxin conjugate has a direct in vivo inhibitory effect on lymphoma tumor growth.

Example 20

Cross-Reactivity of Anti-CD70 Antibody with Rhesus B Lymphoma Cells

Figure 31:
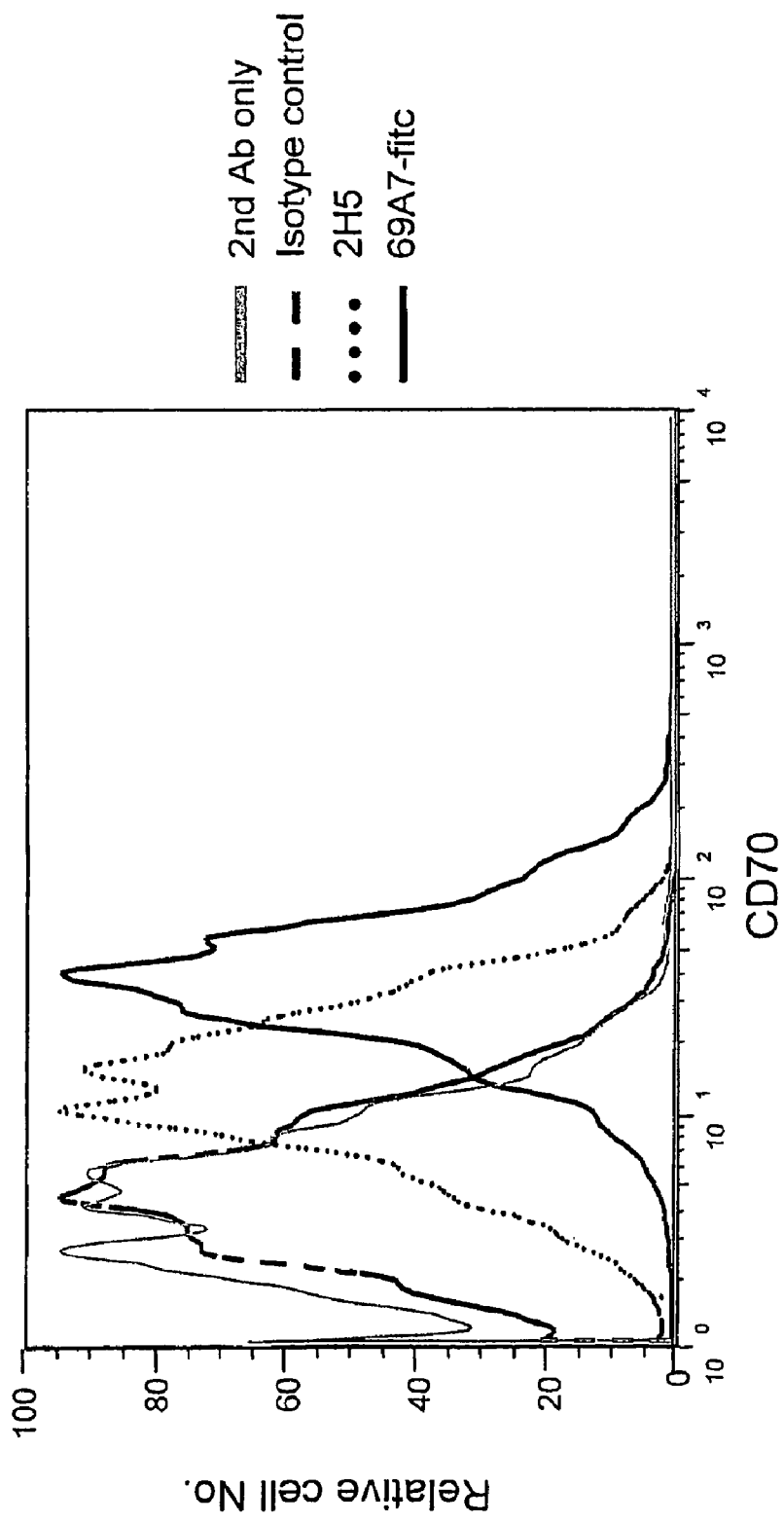
FIG. 31 shows the results of a study showing that the anti-CD70 antibody 69A7 cross-reacts with CD70 expressed on a monkey rhesus CD70+ B lymphoma cell line.

FACS analysis was also employed to access the ability of the anti-CD70 antibody 69A7 cross reacting with the monkey rhesus CD70+ B lymphoma cell line, LCL8664 (ATCC#: CRL-1805). Binding of the HuMAb 69A7 anti-CD70 human monoclonal antibody was assessed by incubating 1×10$^5$ cells with 69A7 at a concentration of 1 μg/ml. The cells were washed and binding was detected with a FITC-labeled anti-human IgG Ab. An isotype control antibody was used as a negative control. Flow cytometric analyses were performed using a FACSCalibur flow cytometry (Becton Dickinson, San Jose, Calif.). The results are shown in FIG. 31. The result demonstrated that the anti-CD70 antibody 69A7 cross-reacts with monkey CD70+ B lymphoma cells.

Example 21

Internalization of Anti-CD70 Antibody Upon Binding to 786-O Renal Carcinoma Cells The 786-O human renal cancer cell line was used to test the internalization of HuMab anti-CD70 antibodies 69A7 and 2H5 upon binding to the cells using immuno-fluorescence staining. 786-O cells (1×10$^4$ cells per 100 μl per well in a 96-well plate) were harvested from a tissue culture flask by treatment with 0.25% Trypsin/EDTA, then incubated with each of the HuMab anti-CD70 antibodies at 5 μg/ml in FACS buffer (PBS+5% FBS, media) for 30 minutes on ice. A human IgG1 isotype control was used as a negative control. Following 2 washes with media, the cells were re-suspended in the media (100 μl per well) and then incubated with goat anti-human secondary antibody conjugated with PE (Jackson ImmunoResearch Lab) at 1:100 dilution on ice for 30 minutes. The cells were either immediately imaged for morphology and immunofluorescence intensity under a fluorescent microscope (Nikon) at 0 min or incubated at 37° C. for various times. Fluorescence was observed in the cells stained with HuMab anti-CD70 antibodies, but not in the control antibody. Similar results were also obtained with FITC-direct conjugated HuMab anti-CD70 antibodies in the assays. The results showed the appearance of the fluorescence on the cell surface membrane with both anti-CD70 HuMabs at 0 min. Following a 30 min incubation, the membrane fluorescence intensity significantly decreased while the internal fluorescence increased. At the 120 min timepoint, membrane fluorescence was not apparent, but instead appeared to be present in intracellular compartments. The data demonstrates that HuMab anti-CD70 antibodies can be specifically internalized upon binding to CD70-expressing endogenous tumor cells.

Example 22

HuMAb Anti-CD70 Blocks the Binding of a Known Mouse anti-CD70 Antibody

Figure 32:
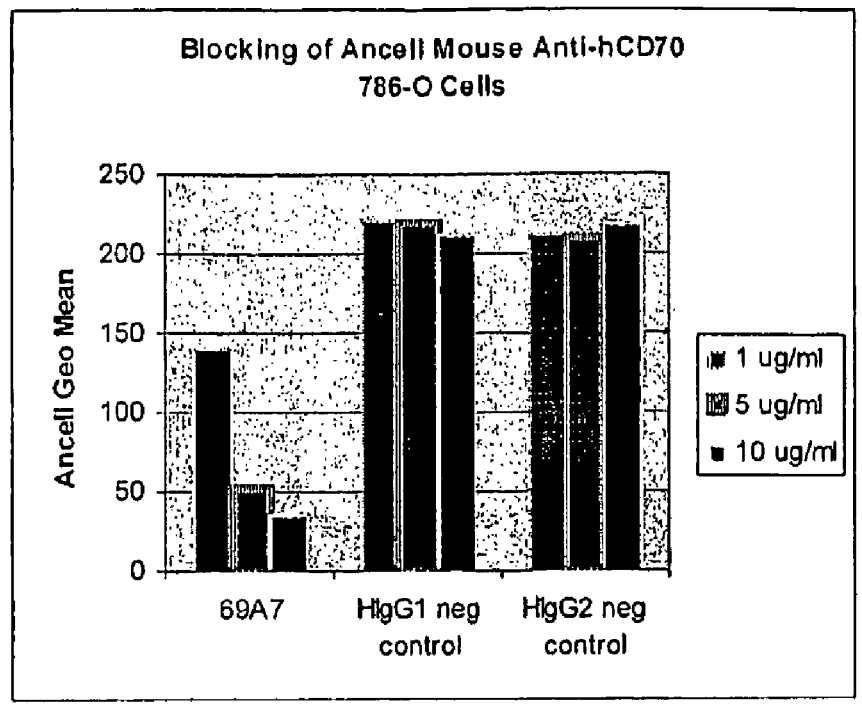
FIG. 32 shows the results of a blocking assay demonstrating that a human anti-CD70 antibody blocks the binding of a known mouse anti-human CD70 antibody.

In this experiment, the HuMAb anti-CD70 antibody 69A7 was tested for its ability to block binding of a known mouse anti-CD70 antibody to CD70+ renal carcinoma 786-O cells. 786-O cells were incubated with the mouse anti-CD70 antibody BU-69 (Ancell, Bayport, Minn.) at 1 μg/ml and the HuMAb 69A7 at 1, 5 or 10 μg/ml for 20 minutes on ice. IgG1 and IgG2 isotype control antibodies were used as negative controls. The cells were washed twice and binding was detected with a FITC-labeled anti-human IgG Ab. Flow cytometric analyses were performed using a FACSCalibur flow cytometry (Becton Dickinson, San Jose, Calif.). The results are shown in FIG. 32. The anti-CD70 HuMAb 69A7 blocks binding of a mouse anti-CD70 antibody in a concentration dependent mariner.

Example 23

HuMAb Anti-CD70 Inhibits Inflammatory Response

Figure 33A:
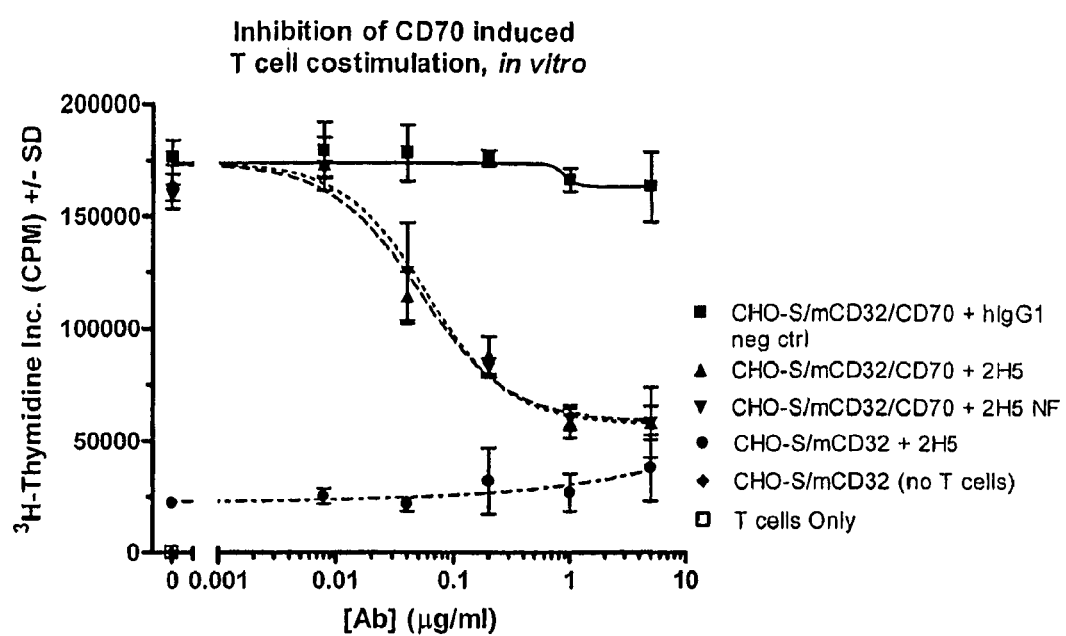
FIGS. 33A and B show the results of treatment with either anti-CD70 antibody or the non-fucosylated form of the antibody. (A) Anti-CD70 antibodies inhibit CD70 co-stimulated cell proliferation in a dose dependent manner. (B) Anti-CD70 antibodies inhibit CD70 co-stimulated IFN-γ secretion in a dose dependent manner.
Figure 33B:
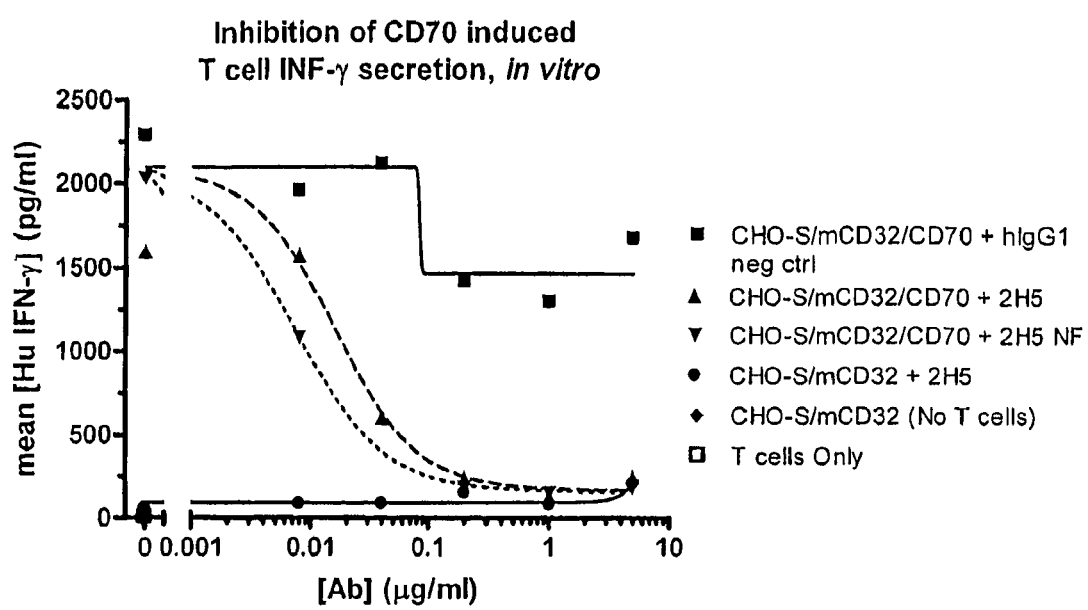

In this experiment, the HuMAb anti-CD70 antibody 2H5 was tested for inhibition of inflammatory responses. CHO—S cells stably transfected with mouse CD32 (CHO—S/mCD32 cells) were transiently transfected with a full length human CD70 construct (CHO—S/mCD32/CD70 cells). Surface expression was confirmed by flow cytometry using 2A5 and PE conjugated anti-human IgG secondary Ab (data not shown). RosetteSep® Human T Cell Enrichment Kit (Cat# 15061; StemCell Technologies Inc) purified human peripheral blood CD3+ T cells were stimulated in vitro at 1×10$^6$/well with 1×10$^5$ CHO—S/mCD32 or CHO—S/mCD32/CD70 cells/well, 1 μg/ml anti-hCD3 (clone OKT3; BD Bioscience) and serial dilutions of either the HuMAb 2H5 or non-fucosylated 2H5 (2H5NF) in triplicate wells of a 96 well plate. After 3 days supernatant aliquots were collected and interferon-gamma (INF-γ) secretion was measured by a quantitative ELISA kit (BD Biosciences). The plates were pulsed with 1 μCi/ml of $^3$H-thymidine, incubated for 8 hours, cells were harvested and $^3$H-thymidine incorporation was read on a Trilux® 1450 Microbeta Counter (Wallac, Inc.). An IgG1 isotype control antibody was used as a negative control. The results are shown in FIG. 33. Both 2H5 and 2H5NF completely inhibited CD70 co-stimulated proliferation in a dose dependent manner (FIG. 33A). Data also show 2H5 inhibition is specific to CD70 costimulation as 2H5 had no effect on anti-CD3+CHO—S/mCD32 mediated proliferation. Both 2H5 and 2H5NF completely inhibited CD70 co-stimulated INF-γ secretion in a dose dependent manner as well (FIG. 33B). Data also show 2H5 inhibition is specific to CD70 costimulation as 2H5 had no effect on anti-CD3+ CHO—S/mCD32 mediated INF-γ secretion. Together data show 2H5 and 2H5NF functionally block CD70 human T cell costimulation.

Figure 34A:
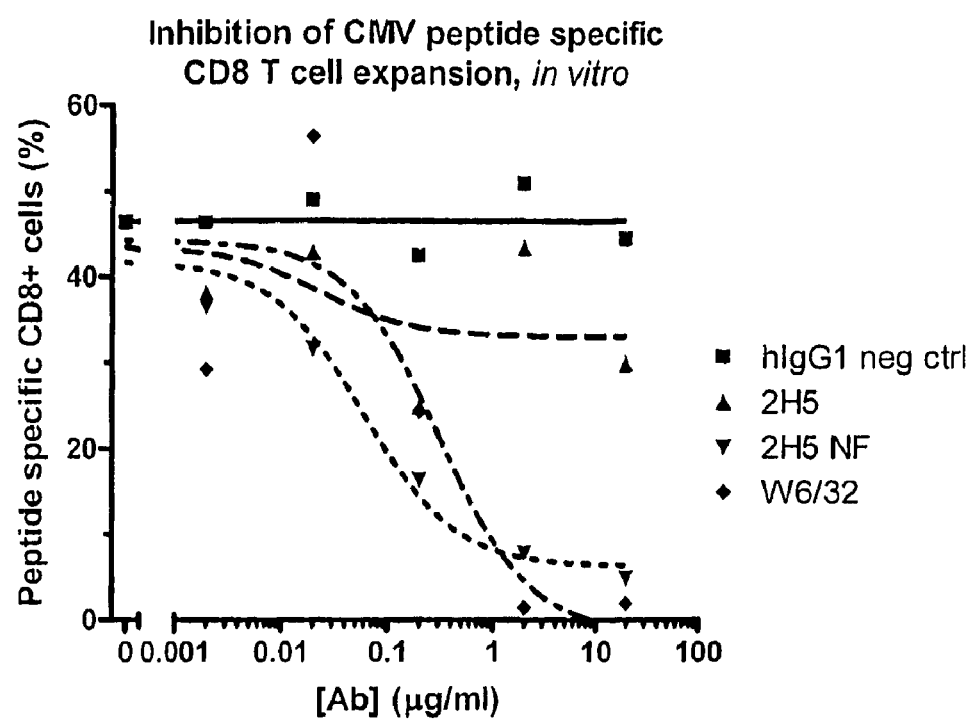
FIGS. 34A-C show the results of treatment with either anti-CD70 antibody or the non-fucosylated form of the antibody on peptide stimulated cells. (A) Anti-CD70 antibodies inhibit peptide specific CD8+ T cell expansion. (B) There was no significant reduction of total cell viability observed. (C) There was no significant reduction of total CD8+ cell numbers observed.
Figure 34B:
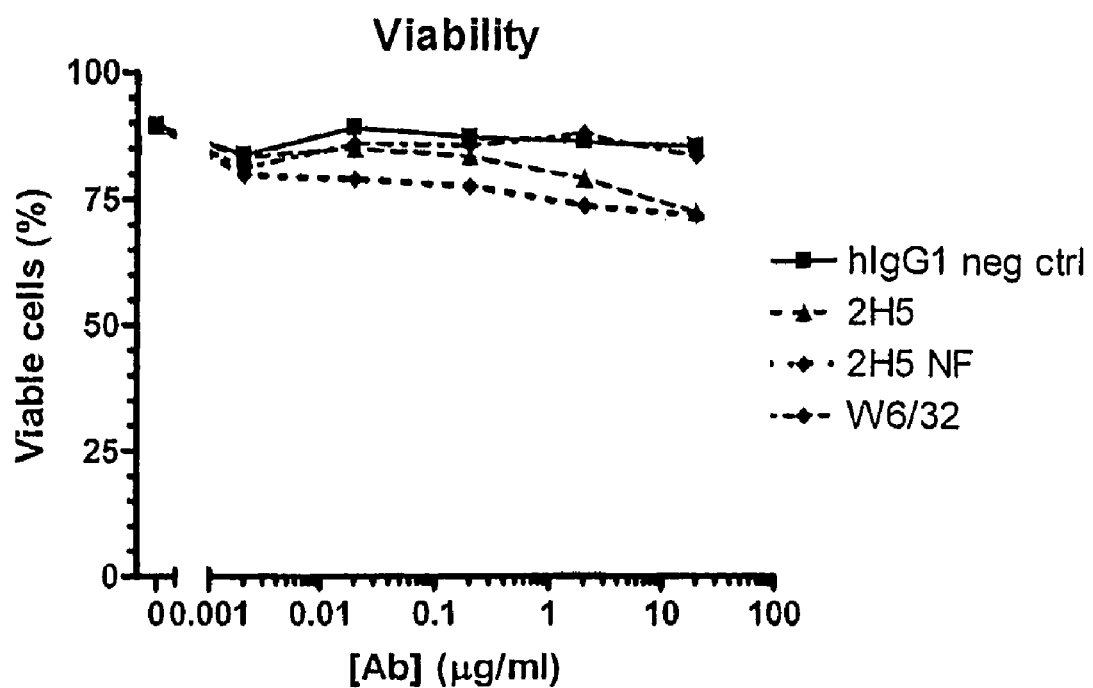
Figure 34C:
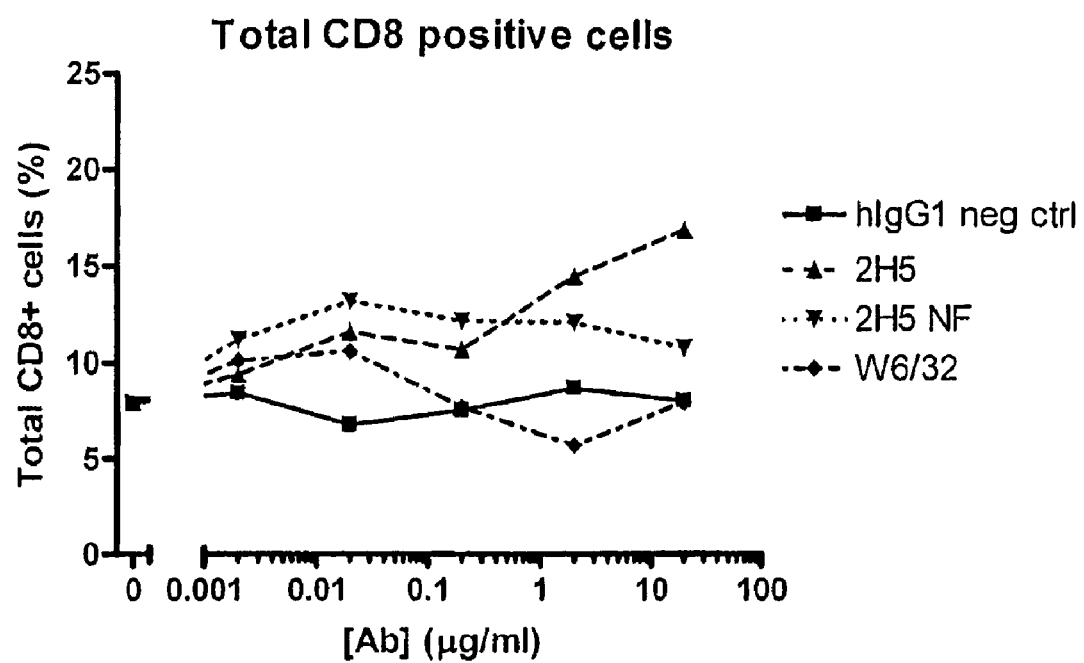

Human MHC class I haplotype B*3501+peripheral blood mononuclear cells (PBMC) pre-screened for cytomegalovirus (CMV) specific T cell responses (Astarte, Inc) were cultured in the presence of 25 ng/ml of B*3501 binding CMV peptide IPSINVHHY (ProImmune, Oxford, UK) and serial dilutions of the HuMAb 2H5 for 11 days. Cultures were analyzed by flow cytometry for CD8+ T cells by PE conjugated anti-CD8 staining (clone RPA-T8, BD Biosciences), for peptide specific CD8+ T cells by APC labeled peptide-MHC Class I pentameric oligomer staining (F114-4B; ProImmune) and for viability by lack of propidium iodide staining. An isotype control antibody was used as a negative control. The results are shown in FIG. 34. 2H5 partially inhibited peptide specific CD8+ T cell expansion and 2H5NF and positive control anti-MHC Class I Ab (clone W6/32; BD Bioscience) completely inhibited peptide specific CD8+ T cell expansion (FIG. 34A). There was no significant reduction of total cell viability observed (FIG. 34B). There was no significant reduction of total CD8+ cell numbers was observed (FIG. 34C). Together, data show 2H5 and 2H5NF effects were specific to peptide stimulated CD8+ T cells. Data is representative of one additional experiment performed with the same donor.

Figure 35:
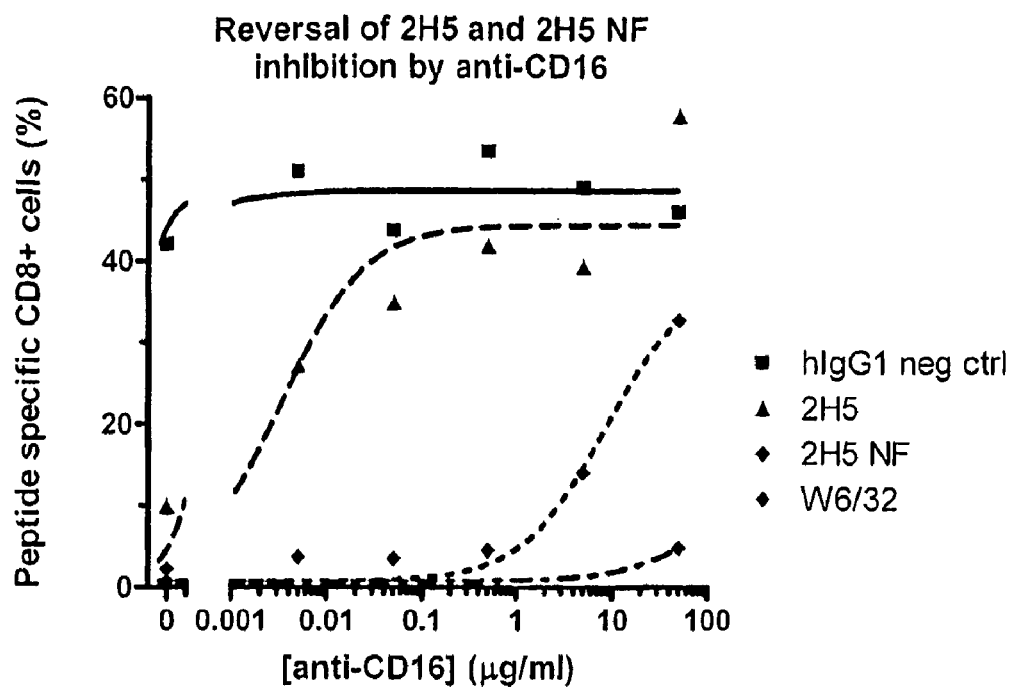
FIG. 35 shows that the effect of anti-CD70 antibodies on peptide specific CD8+ T cell expansion is blocked by addition of anti-CD16 antibodies.

Human MHC class I haplotype B*3501+PBMC prescreened for cytomegalovirus (CMV) specific T cell responses (Astarte, Inc) were cultured in the presence of 25 ng/ml of B*3501 binding CMV peptide IPSINVHHY (ProImmune) and 20 μgs/ml of the HuMAb 2H5 in the presence or absence of serial dilutions of an anti-human CD16 (FcRγII) functional blocking Ab (clone 3G8; BD Biosciences) for 11 days and were then analyzed by flow cytometry for peptide specific CD8+ cell numbers as described above. The results are shown in FIG. 35. Dose dependent reversal of 2H5 and 2H5NF mediated inhibition of peptide specific CD8+ T cell expansion by anti-CD16 shows 2H5 and 2H5NF inhibition is mediated through interaction of 2H5 and 2H5NF with CD16+ effector cells. Approximately 1000-fold more 3G8 was required to reverse 2H5NF mediated inhibition compared to 2H5. There was no inhibition of peptide specific CD8+ T cell expansion by the negative isotype control irrespective of 3G8 concentration and little to no effect of 3G8 on inhibition of peptide specific CD8+ T cell expansion by a functional blocking positive control W6/32.

Example 24

Treatment of In Vivo Renal Carcinoma Tumor Xenograft Model Using Cytotoxin-Conjugated Anti-CD70 Antibodies Mice implanted with a renal carcinoma tumor were treated in vivo with toxin-conjugated anti-CD70 antibodies to examine the in vivo effect of the antibodies on tumor growth.

Figure 36A:
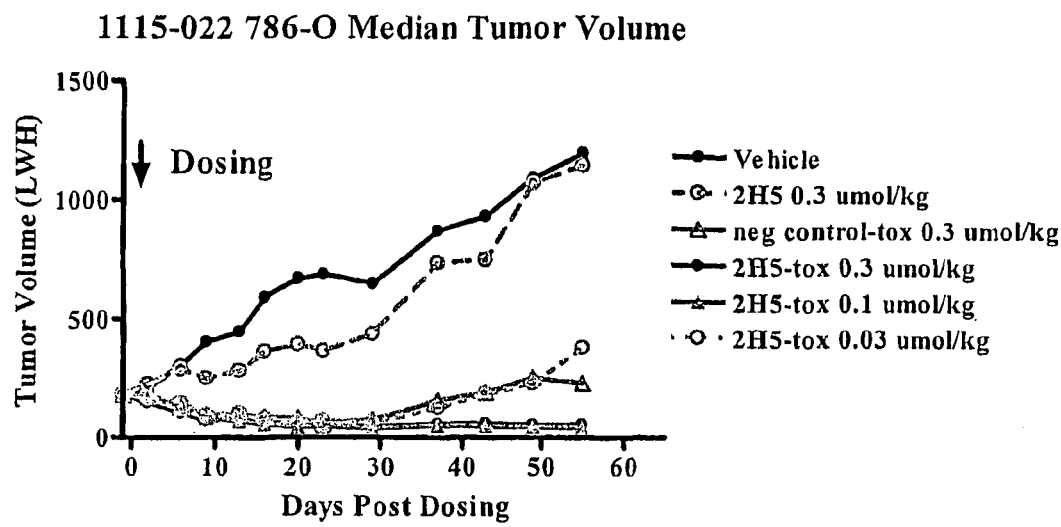
FIGS. 36A-B show the results of an in vivo mouse tumor model study demonstrating that treatment with the toxin conjugated anti-CD70 antibody 2H5 has a direct inhibitory effect on renal carcinoma tumors in vivo. (A) 786-O tumors; (B) Caki-1 tumors.
Figure 36B:
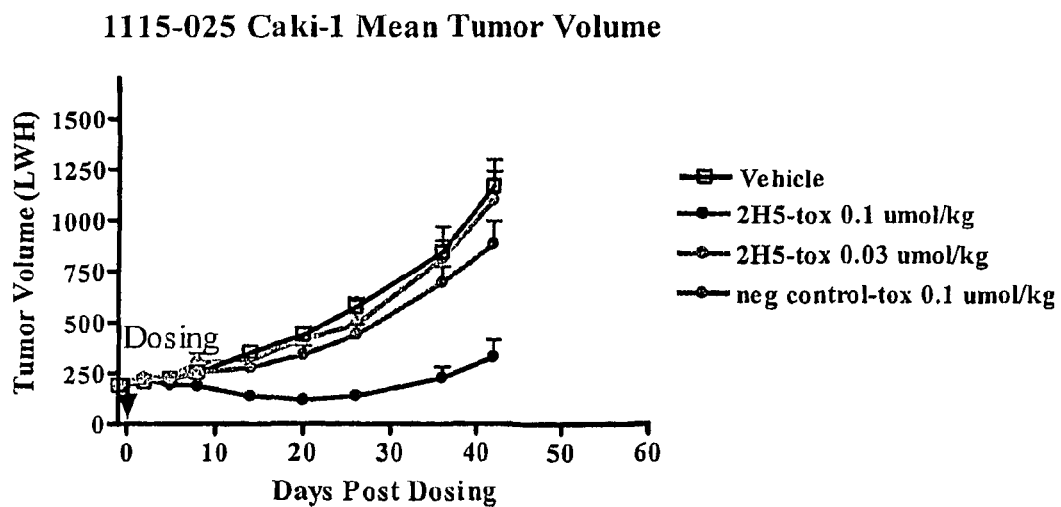

786-O (ATCC Accession No. CRL-1932) and Caki-1 (ATCC Accession No. HTB-46) cells were expanded in vitro using standard laboratory procedures. Male CB17.5CID mice (Taconic, Hudson, N.Y.) between 6-8 weeks of age were implanted subcutaneously in the right flank with 2.5 million 786-O or Caki-1 cells in 0.2 ml of PBS/Matrigel (1:1) per mouse. Mice were weighed and measured for tumors three dimensionally using an electronic caliper twice weekly after implantation. Tumor volumes were calculated as height×width×length. Mice with tumors averaging 200 mm$^3$ were randomized into treatment groups. The mice were dosed intraperitoneally with PBS vehicle, toxin-conjugated isotype control antibody or toxin-conjugated anti-CD70 HuMAb 2H5 on Day 0. Examples of toxin compounds that may be conjugated to the antibodies of the current disclosure are described in U.S. Provisional Application Ser. No. 60/720, 499, filed on Sep. 26, 2005. Mice were euthanized when the tumors reached tumor end point (2000 mm$^3$). The results are shown in FIG. 36A (786-O), and 36B (Caki-1). The anti-CD70 antibody 2H5 conjugated to a toxin extended the mean time to reaching the tumor end point volume (2000 mm$^3$) and slowed tumor growth progression. There was a less than 10% body weight change in the treated animals. Thus, treatment with an anti-CD70 antibody-toxin conjugate has a direct in vivo inhibitory effect on lymphoma tumor growth.

| SEQ ID NO: | SEQUENCE | SEQ ID NO: | SEQUENCE |
|---|---|---|---|
| 1 | VH a.a. 2H5 | 26 | VK CDR1 a.a. 2H5 |
| 2 | VH a.a. 10B4 | 27 | VK CDR1 a.a. 10B4 |
| 3 | VH a.a. 8B5 | 28 | VK CDR1 a.a. 8B5 |
| 4 | VH a.a. 18E7 | 29 | VK CDR1 a.a. 18E7 |
| 5 | VH a.a. 69A7 | 30 | VK CDR1 a.a. 69A7 |
| 6 | VK a.a. 2H5 | 31 | VK CDR2 a.a. 2H5 |
| 7 | VK a.a. 10B4 | 32 | VK CDR2 a.a. 10B4 |
| 8 | VK a.a. 8B5 | 33 | VK CDR2 a.a. 8B5 |
| 9 | VK a.a. 18E7 | 34 | VK CDR2 a.a. 18E7 |
| 10 | VK a.a. 69A7 | 35 | VK CDR2 a.a. 69A7 |
| 11 | VH CDR1 a.a. 2H5 | 36 | VK CDR3 a.a. 2H5 |
| 12 | VH CDR1 a.a. 10B4 | 37 | VK CDR3 a.a. 10B4 |
| 13 | VH CDR1 a.a. 8B5 | 38 | VK CDR3 a.a. 8B5 |
| 14 | VH CDR1 a.a. 18E7 | 39 | VK CDR3 a.a. 18E7 |
| 15 | VH CDR1 a.a. 69A7 | 40 | VK CDR3 a.a. 69A7 |
| 16 | VH CDR2 a.a. 2H5 | 41 | VH n.t. 2H5 |
| 17 | VH CDR2 a.a. 10B4 | 42 | VH n.t. 10B4 |
| 18 | VH CDR2 a.a. 8B5 | 43 | VH n.t. 8B5 |
| 19 | VH CDR2 a.a. 18E7 | 44 | VH n.t. 18E7 |
| 20 | VH CDR2 a.a. 69A7 | 45 | VH n.t. 69A7 |
| 21 | VH CDR3 a.a. 2H5 | 46 | VK n.t. 2H5 |
| 22 | VH CDR3 a.a. 10B4 | 47 | VK n.t. 10B4 |
| 23 | VH CDR3 a.a. 8B5 | 48 | VK n.t. 8B5 |
| 24 | VH CDR3 a.a. 18E7 | 49 | VK n.t. 18E7 |
| 25 | VH CDR3 a.a. 69A7 | 50 | VK n.t. 69A7 |
| 51 | VH 3-30.3 germline a.a. | 54 | VK L6 germline a.a. |
| 52 | VH 3-33 germline a.a. | 55 | VK L18 germline a.a. |
| 53 | VH 4-61 germline a.a. | 56 | VK L15 germline a.a. |

The invention claimed is:

1. An isolated human monoclonal antibody or antigen binding portion thereof, wherein the antibody cross-competes for binding to CD70 with a reference antibody, or antigen binding portion thereof, wherein the reference antibody or reference antigen-binding portion thereof comprises:
   (a) a heavy chain variable region comprising the amino acid sequence of SEQ ID NO:1 and a light chain variable region comprising the amino acid sequence of SEQ ID NO:6;
   (b) a heavy chain variable region comprising the amino acid sequence of SEQ ID NO:2 and a light chain variable region comprising the amino acid sequence of SEQ ID NO:7;
   (c) a heavy chain variable region comprising the amino acid sequence of SEQ ID NO:3 and a light chain variable region comprising the amino acid sequence of SEQ ID NO:8;
   (d) a heavy chain variable region comprising the amino acid sequence of SEQ ID NO:4 and a light chain variable region comprising the amino acid sequence of SEQ ID NO:9; or
   (e) a heavy chain variable region comprising the amino acid sequence of SEQ ID NO:5 and a light chain variable region comprising the amino acid sequence of SEQ ID NO:10.

2. An isolated monoclonal antibody, or antigen binding portion thereof, comprising a heavy chain variable region and a light chain variable region, wherein the heavy chain variable region and light chain variable region are selected from the group consisting of:
   (a) a heavy chain variable region comprising amino acids having the sequence set forth in SEQ ID NO:1; and a light chain variable region comprising amino acids having the sequence set forth in SEQ ID NO:6;
   (b) a heavy chain variable region comprising amino acids having the sequence set forth in SEQ ID NO:2; and a light chain variable region comprising amino acids having the sequence set forth in SEQ ID NO:7;
   (c) a heavy chain variable region comprising amino acids having the sequence set forth in SEQ ID NO:3; and a light chain variable region comprising amino acids having the sequence set forth in SEQ ID NO:8;
   (d) a heavy chain variable region comprising amino acids having the sequence set forth in SEQ ID NO:4; and a light chain variable region comprising amino acids having the sequence set forth in SEQ ID NO:9; and
   (e) a heavy chain variable region comprising amino acids having the sequence set forth in SEQ ID NO:5; and a light chain variable region comprising amino acids having the sequence set forth in SEQ ID NO:10;
wherein the antibody specifically binds to CD70.

3. The antibody, or antigen-binding portion thereof, of claim 2, which comprises:
   (a) a heavy chain variable region comprising amino acids having the sequence set forth in SEQ ID NO:1; and
   (b) a light chain variable region comprising amino acids having the sequence set forth in SEQ ID NO:6.

4. An isolated monoclonal antibody or antigen binding portion thereof, which comprises:
   a) a heavy chain variable region CDR1 comprising SEQ ID NO:11;
   b) a heavy chain variable region CDR2 comprising SEQ ID NO:16;
   c) a heavy chain variable region CDR3 comprising SEQ ID NO:21;
   d) a light chain variable region CDR1 comprising SEQ ID NO:26;
   e) a light chain variable region CDR2 comprising SEQ ID NO:31; and
   f) a light chain variable region CDR3 comprising SEQ ID NO:36.

5. An isolated monoclonal antibody or antigen binding portion thereof, which comprises:
   a) a heavy chain variable region CDR1 comprising SEQ ID NO:12;
   b) a heavy chain variable region CDR2 comprising SEQ ID NO:17;
   a heavy chain variable region CDR3 comprising SEQ ID NO:22;
   c) a light chain variable region CDR1 comprising SEQ ID NO:27;
   d) a light chain variable region CDR2 comprising SEQ ID NO:32; and
   e) a light chain variable region CDR3 comprising SEQ ID NO:37.

6. An isolated monoclonal antibody or antigen binding portion thereof, which comprises:
   a) a heavy chain variable region CDR1 comprising SEQ ID NO:13;
   b) a heavy chain variable region CDR2 comprising SEQ ID NO:18;
   c) a heavy chain variable region CDR3 comprising SEQ ID NO:23;
   d) a light chain variable region CDR1 comprising SEQ ID NO:28;
   e) a light chain variable region CDR2 comprising SEQ ID NO:33; and
   f) a light chain variable region CDR3 comprising SEQ ID NO:38.

7. An isolated monoclonal antibody or antigen binding portion thereof, which comprises:
   a) a heavy chain variable region CDR1 comprising SEQ ID NO:14;
   b) a heavy chain variable region CDR2 comprising SEQ ID NO:19;
   c) a heavy chain variable region CDR3 comprising SEQ ID NO:24;
   d) a light chain variable region CDR1 comprising SEQ ID NO:29;
   e) a light chain variable region CDR2 comprising SEQ ID NO:34; and
   f) a light chain variable region CDR3 comprising SEQ ID NO:39.

8. An isolated monoclonal antibody, or antigen binding portion thereof, which comprises:
   a) a heavy chain variable region CDR1 comprising SEQ ID NO:15;
   b) a heavy chain variable region CDR2 comprising SEQ ID NO:20;
   c) a heavy chain variable region CDR3 comprising SEQ ID NO:25;
   d) a light chain variable region CDR1 comprising SEQ ID NO:30;
   e) a light chain variable region CDR2 comprising SEQ ID NO:35; and
   f) a light chain variable region CDR3 comprising SEQ ID NO:40.

9. The isolated monoclonal antibody, or antigen binding portion thereof, of claim 1, wherein the reference antibody comprises:
   a) a heavy chain variable region comprising the amino acid sequence of SEQ ID NO:5; and b) a light chain variable region comprising the amino acid sequence of SEQ ID NO:10.

10. The isolated monoclonal antibody, or antigen binding portion thereof, of claim 1, wherein the reference antibody comprises:
   a) a heavy chain variable region comprising the amino acid sequence of SEQ ID NO:1; and
   b) a light chain variable region comprising the amino acid sequence of SEQ ID NO:6.

11. The isolated monoclonal antibody, or antigen binding portion thereof, of claim 1, wherein the reference antibody comprises:
   a) a heavy chain variable region comprising the amino acid sequence of SEQ ID NO:2; and
   b) a light chain variable region comprising the amino acid sequence of SEQ ID NO:7.

12. The isolated monoclonal antibody, or antigen binding portion thereof, of claim 1, wherein the reference antibody comprises:
   a) a heavy chain variable region comprising the amino acid sequence of SEQ ID NO:3; and
   b) a light chain variable region comprising the amino acid sequence of SEQ ID NO:8.

13. The isolated monoclonal antibody, or antigen binding portion thereof, of claim 1, wherein the reference antibody comprises:
   a) a heavy chain variable region comprising the amino acid sequence of SEQ ID NO:4; and
   b) a light chain variable region comprising the amino acid sequence of SEQ ID NO:9.

14. A composition comprising the antibody, or antigen-binding portion thereof, according to claim 1, 2, or 3 and a pharmaceutically acceptable carrier.

15. An immunoconjugate comprising the antibody, or antigen-binding portion thereof, according to claim 1, 2, or 3, linked to a therapeutic agent.

16. The immunoconjugate of claim 15, wherein the therapeutic agent is a cytotoxin.

17. The immunoconjugate of claim 15, wherein the therapeutic agent is a radioactive isotope.

18. The antibody, or antigen binding portion thereof, of claim 1, 2 or 3, wherein said antibody is internalized.

19. The antibody, or antigen binding portion thereof, of claim 1, 2 or 3, wherein said antibody binds to a renal cell carcinoma tumor cell line selected from the group consisting of 786-O, A-498, ACHN, Caki-1 and Caki-2 cell lines.

20. The antibody, or antigen binding portion thereof, of claim 1, 2 or 3, wherein said antibody binds to a B-cell tumor cell line.

21. The antibody, or antigen binding portion thereof, of claim 20, wherein the B-cell tumor cell line is selected from the group consisting of Daudi, HuT 78, Raji and Granta 519 cell lines.

22. The antibody, or antigen binding portion thereof, of claim 1, 2 or 3, wherein said antibody lacks fucose residues.

* * * * *

SEQUENCE LISTING

<160> NUMBER OF SEQ ID NOS: 61

<210> SEQ ID NO 1
<211> LENGTH: 118
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser
        115

<210> SEQ ID NO 2
<211> LENGTH: 119
<212> TYPE: PRT
<213> ORGANISM: Homo sapiens

<400> SEQUENCE: 2

Gln Ile Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly Tyr Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Ser Asn Tyr Leu Asp Tyr Trp Gly Gln Gly
            100                 105                 110

Thr Leu Val Thr Val Ser Ser
        115

<210> SEQ ID NO 3
<211> LENGTH: 118
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Lys Thr Leu Ser

```
                65                  70                  75                  80
Leu Gln Met Asn Ser Leu Arg Ala Glu Asp Thr Ala Val Tyr Tyr Cys
                        85                  90                  95

Ala Arg Asp Ser Ile Met Val Arg Gly Asp Tyr Trp Gly Gln Gly Thr
                100                 105                 110

Leu Val Thr Val Ser Ser
            115

<210> SEQ ID NO 4
<211> LENGTH: 118
<212> TYPE: PRT
<213> ORGANISM: Homo sapiens

<400> SEQUENCE: 4

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Asp His
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Ile Met Val Arg Gly Asp Tyr Trp Gly Gln Gly Thr
            100                 105                 110

Leu Val Thr Val Ser Ser
            115

<210> SEQ ID NO 5
<211> LENGTH: 122
<212> TYPE: PRT
<213> ORGANISM: Homo sapiens

<400> SEQUENCE: 5

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Asp
                 20                  25                  30

Tyr Tyr Tyr Trp Ser Trp Ile Arg Gln Pro Pro Gly Lys Gly Leu Glu
             35                  40                  45

Trp Leu Gly Tyr Ile Tyr Tyr Ser Gly Ser Thr Asn Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Arg Ser Val Thr Thr Ala Asp Thr Ala Val Tyr Tyr
                 85                  90                  95

Cys Ala Arg Gly Asp Gly Asp Tyr Gly Gly Asn Cys Phe Asp Tyr Trp
            100                 105                 110

Gly Gln Gly Thr Leu Val Thr Val Ser Ser
            115                 120

<210> SEQ ID NO 6
<211> LENGTH: 107
<212> TYPE: PRT
<213> ORGANISM: Homo sapiens
```

```
<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Leu
                85                  90                  95

Thr Phe Gly Gly Gly Thr Lys Val Glu Ile Lys
            100                 105

<210> SEQ ID NO 7
<211> LENGTH: 107
<212> TYPE: PRT
<213> ORGANISM: Homo sapiens

<400> SEQUENCE: 7

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
```

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Glu Lys Ala Pro Lys Ser Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys
            100                 105

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Phe Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Leu
                85                  90                  95
Thr Phe Gly Gly Gly Thr Lys Val Glu Ile Lys
            100                 105

<210> SEQ ID NO 11
<211> LENGTH: 5
<212> TYPE: PRT
<213> ORGANISM: Homo sapiens

<400> SEQUENCE: 11

Ser Tyr Ile Met His
1               5

<210> SEQ ID NO 12
<211> LENGTH: 5
<212> TYPE: PRT
<213> ORGANISM: Homo sapiens

<400> SEQUENCE: 12

Tyr Tyr Ala Met His

<210> SEQ ID NO 13
<211> LENGTH: 5
<212> TYPE: PRT
<213> ORGANISM: Homo sapiens

<400> SEQUENCE: 13

Asp Tyr Gly Met His
1               5

<210> SEQ ID NO 14
<211> LENGTH: 5
<212> TYPE: PRT
<213> ORGANISM: Homo sapiens

<400> SEQUENCE: 14

Asp His Gly Met His
1               5

<210> SEQ ID NO 15
<211> LENGTH: 7
<212> TYPE: PRT
<213> ORGANISM: Homo sapiens

<400> SEQUENCE: 15

Ser Asp Tyr Tyr Tyr Trp Ser
1               5

<210> SEQ ID NO 16
<211> LENGTH: 17
<212> TYPE: PRT
<213> ORGANISM: Homo sapiens

<400> SEQUENCE: 16

Val Ile Ser Tyr Asp Gly Arg Asn Lys Tyr Tyr Ala Asp Ser Val Lys
1               5                   10                  15

Gly

<210> SEQ ID NO 17
<211> LENGTH: 17
<212> TYPE: PRT
<213> ORGANISM: Homo sapiens

<400> SEQUENCE: 17

Val Ile Ser Tyr Asp Gly Ser Ile Lys Tyr Tyr Ala Asp Ser Val Lys
1               5                   10                  15

Gly

<210> SEQ ID NO 18
<211> LENGTH: 17
<212> TYPE: PRT
<213> ORGANISM: Homo sapiens

<400> SEQUENCE: 18

Val Ile Trp Tyr Asp Gly Ser Asn Lys Tyr Tyr Ala Asp Ser Val Lys
1               5                   10                  15

Gly

<210> SEQ ID NO 19
<211> LENGTH: 17
<212> TYPE: PRT
<213> ORGANISM: Homo sapiens

```
<400> SEQUENCE: 19

Val Ile Trp Tyr Asp Gly Ser Asn Lys Tyr Tyr Ala Asp Ser Val Lys
1               5                   10                  15
Gly

<210> SEQ ID NO 20
<211> LENGTH: 16
<212> TYPE: PRT
<213> ORGANISM: Homo sapiens

<400> SEQUENCE: 20

Tyr Ile Tyr Tyr Ser Gly Ser Thr Asn Tyr Asn Pro Ser Leu Lys Ser
1               5                   10                  15

<210> SEQ ID NO 21
<211> LENGTH: 9
<212> TYPE: PRT
<213> ORGANISM: Homo sapiens

<400> SEQUENCE: 21

Asp Thr Asp Gly Tyr Asp Phe Asp Tyr
1               5

<210> SEQ ID NO 22
<211> LENGTH: 10
<212> TYPE: PRT
<213> ORGANISM: Homo sapiens

<400> SEQUENCE: 22

Glu Gly Pro Tyr Ser Asn Tyr Leu Asp Tyr
1               5                   10

<210> SEQ ID NO 23
<211> LENGTH: 9
<212> TYPE: PRT
<213> ORGANISM: Homo sapiens

<400> SEQUENCE: 23

Asp Ser Ile Met Val Arg Gly Asp Tyr
1               5

<210> SEQ ID NO 24
<211> LENGTH: 9
<212> TYPE: PRT
<213> ORGANISM: Homo sapiens

<400> SEQUENCE: 24

Asp Ser Ile Met Val Arg Gly Asp Tyr
1               5

<210> SEQ ID NO 25
<211> LENGTH: 12
<212> TYPE: PRT
<213> ORGANISM: Homo sapiens

<400> SEQUENCE: 25

Gly Asp Gly Asp Tyr Gly Gly Asn Cys Phe Asp Tyr
1               5                   10

<210> SEQ ID NO 26
<211> LENGTH: 11
<212> TYPE: PRT
<213> ORGANISM: Homo sapiens

<400> SEQUENCE: 26
```

-continued

Arg Ala Ser Gln Ser Val Ser Ser Tyr Leu Ala
 1               5                   10

<210> SEQ ID NO 27
<211> LENGTH: 11
<212> TYPE: PRT
<213> ORGANISM: Homo sapiens

<400> SEQUENCE: 27

Arg Ala Ser Gln Gly Ile Ser Ser Ala Leu Ala
 1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Gly Ile Ser Ser Trp Leu Ala
 1               5                   10

<210> SEQ ID NO 29
<211> LENGTH: 11
<212> TYPE: PRT
<213> ORGANISM: Homo sapiens

<400> SEQUENCE: 29

Arg Ala Ser Gln Gly Ile Ser Ser Trp Leu Ala
 1               5                   10

<210> SEQ ID NO 30
<211> LENGTH: 11
<212> TYPE: PRT
<213> ORGANISM: Homo sapiens

<400> SEQUENCE: 30

Arg Ala Ser Gln Ser Val Ser Ser Tyr Leu Ala
 1               5                   10

<210> SEQ ID NO 31
<211> LENGTH: 8
<212> TYPE: PRT
<213> ORGANISM: Homo sapiens

<400> SEQUENCE: 31

Tyr Asp Ala Ser Asn Arg Ala Thr
 1               5

<210> SEQ ID NO 32
<211> LENGTH: 7
<212> TYPE: PRT
<213> ORGANISM: Homo sapiens

<400> SEQUENCE: 32

Asp Ala Ser Ser Leu Glu Ser
 1               5

<210> SEQ ID NO 33
<211> LENGTH: 7
<212> TYPE: PRT
<213> ORGANISM: Homo sapiens

<400> SEQUENCE: 33

Ala Ala Ser Ser Leu Gln Ser
 1               5

```
<210> SEQ ID NO 34
<211> LENGTH: 7
<212> TYPE: PRT
<213> ORGANISM: Homo sapiens

<400> SEQUENCE: 34

Ala Ala Ser Ser Leu Gln Ser
  1               5

<210> SEQ ID NO 35
<211> LENGTH: 7
<212> TYPE: PRT
<213> ORGANISM: Homo sapiens

<400> SEQUENCE: 35

Asp Ala Ser Asn Arg Ala Thr
  1               5

<210> SEQ ID NO 36
<211> LENGTH: 9
<212> TYPE: PRT
<213> ORGANISM: Homo sapiens

<400> SEQUENCE: 36

Gln Gln Arg Thr Asn Trp Pro Leu Thr
  1               5

<210> SEQ ID NO 37
<211> LENGTH: 9
<212> TYPE: PRT
<213> ORGANISM: Homo sapiens

<400> SEQUENCE: 37

Gln Gln Phe Asn Ser Tyr Pro Phe Thr
  1               5

<210> SEQ ID NO 38
<211> LENGTH: 9
<212> TYPE: PRT
<213> ORGANISM: Homo sapiens

<400> SEQUENCE: 38

Gln Gln Tyr Asn Ser Tyr Pro Leu Thr
  1               5

<210> SEQ ID NO 39
<211> LENGTH: 9
<212> TYPE: PRT
<213> ORGANISM: Homo sapiens

<400> SEQUENCE: 39

Gln Gln Tyr Asn Ser Tyr Pro Leu Thr
  1               5

<210> SEQ ID NO 40
<211> LENGTH: 9
<212> TYPE: PRT
<213> ORGANISM: Homo sapiens

<400> SEQUENCE: 40

Gln Gln Arg Ser Asn Trp Pro Leu Thr
  1               5

<210> SEQ ID NO 41
```

```
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 41 cag gtg cag ctg gtg gag tct ggg gga ggc gtg gtc cag cct ggg agg      48
Gln Val Gln Leu Val Glu Ser Gly Gly Gly Val Val Gln Pro Gly Arg
  1               5                  10                  15 tcc ctg aga ctc tcc tgt gca gcc tct gga ttt acc ttc agt agc tat      96
Ser Leu Arg Leu Ser Cys Ala Ala Ser Gly Phe Thr Phe Ser Ser Tyr
             20                  25                  30 att atg cac tgg gtc cgc cag gct cca ggc aag ggg ctg gag tgg gtg     144
Ile Met His Trp Val Arg Gln Ala Pro Gly Lys Gly Leu Glu Trp Val
         35                  40                  45 gca gtt ata tca tat gat gga aga aac aaa tac tac gca gac tcc gtg     192
Ala Val Ile Ser Tyr Asp Gly Arg Asn Lys Tyr Tyr Ala Asp Ser Val
     50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                 85                  90                  95 gcg aga gat acg gat ggc tac gat ttt gac tac tgg ggc cag gga acc     336
Ala Arg Asp Thr Asp Gly Tyr Asp Phe Asp Tyr Trp Gly Gln Gly Thr
            100                 105                 110 ctg gtc acc gtc tcc tca                                             354
Leu Val Thr Val Ser Ser
        115

<210> SEQ ID NO 42
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 42 caa ata caa ctg gtg gag tct ggg gga ggc gtg gtc cag cct ggg agg      48
Gln Ile Gln Leu Val Glu Ser Gly Gly Gly Val Val Gln Pro Gly Arg
  1               5                  10                  15 tcc ctg aga ctc tcc tgt gca gcc tct gga ttc acc ttc ggt tac tat      96
Ser Leu Arg Leu Ser Cys Ala Ala Ser Gly Phe Thr Phe Gly Tyr Tyr
             20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
         35                  40                  45 gca gtt ata tca tat gat gga agc att aaa tac tac gca gac tcc gtg     192
Ala Val Ile Ser Tyr Asp Gly Ser Ile Lys Tyr Tyr Ala Asp Ser Val
     50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                 85                  90                  95 gcg aga gag ggc cct tac agt aac tac ctt gac tac tgg ggc cag gga     336
Ala Arg Glu Gly Pro Tyr Ser Asn Tyr Leu Asp Tyr Trp Gly Gln Gly
            100                 105                 110
```

```
acc ctg gtc acc gtc tcc tca                                              357
Thr Leu Val Thr Val Ser Ser
            115

<210> SEQ ID NO 43
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 43 cag gtg cag ctg gtg gag tct ggg gga ggc gtg gtc cag cct ggg agg        48
Gln Val Gln Leu Val Glu Ser Gly Gly Gly Val Val Gln Pro Gly Arg
 1               5                  10                  15 tcc ctg aga ctc tcc tgt gcg acg tct gga ttc acc ttc agt gac tat        96
Ser Leu Arg Leu Ser Cys Ala Thr Ser Gly Phe Thr Phe Ser Asp Tyr
            20                  25                  30 ggc atg cac tgg gtc cgc cag gct cca ggc aag ggg ctg gag tgg gtg       144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg       192
Ala Val Ile Trp Tyr Asp Gly Ser Asn Lys Tyr Tyr Ala Asp Ser Val
    50                  55                  60 aag ggc cga ttc acc atc tcc aga gac aat tcc aag aaa acg ctg tct       240
Lys Gly Arg Phe Thr Ile Ser Arg Asp Asn Ser Lys Lys Thr Leu Ser
 65                  70                  75                  80 ctg caa atg aac agc ctg aga gcc gag gac acg gct gtg tat tac tgt       288
Leu Gln Met Asn Ser Leu Arg Ala Glu Asp Thr Ala Val Tyr Tyr Cys
                85                  90                  95 gcg aga gat tct att atg gtt cgg ggg gac tac tgg ggc cag gga acc       336
Ala Arg Asp Ser Ile Met Val Arg Gly Asp Tyr Trp Gly Gln Gly Thr
            100                 105                 110 ctg gtc acc gtc tcc tca                                                354
Leu Val Thr Val Ser Ser
            115

<210> SEQ ID NO 44
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 44 cag gtg cag ctg gtg gag tct ggg gga ggc gtg gtc cag cct ggg agg        48
Gln Val Gln Leu Val Glu Ser Gly Gly Gly Val Val Gln Pro Gly Arg
 1               5                  10                  15 tcc ctg aga ctc tcc tgt gca gcg tct gga ttc acc ttc agc gac cat        96
Ser Leu Arg Leu Ser Cys Ala Ala Ser Gly Phe Thr Phe Ser Asp His
            20                  25                  30 ggc atg cac tgg gtc cgc cag gct cca ggc aag ggg ctg gag tgg gtg       144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg       192
Ala Val Ile Trp Tyr Asp Gly Ser Asn Lys Tyr Tyr Ala Asp Ser Val
    50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt       288
Leu Gln Met Asn Ser Leu Arg Ala Glu Asp Thr Ala Val Tyr Tyr Cys
```

```
                             85                  90                  95
gcg aga gat tct att atg gtt cgg ggg gac tac tgg ggc cag gga acc        336
Ala Arg Asp Ser Ile Met Val Arg Gly Asp Tyr Trp Gly Gln Gly Thr
            100                 105                 110 ctg gtc acc gtc tcc tca                                                354
Leu Val Thr Val Ser Ser
        115

<210> SEQ ID NO 45
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 45 cag gtg cag ctg cag gag tcg ggc cca gga ctg gtg aag cct tcg gag         48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc gtc agc agt gat         96
Thr Leu Ser Leu Thr Cys Thr Val Ser Gly Gly Ser Val Ser Ser Asp
            20                  25                  30 tat tac tac tgg agc tgg atc cgg cag ccc cca ggg aag gga ctg gag        144
Tyr Tyr Tyr Trp Ser Trp Ile Arg Gln Pro Pro Gly Lys Gly Leu Glu
        35                  40                  45 tgg ctt ggg tat atc tat tac agt ggg agc acc aac tac aac ccc tcc        192
Trp Leu Gly Tyr Ile Tyr Tyr Ser Gly Ser Thr Asn Tyr Asn Pro Ser
    50                  55                  60 ctc aag agt cga gtc acc ata tca gta gac acg tcc aag aac cag ttc        240
Leu Lys Ser Arg Val Thr Ile Ser Val Asp Thr Ser Lys Asn Gln Phe
65                  70                  75                  80 tcc ctg aag ctg agg tct gtg acc act gcg gac acg gcc gtg tat tac        288
Ser Leu Lys Leu Arg Ser Val Thr Thr Ala Asp Thr Ala Val Tyr Tyr
                85                  90                  95 tgt gcg aga ggg gat ggg gac tac ggt ggt aac tgt ttt gac tac tgg        336
Cys Ala Arg Gly Asp Gly Asp Tyr Gly Gly Asn Cys Phe Asp Tyr Trp
            100                 105                 110 ggc cag gga acc ctg gtc acc gtc tcc tca                                366
Gly Gln Gly Thr Leu Val Thr Val Ser Ser
        115                 120

<210> SEQ ID NO 46
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 46 gaa att gtg ttg aca cag tct cca gcc acc ctg tct ttg tct cca ggg         48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac         96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc        144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc        192
Tyr Asp Ala Ser Asn Arg Ala Thr Gly Ile Pro Ala Arg Phe Ser Gly
    50                  55                  60
```

```
agt ggg tct ggg aca gac ttc act ctc acc atc agc agc cta gag cct      240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt acc aac tgg ccg ctc      288
Glu Asp Phe Ala Val Tyr Tyr Cys Gln Gln Arg Thr Asn Trp Pro Leu
                 85                  90                  95 act ttc ggc gga ggg acc aag gtg gag atc aaa                          321
Thr Phe Gly Gly Gly Thr Lys Val Glu Ile Lys
            100                 105

<210> SEQ ID NO 47
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 47 gcc atc cag ttg acc cag tct cca tcc tcc ctg tct gca tct gta gga       48
Ala Ile Gln Leu Thr Gln Ser Pro Ser Ser Leu Ser Ala Ser Val Gly
  1               5                  10                  15 gac aga gtc acc atc act tgc cgg gca agt cag ggc att agc agt gct       96
Asp Arg Val Thr Ile Thr Cys Arg Ala Ser Gln Gly Ile Ser Ser Ala
                 20                  25                  30 tta gcc tgg tat cag cag aaa cca ggg aaa gct cct aag ttc ttg atc      144
Leu Ala Trp Tyr Gln Gln Lys Pro Gly Lys Ala Pro Lys Phe Leu Ile
         35                  40                  45 tat gat gcc tcc agt ttg gaa agt ggg gtc cca tca agg ttc agc ggc      192
Tyr Asp Ala Ser Ser Leu Glu Ser Gly Val Pro Ser Arg Phe Ser Gly
 50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac cca ttc      288
Glu Asp Phe Ala Thr Tyr Tyr Cys Gln Gln Phe Asn Ser Tyr Pro Phe
                 85                  90                  95 act ttc ggc cct ggg acc aaa gtg gat atc aaa                          321
Thr Phe Gly Pro Gly Thr Lys Val Asp Ile Lys
            100                 105

<210> SEQ ID NO 48
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 48 gac atc cag atg acc cag tct cca tcc tca ctg tct gca tct gta gga       48
Asp Ile Gln Met Thr Gln Ser Pro Ser Ser Leu Ser Ala Ser Val Gly
  1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
                 20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
 50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
```

```
                      65                  70                  75                  80
gaa gat ttt gca act tat tac tgc caa cag tat aat agt tac ccg ctc       288
Glu Asp Phe Ala Thr Tyr Tyr Cys Gln Gln Tyr Asn Ser Tyr Pro Leu
                     85                  90                  95 act ttc ggc gga ggg acc aag gtg gag atc aaa                           321
Thr Phe Gly Gly Gly Thr Lys Val Glu Ile Lys
            100                 105

<210> SEQ ID NO 49
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 49 gac atc cag atg acc cag tct cca tcc tca ctg tct gca tct gta gga       48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
            20                  25                  30 tta gcc tgg tat cag cag aaa cca gag aaa gcc cct aag tcc ctg atc       144
Leu Ala Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc       192
Tyr Ala Ala Ser Ser Leu Gln Ser Gly Val Pro Ser Arg Phe Ser Gly
    50                  55                  60 agt gga tct ggg aca gat ttc act ctc acc atc agc agc ctg cag cct       240
Ser Gly Ser Gly Thr Asp Phe Thr Leu Thr Ile Ser Ser Leu Gln Pro
65                  70                  75                  80 gaa gat ttt gca act tat tac tgc caa cag tat aat agt tac ccg ctc       288
Glu Asp Phe Ala Thr Tyr Tyr Cys Gln Gln Tyr Asn Ser Tyr Pro Leu
                85                  90                  95 act ttc ggc gga ggg acc aag gtg gag atc aaa                           321
Thr Phe Gly Gly Gly Thr Lys Val Glu Ile Lys
            100                 105

<210> SEQ ID NO 50
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 50 gaa att gtg ttg aca cag tct cca gcc acc ctg tct ttg tct cca ggg       48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac       96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
        35                  40                  45 ttt gat gca tcc aac agg gcc act ggc atc cca gcc agg ttc agt ggc       192
Phe Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
65                  70                  75                  80
```

```
gaa gat ttt gca gtt tat tac tgt cag caa cgt agc aac tgg ccg ctc          288
Glu Asp Phe Ala Val Tyr Tyr Cys Gln Gln Arg Ser Asn Trp Pro Leu
                85                  90                  95 act ttc ggc gga ggg acc aag gtg gag atc aaa                              321
Thr Phe Gly Gly Gly Thr Lys Val Glu Ile Lys
            100                 105
```

<210> SEQ ID NO 51
<211> LENGTH: 98
<212> TYPE: PRT
<213> ORGANISM: Homo sapiens

<400> SEQUENCE: 51

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 52
<211> LENGTH: 98
<212> TYPE: PRT
<213> ORGANISM: Homo sapiens

<400> SEQUENCE: 52

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 53
<211> LENGTH: 99
<212> TYPE: PRT
<213> ORGANISM: Homo sapiens

<400> SEQUENCE: 53

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

```
Trp Ile Gly Tyr Ile Tyr Tyr Ser Gly Ser Thr Asn Tyr Asn Pro Ser
            50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 54
<211> LENGTH: 95
<212> TYPE: PRT
<213> ORGANISM: Homo sapiens

<400> SEQUENCE: 54

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                85                  90                  95

<210> SEQ ID NO 55
<211> LENGTH: 95
<212> TYPE: PRT
<213> ORGANISM: Homo sapiens

<400> SEQUENCE: 55

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                85                  90                  95

<210> SEQ ID NO 56
<211> LENGTH: 95
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                85                  90                  95

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Pro Ser Ile Asn Val His His Tyr
 1               5

<210> SEQ ID NO 58
<211> LENGTH: 15
<212> TYPE: PRT
<213> ORGANISM: Homo sapiens

<400> SEQUENCE: 58

Tyr Phe Asp Tyr Trp Gly Gln Gly Thr Leu Val Thr Val Ser Ser
 1               5                  10                  15

<210> SEQ ID NO 59
<211> LENGTH: 4
<212> TYPE: PRT
<213> ORGANISM: Homo sapiens

<400> SEQUENCE: 59

Met Val Arg Gly
 1

<210> SEQ ID NO 60
<211> LENGTH: 12
<212> TYPE: PRT
<213> ORGANISM: Homo sapiens

<400> SEQUENCE: 60

Leu Thr Phe Gly Gly Gly Thr Lys Val Glu Ile Lys
 1               5                  10

<210> SEQ ID NO 61
<211> LENGTH: 12
<212> TYPE: PRT
<213> ORGANISM: Homo sapiens

<400> SEQUENCE: 61

Phe Thr Phe Gly Pro Gly Thr Lys Val Asp Ile Lys
 1               5                  10